United States Patent
Neev

(10) Patent No.: US 6,168,590 B1
(45) Date of Patent: Jan. 2, 2001

(54) METHOD FOR PERMANENT HAIR REMOVAL

(75) Inventor: Joseph Neev, Laguna Beach, CA (US)

(73) Assignee: Y-Beam Technologies, Inc., Lake Forest, CA (US)

(*) Notice: Under 35 U.S.C. 154(b), the term of this patent shall be extended for 0 days.

(21) Appl. No.: 09/132,537

(22) Filed: Aug. 11, 1998

Related U.S. Application Data

(60) Provisional application No. 60/055,577, filed on Aug. 12, 1997.

(51) Int. Cl.[7] ............................................. A61B 17/36
(52) U.S. Cl. ............................................. 606/9; 606/43
(58) Field of Search .................................. 606/2, 3, 9–11, 606/13–16, 36, 43, 44

(56) References Cited

U.S. PATENT DOCUMENTS

| | | | |
|---|---|---|---|
| 3,538,919 | 11/1970 | Meyer | 128/398 |
| 3,693,623 | 9/1972 | Harte et al. | 128/303.1 |
| 3,834,391 | 9/1974 | Block | 128/303.1 |
| 4,388,924 | 6/1983 | Weissman et al. | 128/303.1 |
| 4,617,926 | 10/1986 | Sutton | 128/303 |
| 5,059,192 | 10/1991 | Zaias | 606/9 |
| 5,226,907 | 7/1993 | Tankovich | 606/133 |
| 5,425,728 | 6/1995 | Tankovich | 606/9 |
| 5,595,568 | 1/1997 | Anderson et al. | 606/9 |
| 5,632,741 | * 5/1997 | Zavislan et al. | 606/9 |
| 5,836,938 | * 11/1998 | Slatkine | 606/9 |
| 5,879,346 | * 3/1999 | Waldman et al. | 606/9 |

* cited by examiner

*Primary Examiner*—Linda C. M. Dvorak
*Assistant Examiner*—Bryan K. Yarnell
(74) *Attorney, Agent, or Firm*—Christie, Parker & Hale, LLP

(57) ABSTRACT

A method for permanently removing hair utilizes the hair shaft and hair ducts to transmit light into the tissue sustaining the hair follicle, thereby permanently destroying or modifying the tissue in a manner which desirably mitigates hair growth. The method includes the steps of covering the patient's skin area with a high reflectance substance so as to substantially protect all skin components other than those sustaining the hair. The hair is optionally shaved or pulled out, and then the skin is illuminated with either a large-area electromagnetic radiation field for simultaneous destruction of multiple hair-follicles, or alternatively with a tightly-focused beam which destroys one hair at a time. Optionally, the beam may be rapidly scanned so as to destroy single hairs quickly in succession. The surrounding skin region is left substantially free of injury. This mitigates pain and enhances post hair removal healing.

41 Claims, 30 Drawing Sheets

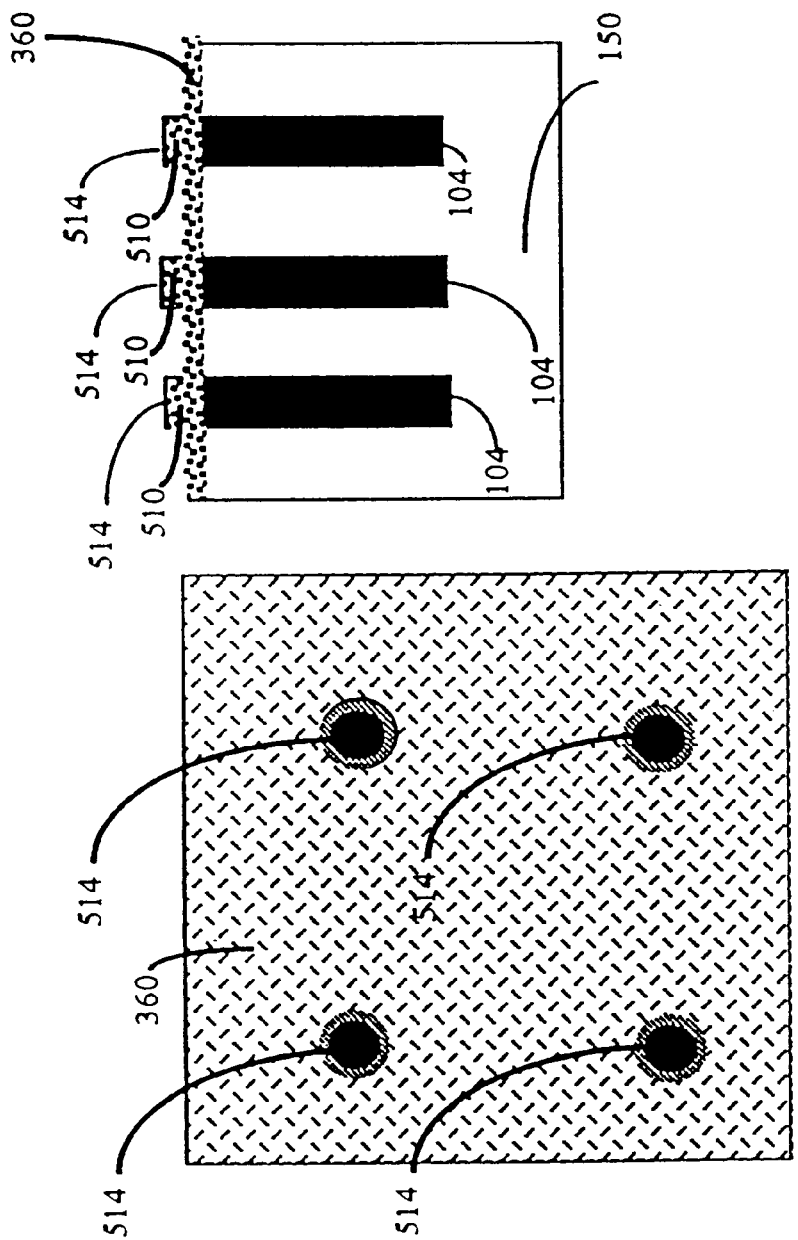

METHOD FOR PERMANENT HAIR REMOVAL

CROSS-REFERENCE TO RELATED APPLICATIONS

This patent application claims the benefit of the filing date of U.S. Provisional Patent Application Serial No. 60/055,577, filed on Aug. 12, 1997 and entitled "METHOD AND APPARATUS FOR SELECTIVE HAIR REMOVAL AND MODIFICATION," the contents of which are hereby incorporated by reference.

FIELD OF THE INVENTION

The present invention is related generally to hair removal and relates more particularly to the use of electromagnetic energy for the selective modification and/or removal of hair.

BACKGROUND OF THE INVENTION

As is well known, the human skin contains a number of components. For example, vascular and lymphatic channels provide for nutrition, healing and transport. Sweat and sebaceous glands provide respectively for temperature control and lubrication. Pigmented structures provide for sun protection. Hair follicles and their associated hairs provide for insulation and protection.

The components and function of human hair can be understood by reference to FIG. 1. Growth of each hair is originated by germinative fibroblast cells in the basal layer of the epidermis 152. The hair grows both outwards and inwards (towards the lower dermis 154 and hypodermis 158) during its growth cycle, and the follicle 100 develops as an encapsulating pouch extending beyond the epidermis and down several millimeters in depth into the subcutaneous fat. Each hair remains attached to the hair bulb 102 at the base of the follicle, where a capillary network develops to provide nourishment.

During an anagenic growth phase, hair matrix cells divide rapidly and migrate upwards to form the hair shafts 104 within the hair ducts 120. A subsequent catagenic phase is marked by cessation of mitosis, and the re-absorption of the lower part of the follicle. Capillary nourishment is greatly reduced during this phase. In this or a final telogenic (resting) phase, the hair falls out and a new hair may replace it in a new growth cycle. At any particular time, approximately 10% of scalp hairs will be in telogenic phase.

The growth cycle varies with anatomical location from as little as 3 months for facial hair to as much as 7 years on the scalp. Hair in the pubic area is typically retained by the body as protection and may not shed at all.

The hair follicle consists of a mixture of germinative cells and melanocytes. Sebaceous cells from the sebaceous glands empty into the follicle, providing a lipid-rich environment.

The follicle is typically about 0.1 to 0.2 mm in diameter and may extend up to about 4 mm in depth. The average hair shaft diameter within the follicle is about 60 to 75 $\mu$m. The hair shaft itself is generated as an accumulation of dead (keratinized) cells. Structurally it consists of two or three discrete layers: The outer cuticle layer consists of a single layer of overlapping flat cells like the scales of a fish. This acts as a protective barrier. An inner cortex layer contains any pigment which may be present. Pigments may also reside in melanocytes which line the follicle 100. Pigments may exist as two melanin forms. Eumelanin is responsible for brown/black coloration and pheomelanin is responsible for red/blonde coloration. Larger, fully developed hairs also contain a core known as the medulla.

In the lower region of the follicle, a bulge is formed where the arrector pili muscle 110 contacts the follicle. This muscle controls movement and orientation of the hair and may, under some stimuli, render the hair vertical with respect to the skin surface. The bulge area has one of the fastest rates of cell division found in mammals, stimulated by growth factors from the lower papilla 112 area.

Because dermal thickness varies greatly over the body, the papillae may be superficial (as in, for example, the eyelids and scrotum), but for many areas of interest for the practice of the present invention (e.g., the face, axillae, and legs), the papillae are located at depths of approximately 4 to 7 mm beneath the epidermal surface.

Located a few tenths of a millimeter below the papillae are neurovascular bundles which serve the metabolic and other needs of a hair matrix.

The hair matrix is the region of rapidly growing keratinizing cells, located in the papilla 112, which produce the hair shaft 104.

It is important to note that the matrix, papillae, and their associated neurovascular bundles are necessary for hair growth. By destroying or modifying these anatomical structures, hair growth is mitigated. Thus, the matrix, papilla, and the corresponding vascular bundle represent the follicular targets to be destroyed. According to the present invention, during the treatment of these regions, the depilatory effects are localized so that damage is confined to a small region of dermis surrounding each follicle.

The extent of damage should preferably be much less than half the distance between neighboring follicles (typically between about 1 and 4 mm). If it is significantly greater than this, the injury may result in a third-degree burn.

While the follicle and hair contained therein function at several different levels, excess body hair does present a cosmetic problem for hirsute females, and some males as well. As a consequence, many individuals undergo hair removal treatments. Conventional hair removal techniques, including electrolysis, shaving, wax epilation and tweezing, are often painful and temporary.

Electrolysis is used by an estimated 1 million women in the United States. Two techniques dominate the electrolysis field. Galvanic (DC) current can be passed down a fine needle inserted into the follicle. This technique converts tissue saline locally to sodium hydroxide, which destroys the follicle. Alternatively, the thermolysis technique utilizes an AC current to directly heat and thereby destroy the papilla. Some clinicians utilize a combination approach of these two electrolysis technique. Electrolysis methods are only used to treat follicles one at a time. This is an undesirably painful procedure which can require analgesia. Disposable needles are used in this frequently nonpermanent, time consuming, multiple treatment technique.

Several contemporary photonics techniques have also been evaluated. In 1993, Thermotrex Corporation was assigned two Hair Removal Device and Method patents (U.S. Pat. Nos. 5,226,907 and 5,425,728) based on the use of an externally applied chromophore to enhance local absorption of laser light. In these patents, a topically applied substance is said to penetrate to the full depth of the root of the follicle. The substances cited include permanent hair dyes, suspensions of carbon particles and photosensitizing compounds. A subsequent application of laser light is said to induce a reaction which destroys the follicle and a surrounding tissue area. The compounds cited by ThermoLase in their patents will probably demonstrate follicular selectivity. Many other topical compounds, and some systemic compounds, exist as candidates. Liposomal or lipophilic compounds may favor the lipid rich environment. Alternatively, solvents such as ethanol may be used to de-lipidize or re-organize the saburra, and thereby open the follicular passageways.

Deposition of hydrophilic drugs may be facilitated by the action of wetting agents such as sodium lauryl sulfate, which may promote the creation of an emulsion. Particle size clearly plays a role in terms of ability to penetrate through narrow epidermal structures and along the follicular duct. The approach cited in this issued patent may work, although its practice involves the use of light absorbing topical compounds and short pulse durations which may result in explosive events with significant collateral damage to adjacent skin tissue. Furthermore, the approach cited in this patent involves non-selective deposition of the absorbing compound along the entire follicle with a correspondingly non-selective deposition of laser energy. This, in turn, may prevent effective destruction of the follicle sustaining tissue. Indeed doubts exist as to effectiveness of this invention as a permanent method for hair removal.

A second technique has been studied and reported by Drs. Rox Anderson, Melanie Grossman, and William Farinelli (U.S. Pat. No. 5,595,568) whereby single high energy normal mode ruby laser pulses are applied to the skin in the absence of an externally applied chromophore. In this method, the optical target is the melanin within the inner cortex layer and the pigment-bearing melanocytes lining the follicle. High fluences of up to 200 $J/cm^2$ are used in large spot sizes, with pulse widths in the range of 50 microsecond 200 ms and wavelengths of 680 to 1200 nm. This technique employs a number of natural phenomena to enhance effect on the deep follicular component. A large applied spot size and high fluence allow for maximum depth of penetration. Concurrent cooling spares bulk tissue structures from the edema and general damage which can result from the use of fluences of this magnitude. Intimate index-matched contact of the custom handpiece with the tissue mitigates reflection loss.

Of concern is the use made by this invention of relatively large, spatially-continuous beam spots which are known to result in higher temperature increases of the targeted tissue volume due to less efficient thermal transport. The high fluences involved are applied directly to the entire volume of the target skin, in combination with non-selective irradiation of the skin (the method relies on expected higher absorption in some types of hair shafts and follicles but not on selective irradiation conditions), may also result in an increased risk for thermal and/or mechanical damage to non-targeted components of skin.

In addition, the relatively short pulse widths used in this approach may not efficiently transfer heat to the entire follicular structure and thus may not be effective in achieving permanent hair removal.

A third approach, utilizing the Q-switched ruby laser, was disclosed by Nardo Zaim in his 1990 U.S. Pat. No. 5,059,192. This patent cited the use of a Q-switched ruby laser at a wavelength of 694 nm, with 3–8 mm spot size and around 8 $J/cm^2$. Pulse width was in the range 30–40 nanoseconds. Light energy administered in such a short pulse width will be well retained in the melanocytes lining of the follicle. This approach will provide potential for melanocyte destruction and perhaps permanent depigmentation or destruction of the hair, but likely will not kill the follicle itself, since the pulse width is insufficiently long to conduct heat away from the targeted melanin granules.

Other approaches have been described. In 1967, U.S. Pat. No. 3,538,919 was filed by R. Meyer. Meyer cited the placement of a fiber directly into the follicle into which a total of 30–40 $J/cm^2$ of light was subsequently launched. This fluence was administered over a period of 1–2 seconds, preferably by a normal mode ruby or ND:YAG laser. Use of a 50 $\mu$m fiber was cited. This fiber diameter would theoretically fit into a 100 $\mu$m follicle containing a 60 $\mu$m hair shaft, but with some difficulty. Also, the technique would be time consuming to administer, on a single hair-by-hair process.

In 1970, Richard Haite filed U.S. Pat. No. 3,693,623, which also cited the placement of a fiber directly into each follicle to be destroyed. The light source here was a xenon lamp which applied up to 3 mJ to each follicle, in an interval of less than 3 ms. This technique again addresses each hair individually in a tedious and difficult to administer process.

In 1973, Carol Block filed U.S. Pat. No. 3,834,391, which similarly addressed the placement of a fiber at the follicular entrance. Light source was unspecified. This patent introduced the concept of the use of mineral oil, which was said to facilitate light conduction, presumably by index matching. No additional chromophore was added. This technique in this patent calls for the destruction of each hair on an individual basis in a tedious and difficult to administer process.

In 1981, H. Weissman filed a patent application, later granted as U.S. Pat. No. 4,388,924. This patent cited the devitalization of hair by the specific destruction of the papillary blood supply. A narrow beam from an Argon laser was directed onto the tissue. This light was said to be absorbed by the papillary plexus, causing heating and coagulation. Multiple 20–30 millisecond exposures from a 0.5–2.5 Watt beam were cited. The hair was subsequent tweezed from its follicle. This method suffers again from the individual hair-by-hair approach, which is time consuming. Also, the selective destruction of the papillary plexus is unlikely to be practical using an Argon laser, with its limited penetration depth capabilities. The blood supply resides at several millimeters and is shielded by the overlying follicular structure.

In 1984, A. Sutton filed a patent, later granted as U.S. Pat. No. 4,617,926. This provided for the use of a fiber without a core, into which an individual hair slides by 2–3 mm. Different probes were cited. About 1 Joule of energy was launched into the fiber, from an unspecified laser source. In an alternative embodiment, the fiber is sharpened and inserted directly into the follicle. This technique is time consuming and tedious and is likely to result in rapid probe destruction.

None of these references appear to address the problem of mitigating undesirable collateral damage to adjacent skin and/or tissue.

SUMMARY OF INVENTION

The invention comprises a method and apparatus of destroying or modifying selected single or multiple hair follicles from a patient's skin so as to mitigate the occurrence of hair regrowth.

The invention consists of several embodiments which can generally be grouped into three principle methods:
1. Removing selected hair through the direct coupling of electromagnetic energy to the follicle, its components, or sustaining tissue;
2. Enhancement of heat conduction to the hair root; and
3. Direct ablation of the hair shaft and hair sustaining tissue.

Most of the preferred embodiments (based on all three methods) rely on the application of a layer of a high reflectance coating to the skin's surface, which provides both protection for the hair-free surface, as well as a means for identifying the hair shaft location.

Thus, many of the embodiments of the present invention include three steps: a) covering the patient's skin at the location of the selected hairs with a substance having high reflectance properties that will substantially protect all hair-free skin components, b) cutting or shaving the selected hair shafts, or alternatively, pulling the selected hair shafts out of the skin, and then, c) illuminating the selected hair follicles with either a large-diameter beam of electromagnetic radiation for simultaneous destruction of multiple hair follicles, or alternatively, illuminating the targeted skin area with a tightly-focused, small diameter beam of electromagnetic radiation which is rapidly scanned, thus enabling the sequential destruction of the selected single hairs. The rapid scanning rate thus compensates for the more time-consuming single-hair interaction.

These steps allow portions of the hair follicles to be destroyed, thereby, leading to the permanent removal of the hair. The surrounding skin region is left substantially free of injury.

In a more general way, the steps of application of a high reflectance substance to the skin, followed by the hair shaft cutting, provides a mechanism for identifying and selectively coupling the beam to the hair shafts. This also provides a new way to identify the hair shaft opening quite rapidly, precisely, and if desired, in an automated manner which, in turn, allows for rapid scanning techniques. Consequently, a new method is created for the detection of differential absorption/reflection on the skin's surface. This is a method that enables rapid and efficient mapping of hair follicle location and forms the basis for a selective treatment of the hair follicles and their surrounding tissue.

Some of the embodiments of the present invention also utilize the fact that it is possible to couple and propagate electromagnetic energy down the hair shaft, hair ducts, hair follicle, and even down into the skin tissue surrounding the hair follicle.

In addition, some of the embodiments of the present invention utilize an ability to manipulate skin and hair properties to optimize follicle destruction. For example, the present invention provides an ability to change hair shaft pigmentation, to insert artificial substances into the hair ducts, and manipulate their optical and thermal properties, or to completely remove the hair shafts from the skin and utilize the emptied hair duct space to couple electromagnetic energy to the follicle or to insert additional substances to the skin, which, in turn, enhance coupling and conduction of said energy to the targeted hair-sustaining tissue.

Other aspects of the present invention utilize a hair follicle identification method. This method is based on differential absorption and reflection created through coating of the skin's surface with a layer of high reflectance substance followed by hair shaft cutting. This allows the operator to identify the location of the hair follicle and to create delivery windows of various diameters and depths in the layer of high reflectance coating around the hair follicles. This, in turn, allows the delivery of the incident energy either through direct optical penetration, or through the conduction of the deposited thermal energy to the tissue sustaining the hair, thereby causing irreversible damage and removal of the hair.

Optionally, a high reflectance coating may be applied to recently shaved, plucked, or otherwise depilitated skin. The reflective coating is selectively removed at each follicle, so as to allow light energy to enter the follicle. The removal may be effected by mechanical scrapping or poking by utilizing a needle, stylus or the like, or alternatively via laser ablation or the like. When laser ablation is used to remove the reflective coating, a first laser pulse removes the reflective coating at the follicle and a second laser pulse effects hair removal. When a stylus is used, the stylus preferably has a tip which has a diameter of between approximately 20 micrometers and approximately 2 mm, so as to facilitate removal of the desired amount of the reflective coating (typically an amount approximating either the cross-sectional area of the hair to be removed or the area of the opening of the follicle.

The invention also provides for irradiating the targeted skin without the application of a layer of a high reflectance coating. Instead, the invention utilizes the naturally occurring differential absorption/reflection of the natural skin in combination with hair shafts, cut close to the skin. These embodiments of the present invention allow for an alternative method for the identification of the hair follicles and lead to the coupling of the depilatory incident energy to the targeted hair-sustaining tissue by utilizing the hair follicles and their immediate surrounding for energy transport.

Finally, the present invention also provides for the use of several methods for enhancing safety and cooling of the skin's surface during treatment.

The method of the invention is carried out using a device which includes means (for example, a laser) for generating electromagnetic radiation, and an irradiating unit including a scanning/treatment device for receiving and then delivering the radiation to the skin region of the patient. The scanning/treatment device consists essentially of either a large diameter or a small-diameter beam in conjunction with a source and delivery means for a second, low powered interrogating beam. The scanning treatment head is in close proximity to or in direct contact with multiple hair follicles in the treated skin region.

It is the intention of the present invention to provide permanent hair removal by either destroying or substantially modifying the follicle, papilla, or adjacent tissue such that hair growth is no longer supported. However, as those skilled in the are will appreciate, in some instances a degree of hair regrowth may occur, thus necessitating re-treatment.

Optionally, a first beam of electromagnetic radiation may be utilized to sense the presence and/or orientation of hair/follicles, and machine vision or the like may then be utilized to direct a generally more powerful beam of electromagnetic radiation to the hairs/follicles, preferably one hair/follicle at a time, so as to effect permanent removal of the hair at that location. Those skilled in the art will appreciate that various means, such as color, contrast, etc., may be utilized to facilitate such a distinction between a hair/follicle and the surrounding skin. For example, a pattern recognition algorithm that was configured so as to direct the hair removing beam of electromagnetic radiation to those locations having a gray scale of either above or below 1000 au, as desired.

A simple microprocessor may be used to compare signals from a photodiode monitoring the reflectance of the high reflectance coating. When the reflectance drops to a value below a predetermined value, i.e., the average value of the high reflectance coding then a hair/folicle has been found and the hair removal beam of electromagnetic radiation is directed toward the hair/folicle so as to effect permanent removal thereof.

While the present invention is intended primarily for removing hair from human skin, those skilled in the art will appreciate that the method and apparatus of the present invention may likewise be utilized to remove hair or the like from other mammals as well. Indeed, the present invention may be utilized to remove hair-like structures from various non-mammalian creatures, as well as non-living things.

Other features and advantages of the invention will be apparent from the following description of the preferred embodiments.

BRIEF DESCRIPTION OF THE DRAWINGS

For a better understanding of the nature and objects of the invention, reference may be made to the following detailed description and the accompanying drawings, in which:

FIGS. 5C and 5D are graphical representations of the high reflectance coating layer on the targeted skin area and of the uncoated, shaved, hair shafts openings, after the shaving of the hair shafts wherein FIG. 5C is a plan view and FIG. 5D is a cross-sectional view;

DETAILED DESCRIPTION OF THE PREFERRED EMBODIMENTS

The principles of operation of a method and apparatus for permanent hair removal and/or modification are described in detail in the sections that follow. The apparatus comprises a source of pulsed electromagnetic radiation and must comply with the requirements of the invention. In the following discussion, a laser source is used as an exemplary pulsed source of electromagnetic radiation. However, those skilled in the art, will recognize that the invention is not limited to laser sources and that other pulsed electromagnetic radiation sources (including incoherent electromagnetic radiation sources) may serve equally well in the practice of the invention. The principles of operation of such an exemplary laser system will now be developed in connection with the mechanisms of selective light delivery to the desired hair and hair-sustaining targets, and the simultaneous minimization of collateral damage to adjacent tissue structures.

Several preferred embodiments are described below. All embodiments, however, share many aspects of the same preoperative and post operative steps that are designed to enhance treatment outcome while mitigating collateral damage to the skin as well as patient's pain and suffering. Additionally, many of the same basic features are used in all embodiments of the present invention apparatus for hair-removal and modification. Accordingly, these common steps and common apparatus features will first be described.

COMMON ELEMENTS SHARED BY PREFERRED EMBODIMENTS

Figure 1:
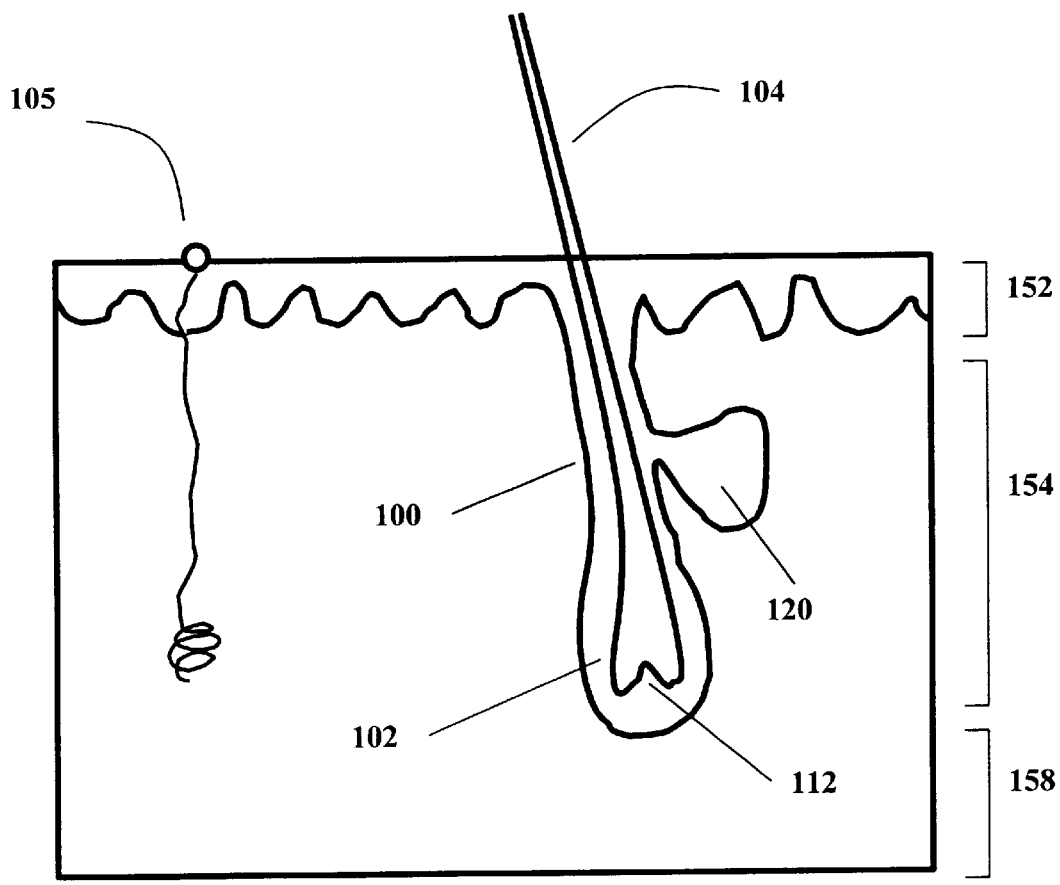
FIG. 1 is a sketch of the anatomy of a skin section containing hair follicles and other relevant skin structures.
Figure 2:
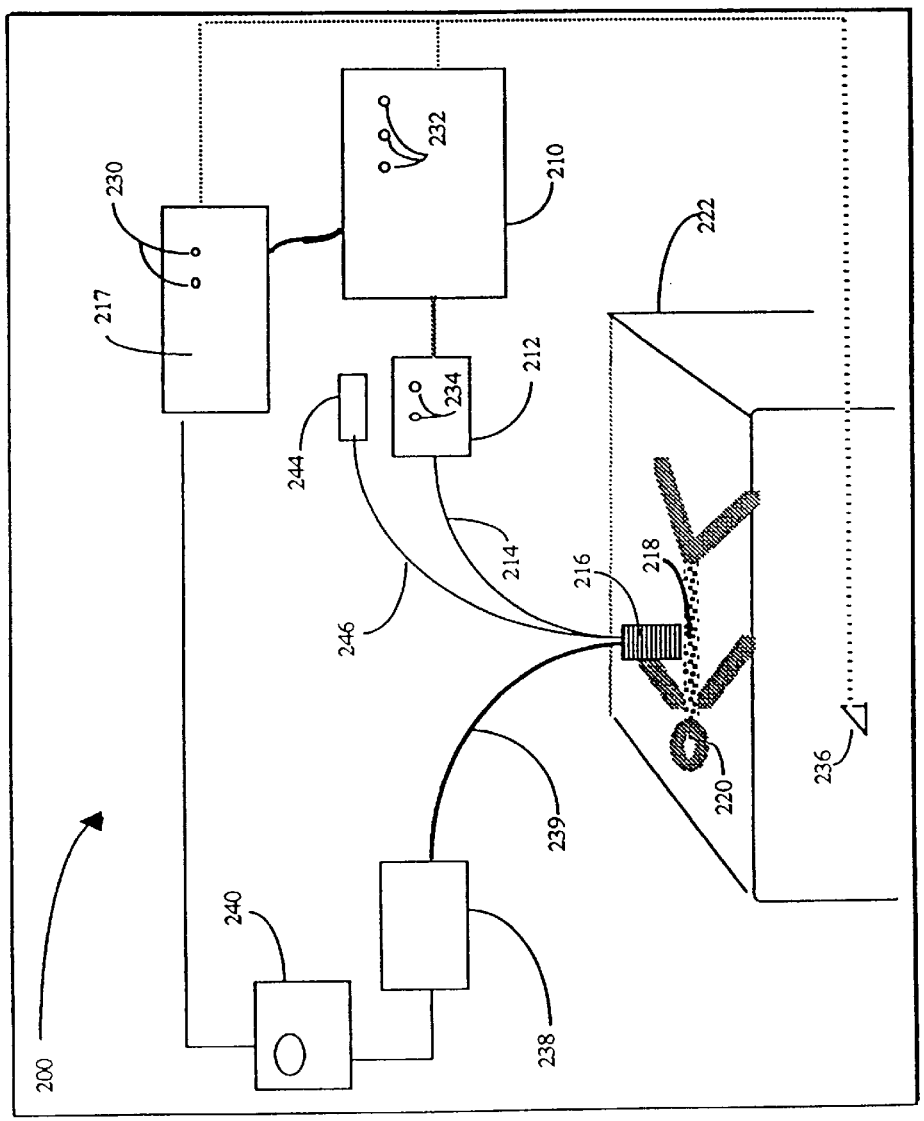
FIG. 2 is a perspective view of an exemplary, laser-based hair modification and removal apparatus according to the practice of the present invention.

Referring to FIG. 2, a laser-based hair-removal system 200 includes an electromagnetic radiation source 210, which may, for example, include one or more lasers for generating the irradiating field. The light source 210 is preferably optically coupled to a series of beam-manipulating optics 212 which, in turn, may be coupled via a beam delivery module 214 (for example, a fiber optic cable or other waveguide or beam-delivery device) to the scanning/treatment head unit 216.

During the hair-removal process, the light source is powered by a voltage and current supply 217, and delivers a beam of light through the optics 212 and beam delivery module 214 to the scanning/treatment head 216. The field is then delivered to the targeted region 218 on the patient's skin 220 (the patient is positioned, for example, on a platform 222) resulting in hair removal from the desired region 218.

After the designated region is treated, the region is preferably inspected by the operator to determine the degree of hair removal. The irradiating unit can then be easily moved along the patient's skin 220 and used to treat subsequent regions.

The spatial and temporal properties of the optical field determine the efficacy of the hair-removal process, and may be adjusted using a series of controls 230, 232, 234 located on various components of the hair-removal system 200. For example, using controls 230 located on the power supply 220, the optical intensity and pulse repetition rate of the irradiating field can be controlled by adjusting parameters such as the supplied voltage, current, and power supply switching rate. Other properties of the field, such as the wavelength and pulse duration, may be varied by controls 232 which adjust components (e.g., gratings, mirror or filter positions, shutters, or pulse-forming means) of the light source 210. Similarly, controls 234 can be used to adjust the modulating optics 212, resulting in control of properties such as mode quality, beam diameter, and coupling of the irradiating field into the beam delivery module 214. All controls are preferably adjusted either by hand, or by using a foot pedal 236 connected to the power supply 217 or to the radiation source 210.

Alternatively, the system may be fully or partially automated through the use of an automated feedback/analyzer 238 and a computer/control module 240 and connected to the power supply 217 and/or radiation source 210. Electrical and/or optical signals from the interrogated tissue may be carried through a cable 239 to the feedback/analyzer unit 238.

In alternate embodiments the light source, coupling optics, and irradiation unit may be encompassed in a single, hand-held device. In this case, the light source is preferably an array of diode lasers coupled directly to the irradiating unit, and is powered by a small external power supply.

Such compact nature of this type of optical system allows for a more controllable, maneuverable device, and additionally obviates the need for fiber optic delivery systems.

Finally, an auxiliary weak laser source 244, (for example a diode laser of about 670 nm and less than 1.0 mW in output) may be used to provide a separate radiation source for aiming, scanning, interrogating and diagnosing the targeted tissue area. The auxiliary source 240 may be coupled to the scanning/treatment head 216 via a separate or partly separate delivery module 239.

PRE-OPERATIVE STEPS

1. SKIN INSPECTION AND SKIN PREPARATION

The hair-covered targeted area should not be shaved or disturbed for a time period sufficiently long to allow hair growth to a length of a few millimeters. A few days period should be sufficient for most people, although the length of said period will vary from person to person according to the individual's rate of hair growth. The reason for such a wait is simply to allow sufficient amount of time for allow the hair to grow long enough, approximately 0.2 mm, to facilitate the treatment of the present invention. The hair should be long enough so it can be easily handled in the embodiments that required hair manipulation and/or removal (for example, in embodiment where the step of wax-removal of hair is rendered useful). Yet the hair should not be allowed to grow too long (for example greater than about a few centimeters) so that the steps of the application of pre-operative topical substances to the skin would become difficult to accomplish and/or ineffective.

The targeted area of the skin should be thoroughly cleaned and treated with disinfectants. The skin surface must be inspected for hair condition, cleanliness, special morphological features, color of hair, and any abnormalities or skin diseases as well as length and thickness of hair. The presence of scarring, or abnormal texture, color or morphology should be noted. Also, the targeted site is optionally photographed and the number of hairs per unit area (surface hair density) should be noted.

Both the hair and the hair follicles are often oriented at some angle to the surface. As part of the evaluation process, this hair shaft orientation should be noted and recorded. The operator should also note whether or not the hair shafts orientation represents a consistent pattern. This short evaluation can be useful in order to allow the scanning/treatment 216 head emitting the depilatory beam to be oriented at an angle that matches the patron's specific hair orientation and optimizes hair coupling. For reasons that will soon become clear such treatment head will henceforth be referred to as the scanning/treatment head or S/T head 216, and is depicted in FIG. 2 among the other features of a laser-based hair modification and removal apparatus.

The step of determining the hair orientation can be accomplished with an electro-optical instrument and made easier by automating the procedure as described below.

After a layer of high reflectance coating (HRC, to be described below) is applied to the targeted skin surface, the hair shafts are cut as close to the skin surface as possible yet substantially without damaging or removing the high reflectance coating layer. These two steps are described in detail below.

Figure 3A:
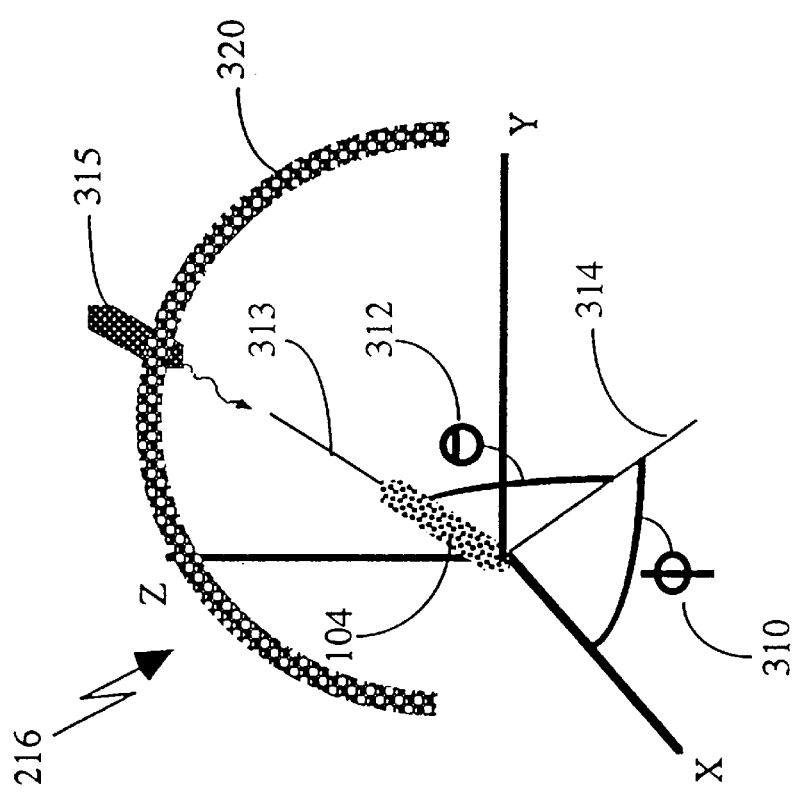
FIG. 3A is a graphical representation of a device and a method for determining hair shaft orientation.

Referring now to FIG. 3A, in order to determine shaved hair shaft opening orientation, a weak (for example, 1.0 mW) interrogating light source 244 (see FIG. 2) may be used. Such a weak beam source may, for example, consist of a low power laser diode. The interrogating beam direction of incident may be rotated about the two angles defining the beam direction of incidence 313 (see FIG. 3A), namely the polar angle $\theta$ 310 (namely, the angle $\theta$ between the line defined by the hair direction/beam direction of incidence 313, and the line 314 defined by the projection of 313 on the X-Y plane) and the azimuthal angle $\phi$ 312 (namely, the angle $\phi$ between the X-axis and the line 314). A large area light detector 320, collects substantially all the backscattered or reflected light. The principle of detection is that light upon reflection off the coated surfaces (regardless of multiple reflection events) will return substantially with very little attenuation to the detection element. A drop in the reflected light intensity to a minimum indicates maximum light coupling to the cut, uncoated, hair shafts 104 and hence optimal direction of incident.

2. APPLICATION OF A LAYER OF HIGH COATING

Many of the preferred embodiments described below include an initial application step of coating the skin with a high reflectance coating (HRC). This substance may be in the form of a fluid, liquid or powder but must cover the skin and the post-inspected hair in the targeted area in a substantially uniform manner. The material applied as a layer of high reflectance coating to skin surface must be able to substantially reflects much of the incoming beam energy. For example, a reflectance in the range of about 80% or more in the region of the electromagnetic spectrum utilized by the source should be an adequate property of such HRC substance.

The substance comprising the layer of high reflectance coating can be any liquid, gas, solid powder or particulate, suspension, or vapor, as long as such a substance fulfills the aforementioned requirement of high reflectance in the electromagnetic spectrum emitted by the sources used in the practice of the present invention.

Care must be taken to ensure that the aforementioned material of high reflectance applied to the skin are comprised of substances which are not toxic or harmful in any way to the skin and tissue. If for some reason a HRC substance of questionable safety has to be selected, the HRC must be made of substances which are unable to penetrate the outer surface of the skin. For example, a HRC suspension must utilize particles large enough to be unable to penetrate the hair ducts or any skin pores or openings. The particles are preferably larger than approximately 30 micrometers in diameter.

Body paints, metallic hair dyes, or other non-toxic and safe coatings having high reflectance properties may be used. Dielectric coating, multilayer dielectric or any other means that might substantially enhance the reflectivity of the natural skin surface may also be used as long as they are non-toxic and safe for use on the skin.

However, as will be described below, some embodiments of the present invention require insertion of high reflectance substances into the hair ducts prior to (as well as after) hair shafts cutting or the pulling of the hair shafts out of the skin. In these instances the particles or substances used as HRC must be non-toxic and safe for the skin and for insertion into hair ducts and penetration into the skin pores.

Figure 3B:
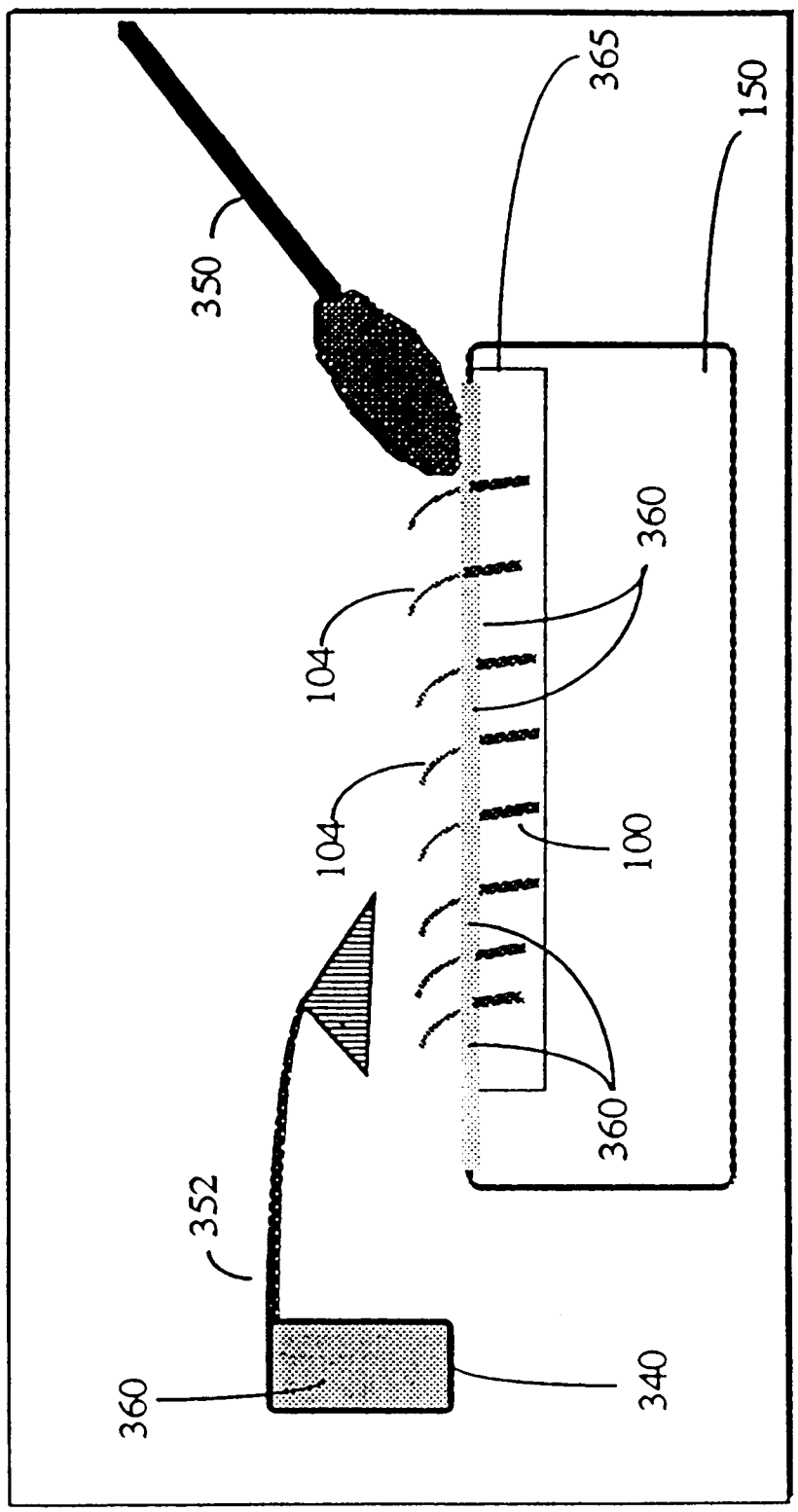
FIG. 3B is a graphical representation of two methods (spraying and brush-paining) for application of a high reflectance coating (HRC) to the skin.

Referring now to FIG. 3B, the application of HRC 360 to the target surface can be accomplished through the use of a brush 350, a spray dispenser 352 (connected to the HRC container 340), through dusting (not shown), or even submerging of the targeted skin area in a container filled with a high reflectance coating substance (not shown). It is important, however, to ensure that substantially all the exposed skin in the target area as well as some additional peripheral skin area (for safety consideration and to enhance the removal of potentially damaging excess heat) shall be well covered with such HRC.

It is also important that such HRC should not be easily or accidentally removed and that it will be capable of covering the targeted zone for the entire treatment period and preferably (again, for safety reasons) much longer, i.e., for at least a few hours. Finally, it is also possible in some cases to simply soak the general area targeted for hair removal in a container full of the HRC liquid. Such application would probably ensure the most thorough covering of the skin and hair by the HRC substance.

In some embodiments of the present invention it may be useful to force some HRC fluid into the hair follicle or along the side the hair shaft. In such cases, massaging or the application of ultrasound may be used in order to enhance application of the HRC substance. Such forced application can, for example, consist of an ultrasound energy field with frequencies in the range of 3.0 to 10 MHZ at a power level of about 0.1 to 0.2 watts for 2 to 20 minutes.

For the successful practice of the present invention it is also important that the high reflectance coating layer 360 shall be easily removed by commercial solvents, soaps, or other safe and effective body cleaners commonly used, and that such high reflectance coating material shall in no way be harmful to the skin or to the health and safety of the subject of the treatment.

3. APPLICATION OF A COOLING/FREEZING AGENT

In order to facilitated epilation, a cold medium or a freezing agent may be applied prior to the use of the depilatory beam in order to cause the hair root structure and the hair follicle to move to a location generally closer and perpendicular to the surface of the skin, and to enhance safety and prevent over heating and thermal damage to other skin components.

POST-OPERATIVE STEPS

1. SKIN DRESSING AND SKIN MEDICATION

Following treatment the skin should be thoroughly washed and cleaned of any residual HRC that may have accumulated. Patients should also be treated with topical antibiotic ointments.

After the procedure the patients should also be given the following instructions: use an antibiotic ointment topically for the first three days; protect the area irradiated when taking shower and do not expose it to water or washing, do not use hard sponges; protect the area from direct sunlight; take a mild pain medication such as aspirin if there is any discomfort; and call physician if necessary. Examine the skin at 1, 2 and 3 week intervals. Repeat the procedure if necessary for the hairs which were in anagen or catagen phases during the irradiation procedure.

OPTICAL FIELD PARAMETERS EFFECTING FOR IRREVERSIBLE HAIR DAMAGE

A fourth element that is common to all embodiments of the present invention is the step involving the application of the depilation beam to the targeted hair.

As described in the specific embodiments below, there are several possible methods of delivering depilatory energies to the targeted, follicle-sustaining tissue (as defined in the background section above).

Depending on the specific method for depilatory energy delivery, the precise steps taken in the practice each of the embodiments described below. The resulting energy temporal and spatial distribution. For each one of these embodiments may require some variation and specific adaptation in the preferred optical field parameters.

In general, however, a hair follicle 4 mm deep and 200 $\mu$m wide will occupy about $1.2 \times 10^{-4}$ cm$^3$ of tissue and will weigh about 130 $\mu$g. Raising the temperature of such a follicle to above the coagulation temperature requires Approximately 42 mJ. Delivered over the follicle's cross section of 0.005 cm$^2$, this total energy translates to a total fluence of about 8.5 J/cm$^2$. For example, delivering this energy over a time duration of 1 ms to 10 ms long this deposited heat will only defuse a distance of about 20 to 70 $\mu$m from the deposition volume. Consequently, heat will substantially remain confined to within the follicle volume during the time of exposure to the beam, making destruction of the follicle likely while limiting collateral damage to the adjacent skin tissue.

The fluence of the incoming beam will vary according to the specific embodiment used and the optical and thermal properties (for example, the degree of pigmentation, the amount of oil in the hair ducts, etc.) of the patient's hair and skin. The fluence of the incoming beam will also vary according to the specific location of the treated hair and skin on the patient's body. In embodiments involving beam propagation through the hair shafts, for example, patients with darker hair will require light of higher fluence than patients with lighter hair. As described herein, in all cases, the beam energy should be adjusted in order to heat the targeted regions to a the desired temperature of about 70° C. to about 125° C.

Two broad methods for beam energy coupling are disclosed: 1) single hair coupling/small beam spot-size/rapid-scan method; and, 2) simultaneous multiple hair coupling/large beam spot-size.

Within each one of these two categories, there are several possible methods of delivering depilatory energies to the targeted, hair-sustaining tissue. These include, but are not limited to:

a) Incident electromagnetic energy coupling and propagation through the hair shafts to the targeted area to be destroyed (see discussion in the background section above).

b) Absorption of the incident electromagnetic energy by the cut hair shafts and their immediate surrounding, conversion of said energy to heat, followed by heat conduction to the targeted area to be destroyed.

c) Removal of hair shaft followed by coupling and propagation of the coupled beam energy through the emptied hair ducts to the targeted area to be destroyed.

d) Removal of hair shafts followed by both beam coupling to the emptied hair ducts, as well as absorption in the hair ducts and heat conduction to the targeted area to be destroyed.

e) Ablative removal of the hair and hair follicle.

In some embodiments, as will be made clear by the discussion to follow, more than one of these interaction paths may play a role simultaneously.

The generally preferred optical parameters for each of the two broad depilatory beam application methods will now be described. Additional field parameters will be described as needed in the specific embodiments.

SINGLE HAIR INTERACTION/SMALL BEAM SPOT-SIZE/RAPID-SCAN METHOD

In this case the beam is focused to a dimension on the order of the diameter of a single hair shaft or smaller. When the hair and the beam are aligned, all the incident light is intercepted by the hair shaft surface and the entire beam, at the time of such an alignment, is directed at the targeted hair alone. To maintain a practical total treatment time, the dwell time of the beam over a single hair shaft should be sufficiently short and the scanning of the depilatory beam over the targeted surface should be reasonably fast.

Within the single hair interaction method, the parameters corresponding to the five aforementioned methods for delivering depilatory energies to the hair-sustaining tissue are as listed below:

a) Incident Electromagnetic Energy Coupling and Propagation Through the Hair Shafts to the Targeted Area To Be Destroyed.

In this case a wavelength range of from about 300 nm to about 2.7 $\mu$m can be envisioned (especially if the step of melanin removal through bleaching or discoloring of the hair shafts is taken, as described below). However a preferred range is substantially from about 700 nm to about 1200 nm. Alternatively, a range of 300 nm to 700 nm may be utilized.

Figure 4A:
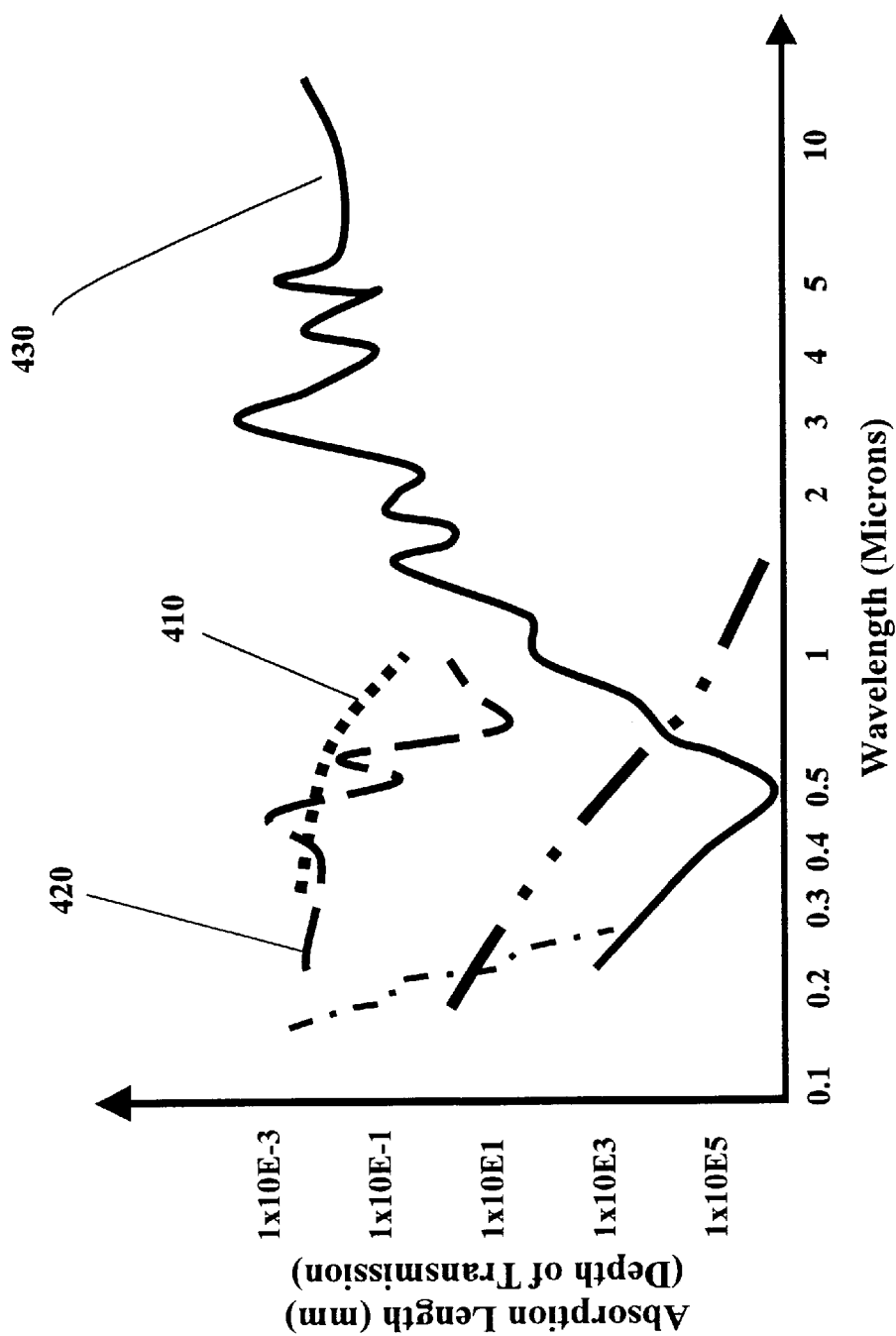
FIG. 4A is a graphical representation of water, melanin and hemoglobin absorption length vs. the wavelength (in micrometer) of the incoming radiation.

As shown in FIG. 4A, this range is preferred because the absorption of melanin and water is reduced in this spectral range while the absorption of hemoglobin (one of the components of the targeted papilla and hair-sustaining tissue) rises. The fluence in this case is in the range of 1 to 300 J/cm$^2$ with a preferred value of 15 to 65 cm$^2$. Alternatively, the fluence has a range of 0.3 KJ/cm$^2$ to 1000 KJ/cm$^2$. Pulse duration should be in the range of (depending on the fluence level used) from about several hundred nanoseconds to about 0.5 seconds with the preferred values of 5 femtoseconds to 50 ms. The beam diameter (FWHM) in this single-beam/single hair interaction configuration should be in the range from about 5 $\mu$m to about 360 $\mu$m with a preferred value of from about 5 $\mu$m to about 60 $\mu$m. A conventional lens or a fiber lens with an f number in the range of from about 0.4 to about 2.5 may be used with a preferred range of from about 1.0 to about 1.7. If a low refractive index substance is forced into the hair ducts its value should be lower that of the hair shaft (i.e., lower than about 1.5). If an external index-matching fluid is used its value should be greater than about 1.3 and preferably between 1.4 and 1.7.

b) Absorption of The Incident Electromagnetic Energy by The Cut Hair Shafts And Their Immediate Surroundings, Conversion of Said Energy to Heat, Followed by Heat Conduction (Including Operator-enhanced Heat Conduction Through The Insertion of a Good Heat Conductor to The Hair Ducts) Toward The Targeted Area to Be Destroyed.

Here high absorption by the melanin or, in embodiments which employ HRC removal from areas larger than only the cut hair shafts, high absorption by the exposed follicle and skin is desired. In this case fluences, pulse duration, beam diameter and index matching would remain substantially similar to the case described in (a) above. The wavelength, though, would now allow for absorption at the upper follicle and upper hair shaft and would thus include the range of from about 0.3 $\mu$m to 11 $\mu$m, with the preferred range of 0.3 $\mu$m to 0.7 $\mu$m where absorption by the targeted tissue components as well as melanin is generally high.

c) Removal of Hair Shafts Followed by Coupling And Propagation of The Coupled Beam Energy Through The Emptied Hair Ducts to The Targeted Area to Be Destroyed.

Here, the hair ducts are emptied or emptied of the hair shafts but filled with a transparent substance. The beam parameters should remain the same but less energy may have to be applied because much of the absorption in the hair shaft is eliminated and propagation has been enhanced. Fluence may thus be reduced by a factor of about 2 or even more. Concerns about melanin absorption are substantially reduced and the wavelength may thus cover the entire range of from about 0.3 $\mu$m to about 1.3 $\mu$m.

d) Removal of Hair Shafts Followed by Both Beam Coupling to the Emptied Hair Ducts, As Well As Absorption in the Hair Ducts and Heat Conduction to the Targeted Area to be Destroyed Here the invention relies partly on thermal conduction to deliver the depilatory energy down to the targeted hair-sustaining tissue. The emptied hair duct may be filled with beam absorbing substance which is also a good conductor (see description in specific embodiments below) and thus is not strongly dependent on the absorption characteristics. The entire wavelength range from about 0.1 $\mu$m to about 11 $\mu$m may be used (or even larger spectral range can be envisioned if appropriate inexpensive sources are identified. Other then the wavelength range, other beam parameters are expected to be substantially similar to those described in case (a) above, although higher fluence values may be needed if excessive thermal losses occurs in the upper follicle region.

e) Ablation

The fluence required for removal of the hair follicle by direct ablation will depend on the specific laser system chosen for the task. For ultrashort pulse lasers, for example (pulses shorter than about several tens of picosecond) pulse fluence substantially in the range of 0.1 to 7 J/cm$^2$ should be capable of ablating both the hair shaft itself as well as the soft tissue surrounding it, as well as the HRC layer. A fluence range of about 1.0 J/cm$^2$ to about 4 J/cm$^2$ is preferred. Such ultrashort pulse lasers are, in fact, capable of ablating almost all types of materials and are substantially insensitive to material types. Such ultrashort pulse lasers are capable of creating holes of high aspect ratios and will be ideal for ablative removal of the hair shaft and hair follicle substantially without causing any damage to the surrounding tissue. Such lasers remove about a single micrometer with each pulse and thus a pulse repetition rate of about 1000 pulses per second will be capable of ablatively removing hair shafts and follicle substantially without causing significant collateral damage (although both higher and much lower rates may be desired).

Other lasers may also be used. For example infrared solid-state lasers (for example in the range of 700 nm to about 11 micrometer. For example Er:YAG (2.94 $\mu$m), and Ho:YAG (2.1 $\mu$m), or even CO$_2$ lasers (10.6 $\mu$m,) with pulse duration substantially from about 0.1 ns to about tens of microseconds may be used with variable repetition rates of up to about several 10,000 Hertz, may be used with a per-pulse fluence in the range of 0.5 J/cm$^2$ and up to about 8 J/cm$^2$. A fluence range of about 1.0 J/cm$^2$ to about 4 J/cm$^2$ is preferred.

Infrared solid state laser operating in a normal mode, free-running may also be used for ablative removal of the hair follicles. These lasers consist of longer pulse trains in the range of from about 50 microsecond to about 350 microsecond Such lasers may not be used with high pulse repetition rates since they result in significant thermal energy build up and significant collateral damage. Consequently, these lasers may be used at pulse repetition rates of up to about 3 or 4 Hz without external cooling and up to about 10 to 15 Hz with effective cooling. These lasers remove about 10 to 50 micrometers with each pulse when operated in the fluence range of 5 J/cm$^2$ to 35 J/cm$^2$, with the preferred range of 10 J/cm$^2$ to 20 J/cm$^2$.

In general, other well-absorbed laser may be used for ablative removal of the hair shafts and follicles. Such high absorption is needed in order to confine the interaction to the designated removal zone and limit collateral effects. Thus, for example, far ultraviolet lasers, such as, for example, the Argon-Fluoride Excimer laser (193 nm) may be used with a pulse duration from about several picosecond an up to about several hundred nanoseconds at pulse repetition rates of up to about several thousand pulses per second and fluence in the range of from about 0.2 J/cm$^2$ to about 35 J/cm$^2$ with a preferred range from about 1.0 J/cm$^2$ to about 10 J/cm$^2$.

SIMULTANEOUS MULTIPLE HAIR INTERACTION/LARGE BEAM SPOT-SIZE

Here multiple-hair shafts are illuminated simultaneously. Some of the beam is intercepted by hair-free skin and is reflected by the high reflectance coating according to the practice of the present invention. Accordingly some of the beam is not used for affecting changes in the hair condition and is substantially wasted. Here a large beam diameter size implies a beam spot size that contains at least several hair follicles or a spot greater than about 0.3 cm$^2$ and a diameter (FWHM) greater than about 3 mm. A preferred value for such a large spot size allowing rapid operation on a large area and multiple-hair destruction, is from about 0.6 cm$^2$ to about 1.3 cm$^2$.

One of the obvious consequence of this new geometry is that no ablation embodiment can be used with an embodiment that employs large area beams. In order to maintain the fluence level at each single hair even with this large beam area, the total beam energy must be increased. This means that an exemplary spot size of 1 cm$^2$ will require 10,000 times more total source energy as compared to the small spot size/single hair interactions utilizing a beam spot area of only 100 µm. Additionally, since large beam coupling can be expected to be less efficient, the required total energy output will probably be larger yet.

On the other hand, since an exemplary 10 J/cm$^2$ require only ten joules from the large beam configuration, most exemplary laser sources can easily provide this and much more than that. The highly efficient single hair coupling, however, requires only 1 mJ source to generate the 10 J/cm$^2$ fluence.

The beam converges and lenses used should also be modified to allow for the large beam diameters required. A convergent or collimated beam should be used.

Other beam parameters such as the wavelength and the corresponding absorption and propagation, pulse duration, and optical coupling/index-matching, will remain substantially similar to those discussed in the small-beam/single hair interaction described above.

Finally, it should be emphasized again that the list of Optical field parameters for irreversible hair damage provided above should be considered general guidelines and variation from one embodiment to the other may be required as the specific details of each embodiment vary.

PARAMETERS FOR FORCING A SUBSTANCE INTO HAIR DUCTS

In some embodiments of the present invention, as described below, it may be necessary to force a substance into the hair ducts and down the follicle towards the papilla region. In order to cause a quantity of such a substance to infiltrate the hair ducts and penetrated as deep as possible toward the papilla, several techniques may be employed including, for example, rubbing, massaging, applying higher pressure over the skin surface, and/or applying an ultrasound energy field with frequencies in the range of 3.0 MHZ to 10 MHZ at a power level of about 0.1 to 0.4 watts for 2 to 20 minutes to help force the substance into the hair ducts.

Removing reflective coating in an area of skin proximate each hair to be removed comprises removing reflective coating immediately above the follicle of each hair to be removed, the area of the reflective coating removed being approximately equal to between approximately 0.2 hair diameters and approximately 15 hair diameters.

EXEMPLARY TREATMENT PROTOCOLS

1A. APPLICATION OF A SUBSTANCE OF HIGH REFLECTANCE, HAIR SHAFTS CUTTING, LARGER-DIAMETER BEAM/SINGLE BEAM METHOD

In its most basic form the method according to the practice of the present invention includes the following steps:

a) Skin application of a substance with an index of refraction lower than that of the hair (for example, cream, water or oil, or any type of such lower index of refraction material that is safe and can be effectively introduced to the hair follicles) in such a manner as to cause a quantity of said substance to infiltrate the hair ducts and penetrate as deep as possible toward the papilla. Massaging said substance and/or applying an ultrasound energy field with frequencies in the range of 3.0 to 10 MHZ at a power level of about 0.1 to 0.2 watt with 2 to 20 minutes would help force the substance into the hair ducts.

Additionally, various fluids, vapors, and/or gasses may be used to enhance the transmission of energy through the hair shaft. For example, argon, helium, nitrogen, carbon dioxide and air each have a lower index of refraction than the hair shaft. Thus, the application of any of these substances to the hair follicle will enhance energy transmission through the hair shaft.

Such enhance transmission occurs according to well known physical principles, wherein electromagnetic energy tends to be transmitted through a medium of higher index of refraction when the medium is surrounded by a substance of lower index of refraction.

This step, however, may not always be necessary and may sometimes be omitted. For example, if propagation of the electromagnetic radiation beam down the hair shaft is determined to be sufficient (e.g. if application of such radiation to a test site demonstrates good results), or if the hair's natural pigmentation are such that reduced absorption of light is encountered, and/or if the body's natural oils allow sufficient beam energy propagation.

Also, if optical and/or thermal energy transport down the shaft is determined to be effective, it may be useful to chose a lower index of refraction substance (again, lower than the index of refraction of the hair shafts) which is also an effective thermal insulator. In this case, since the energy is effectively transported down the shaft to the deepest regions of the follicle where hair destruction is most effective, the lower refractive index (LRI) substance with the additional characteristic of low thermal conductivity (LTC), will provide additional protection to the upper skin where important. structures like the sebaceous glands are located and should not be damaged. Suitable substances with a refractive index lower than that of the hair and the skin and with low thermal conductivity might be, for example, fresh animal fats (with thermal conductivity of 0.0017 W/cm/° C.) or other oils or cremes that possess such low thermal conductivity and refractive index lower than that of the hair shafts and skin. A colloidal suspension of dielectric may also be utilized.

Figure 4B:
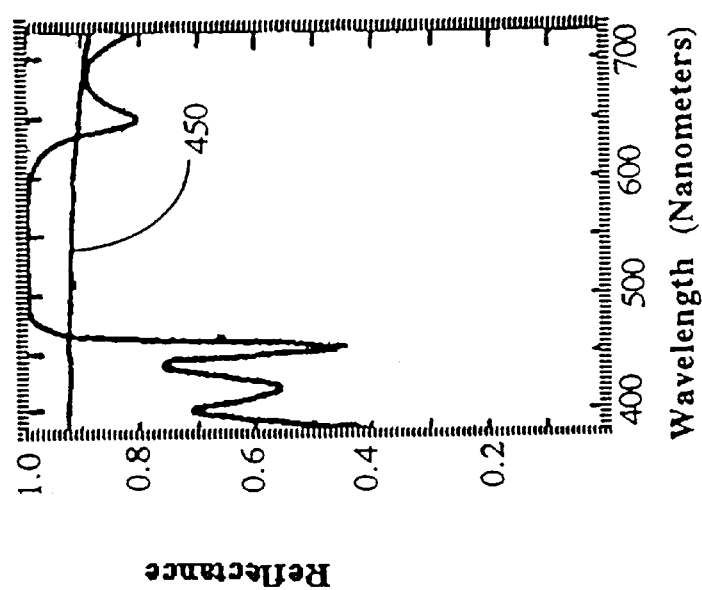
FIG. 4B is a graphical representation of the reflectance of aluminum (which may serve as a component in a substance of high reflectance coefficient) as a function of wavelength.

Since the most efficient penetration of any substance forced into the hair duct (including such lower refractive index/low thermal conductivity substance) will occur in the upper portion of the hair ducts, the low thermal conductance, i.e., insulator, protection to the upper follicle duct walls and the adjacent tissue, will also be most effective in that upper region the region where it is needed most. Lower portions of the duct (towards the hair bulb and papilla region) would receive less lower refractive index/low thermal conductivity substance protection and coating and, thus, greater leakage of light into the targeted, hair-sustaining tissue and efficient transport of heat down the hair follicle and towards the hair-sustaining tissue at the targeted region would follow, resulting in effective destruction of these tissue regions. The targeted hair-sustaining tissue region was described in detail in the background section above.

b) Selection of an electromagnetic radiation source of such a wavelength that substantially mitigates absorption by the melanin 410 (see FIG. 4A) pigmentation in the hair yet enhances absorption in water 430 and in hemoglobin 420. Also, such source wavelength selection should preferably mitigate photon scattering by the melanin in the hair shaft. FIG. 4A shows the region of the electromagnetic spectrum where absorption by melanin is the lowest.

c) Selection of a second substance with substantially very high reflectance, very low transitivity, and very low absorption in the wavelength spectrum of the electromagnetic radiation source selected in step b above to serve as a high reflectance coating (HRC) fluid. Metallic dye may serve as an example of such a substance. FIG. 4B shows the high reflectance of an exemplary aluminum metal 450 and that of an enhanced aluminum metal. As FIG. 4B shows, the aluminum substantially reflects most of the energy impinging on its surface, thus acting as a very effective shield over the wavelength range contemplated by the present invention. Metallic particles of appropriate size (i.e., a particle size properly chosen to avoid infiltrating the skin surface) can be used in suspension as an exemplary substance for high reflectance coating.

d) Ensure that such a substance of high reflectance is capable either by itself, or when dissolved within a host medium, of adhering to the skin surface for the entire treatment period and preferably much longer (for example a period of at least a few hours). Such substance should also not be easily removed from the skin surface. Such substance should also be able to substantially reflect all incident radiation from said electromagnetic source selected in step (b) above and should preferably not be substantially damaged by a beam of up to about $10^9$ W/cm$^2$;

e) Application of the high reflectance substance to the surface of the skin in such a manner as to ensure substantially a complete covering of all segments of the skin surface and of all the entire length of hair shafts above the skin surface and within the targeted area (as was discussed above and illustrated in FIG. 3B);

f) Cut the hair shafts 104 (FIG. 5A) as close as possible to the skin substantially without removing or damaging the layer of high reflectance coating on the skin in the targeted area. The cutting step can be accomplished either manually with a razor 520, with an electrical razor, or any other device capable of cutting the hair shafts close to the skin surface yet not damaging or removing the layer of substance of high reflectance properties. Preferably, the razor is capable of slightly pulling the hair shafts up from the skin 150 and then cutting only the hair shaft, sparing the HRC and the skin.

Figure 5A:
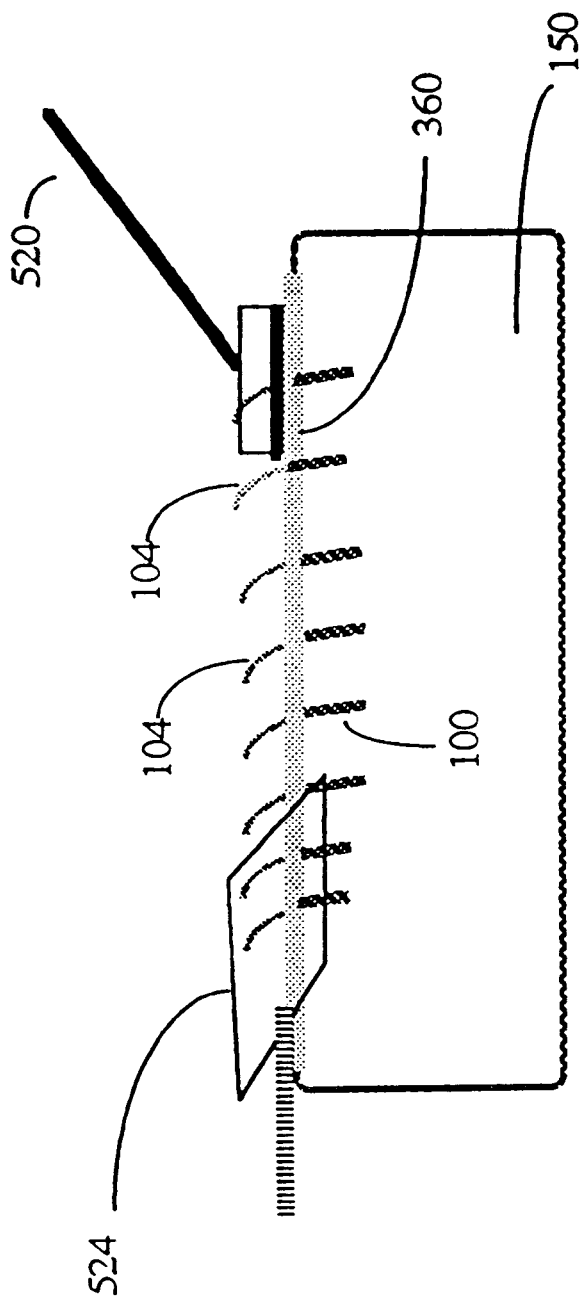
FIG. 5A is a graphical representation of exemplary methods for shaving or removing hair shafts wherein both wax-removal and shaving of hair shafts on the targeted skin area are demonstrated.

As a reference for additional embodiments (to be discussed below), an alternative method for removing the hair from the skin by means of a waxed-stripping 524 is also shown in FIG. 5A. Here, the wax-strip is attached to the hair and then pulled away thus removing the hair shafts with it.

Figure 5B:
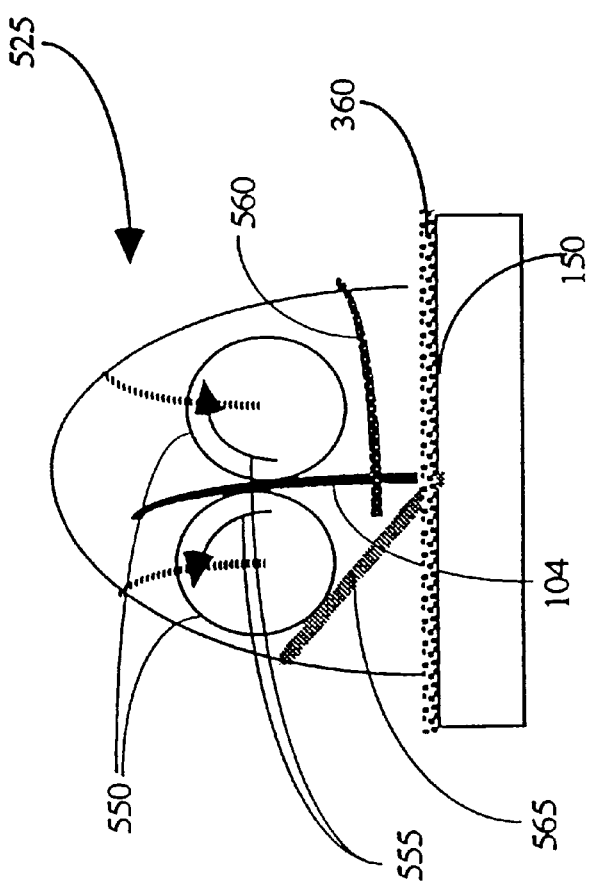
FIG. 5B is a graphical representation of an apparatus and a method for pulling up and shaving the hair shafts substantially without damaging or removing the layer of high reflectance coating on the targeted skin area.

FIG. 5B illustrates an exemplary hair-shaft cutting device 525 capable of cutting the hair 104 very close to the skin surface substantially without damaging the high reflectance coating layer 360. As shown in FIG. 5B, two roller wheels 550 rolls in an opposite sense to each other as indicated by the arrows 555 so that they can grab the hair shafts 104 and pull said hair shafts up and away from the skin surface. A knife 560 is used to cut the hair shafts substantially very close to the skin surface 150 once the hair shafts have been pulled to a sufficient predetermined level, yet without damaging the high reflectance coating 360. The wedge 565 is used to raise the hair shaft from the skin surface and the layer of high reflectance coating and to lead the hair-shaft towards the razor wheels 550.

Figure 6:
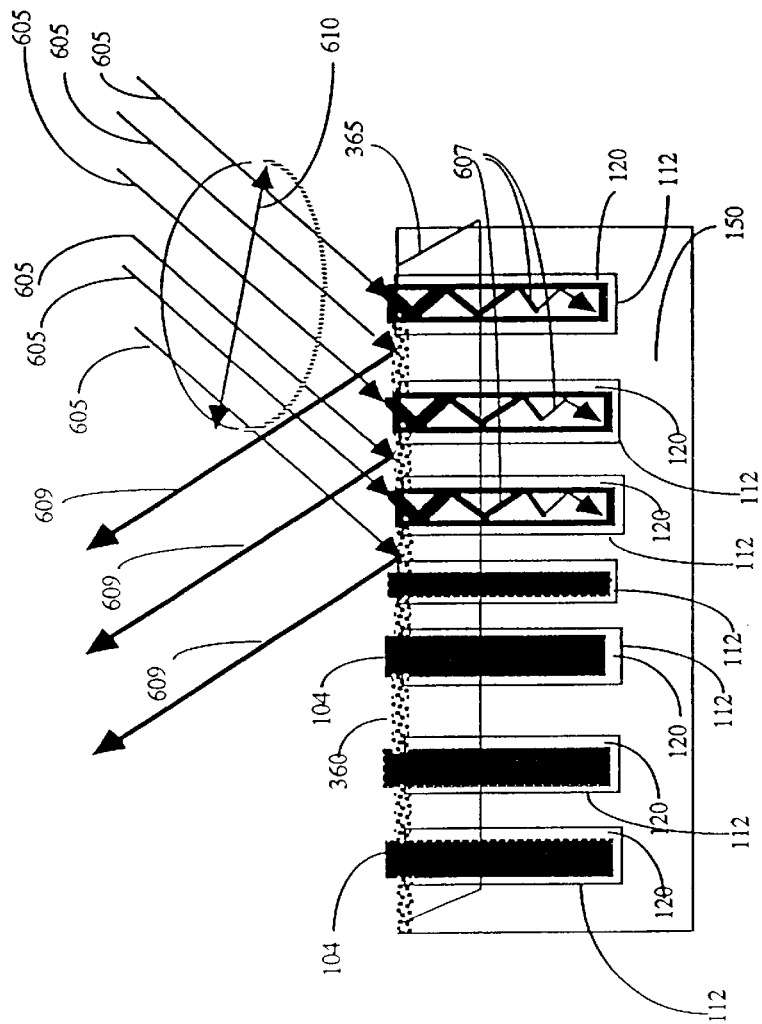
FIG. 6 is a graphical representation of the skin surface and hair shafts after the shaving step, the coupling of light to the shaved hair shafts, and the reflection of light from the regions on the skin surface coated with a layer of a substance of high reflectance wherein a large area beam is illustrated.
Figure 7B:
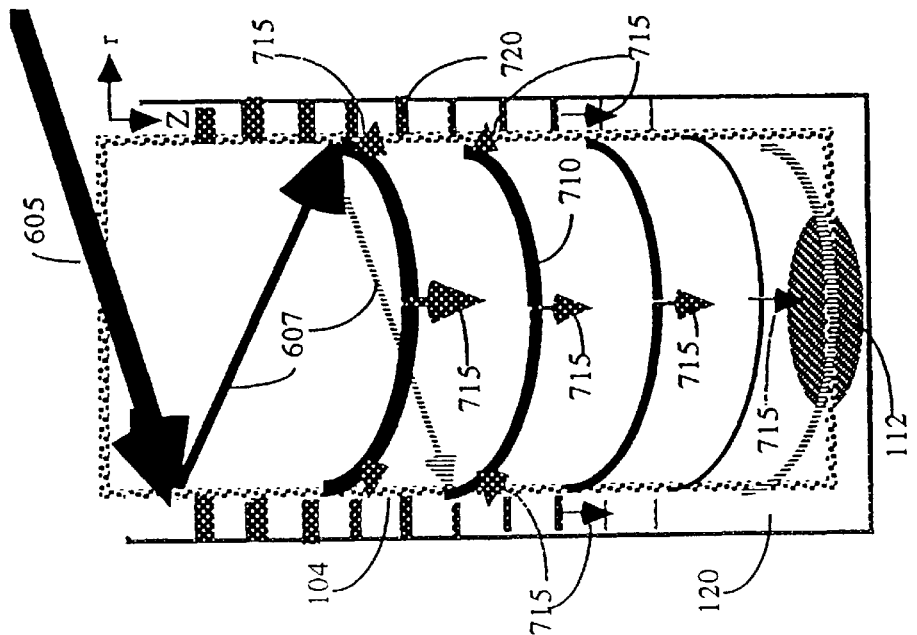
FIG. 7B is a graphical representation of coupling, propagation, gradual absorption and heat diffusion in the hair shaft and hair ducts.
Figure 7A:
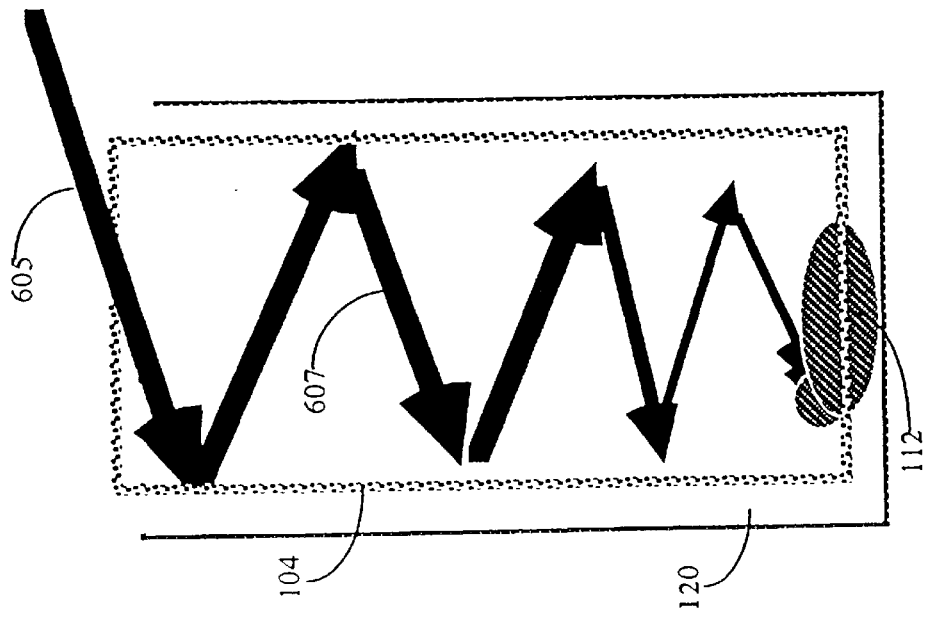
FIG. 7A is a graphical representation of exemplary coupling, propagation, and absorption of light in a hair shaft.

FIG. 5C shows the top view and FIG. 5D shows the side view of the cut hair shafts 104 and the skin 150. While the entire skin surface and the exposed, external surface of the hair shaft walls 510 are covered with high reflectance coating 360, the cut hair shafts openings 514 (i.e., the surface perpendicular to the hair shaft walls created by the cutting action) are not covered with the high reflectance coating 360.

g) Referring now to FIG. 6, focus of the source's electromagnetic radiation beam 605 to a relatively large-diameter spot 610 (i.e., a spot large enough to encompass multiple hair shafts) within the targeted area 365 of the high reflectance coating-covered skin. The area illuminated by the beam should contain multiple cut hair shafts 104. Such large-beam diameter 610 should be in the range of about 0.3 cm to about 10 cm, preferably about 1 cm.

h) As show in FIG. 6, illumination of the targeted section of skin with the incoming large diameter beam of spot size 610 comprised of the electromagnetic radiation frequency band that was selected in step b above, so that some of the incoming radiation 605 is coupled to the uncoated opening of at least several hair shafts 104 created by the cutting step, and becomes coupled radiation 607. At least a portion of said coupled radiation 607 is absorbed in the hair shafts and follicles and a portion of said coupled radiation 607 propagates down the hair shafts 104 and hair follicles 100 to the hair bulbs 102 and papillae 112, so that the energy absorbed in these targeted components is sufficient to cause a reaction that destroys said multiple hair by causing death of hair follicles and/or of the skin tissue and blood vessels feeding the hair follicles. The portion of the incoming radiation 605 that does not intercept the shaved hair shaft is, instead, substantially reflected by the high reflectance coating layer 360 on the skin surface and becomes the reflected beam 609. The reflected beam can be used, for example, to monitor the progress and safety of the procedure. For example, an unusual drop in the reflected intensity may indicate damage to the high reflectance coating layer. An unusual increase in the reflected intensity may indicate ineffective coupling or improper cutting.

i) Referring now to FIGS. 7A and 7B, the interactions leading to the death of the hair follicles is brought about (FIG. 7) either through the direct deposition of optical energy in the hair follicles and the subsequent destruction of tissue sustaining the hair, or, due to additional energy transfer brought about by the thermal conduction of the heat from the regions of direct electromagnetic energy deposition to adjacent tissue regions. Both mechanisms of delivering the depilating energy to the hair-sustaining tissue may play an important role in the destruction of the hair follicles. Ultimately, however, both the tissue and the beam characteristics determine how much of the incoming radiation can directly propagate through the hair follicle and how much of the incoming radiation energy will be thermally conducted to the adjacent tissue region.

The role of each one of the two mechanisms for energy deposition can be better understood with the aid of FIGS. 7A and 7B. In this figure, the incoming electromagnetic radiation 605 is coupled and propagates down the hair shaft 104 where it is gradually absorbed. The gradual absorption of the propagating radiation 607 is indicated by the diminishing thickness of the arrowhead-lines 607 which represent this propagating radiation.

In FIG. 7A, which depicts deep optical penetration, the light is coupled to the hair shaft and then propagates down along the shaft until at least a portion of the incident beam arrives at the papilla region 112. Note that the incoming beam is continuously absorbed as it propagates down the hair shaft and the amount of light reaching deeper regions of the hair follicle is continuously diminished. Again, this is indicated by the diminished thickness of the arrows 607 representing the propagating beam.

FIG. 7B, depicts highly absorbing hair shaft conditions where the light is absorbed rapidly by the upper component of the hair follicle. This is indicated by the vanishing of the arrows representing the coupled beam 607 within the upper half portion of the hair shaft. In this case, the coupled electromagnetic radiation 607 is converted into thermal energy 710 in the hair duct. This thermal energy 710, in turn, diffuses both down the hair shafts (as indicated by the arrows 715 attached to the lines 710) and into the hair ducts, and subsequently, into adjacent skin components leading to an irreversible damage to the hair-sustaining skin components and leading to the removal of the unwanted hair. The diminishing thickness of the lines 710 representing heat in the hair shafts, and heat in the hair ducts 720, corresponds to the initial density of thermal energy. It is this gradient in thermal energy concentration (which, in turn, corresponds to a temperature gradient) that leads to the heat flow in the direction of the arrows 715.

j. To improve the efficiency of the coupling of the incident beam into the hair shaft and hair follicles, the orientation of the hair with respect to the skin surface can be determined and the large-area beam angle of incidence can be oriented to match the hair angle so that optimal coupling is achieved. Orientation can be determined either manually through operator inspection of the hair (prior to hair shafts cutting) and manual orientation the incident beam so it matches the angle of the hair, or through an automated pre-scan step whereby a very low power (e.g. 1 mW) interrogating beam scans the targeted skin surface and determines the orientation of the shaved shaft opening by means of locating the orientation for minimum back scattering as was described in pre-operative steps as discussed above and shown in FIG. 3A. Once the orientation of the hair (and the orientation of the hair shaft shaved opening) has been determined, the angle of incidence of the large-area beam is varied during irradiation about the polar angle of incidence $\theta$ by up to about $\pm 35°$, and by up to about $\pm 45°$ about the azimuthal angle $\phi$, in order to ensure optimal coupling to all hairs that might deviate from the generally observed hair orientation.

1B. COATING OF THE SKIN SURFACE WITH A SUBSTANCE OF HIGH REFLECTANCE, CUTTING OF THE HAIR COATED SHAFTS, LARGER-DIAMETER/SINGLE BEAM METHOD WITH THE INSERTION OF A SUBSTANCE OF LOW THERMAL CONDUCTIVITY (AN INSULATOR) INTO THE HAIR DUCTS

This embodiment is substantially the same as that of Embodiment 1A, except that in step (a), the substance of the lower index of refraction is also chosen so that it also possess low thermal conductivity characteristics. Forcing a substance of low thermal conductivity into the upper hair duct will serve to confine the generated heat to the hair shaft and allow said heat to diffuse substantially downward (in the Z-direction as indicated in FIG. 7B) towards the skin components sustaining the hair and targeted for destruction. The thermally insulating substance may, for example, consist of animal fat or oils (with thermal conductivity of 0.0017 W/cm/° C.) or creams rubbed or forced into the hair ducts. As was mentioned above, forcing any substance down the hair ducts 120 will result in a greater concentration in the upper portion of ducts due to the greater difficulty in forcing the material all the way down to the vicinity of the papilla. This is beneficial since a higher concentration of the low conductance substance (substantially an insulator) results in a higher concentration in the upper portion of the ducts and will serve to prevent excess damage to the upper follicle, epidermis and sebaceous glands, while confining heat to the ducts and enhancing thermal energy conduction in the Z-direction (see FIG. 7B) toward lower follicle region and papilla.

2A. APPLICATION OF HIGH REFLECTANCE COATING AND HAIR SHAFTS CUTTING, SMALL BEAM DIAMETER/SINGLE BEAM, SINGLE-SCAN METHOD

Figure 8A:
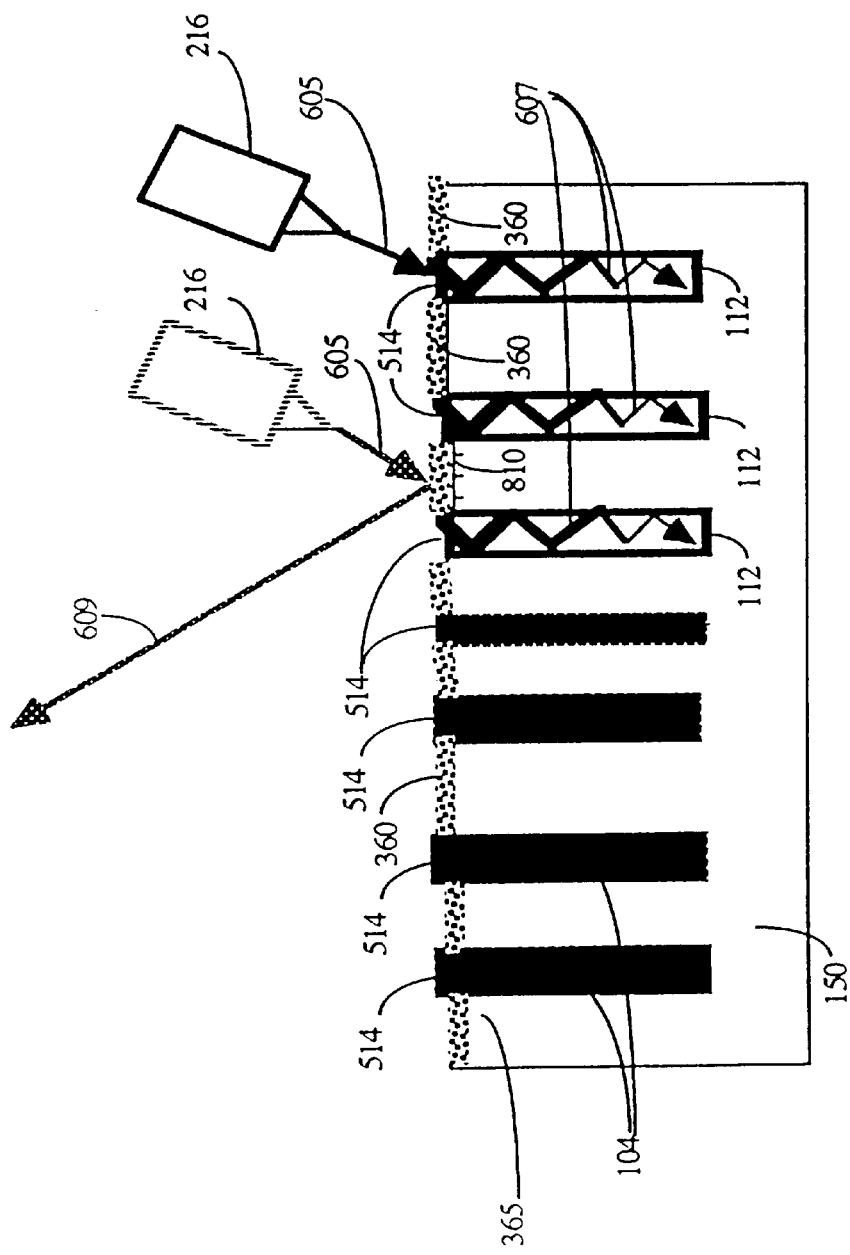
FIG. 8A is a graphical representation of the skin surface and hair after shaving illustrating the coupling of light to the shaved hair shafts and the reflection from the high reflectance surface wherein small beam spot-size/single-hair coupling is illustrated.

This embodiment is essentially the same as the one described by embodiment 1, above, except that instead of a large area beam, a small spot size beam is used so that the source beam output 605 is coupled substantially into only a single hair shaft and the beam interacts with one hair at a time (see FIG. 8A). The advantage of this single hair/focused beam embodiment is that the light can be more efficiently coupled into the hair fiber. A more efficient energy coupling, in turn, translates into an enhanced energy transmission and deposition within the hair follicle and a more efficient destruction of the hair. Thus, the beam dwell time over each hair is shorter and the beam can be scanned rapidly over an area equivalent in size to that of the large-area beams of embodiments 1A and 1B, and allows multiple-hair destruction in a treatment time substantially equivalent to that of the large-area beam of method 1.

Normally, such single-hair coupling embodiment would imply considerable lengthening of the treatment time—a disadvantage. In the present invention, however, the combination of the steps including the application of a high reflectance coating layer to the skin, followed by the cutting of the hair shafts allows for a method of a very rapid target (i.e., the hair) recognition, very rapid scanning, and considerably shortened treatment time. This concept will now be made clear by the following discussion and with the aid of FIGS. 8A, 8B and FIG. 9.

In this preferred embodiment the incident beam 605 is focused to a spot size smaller than the hair shaft diameter (for example, smaller than about 60 $\mu$m) by a lens whose numerical aperture (NA number) matches that of the hair shaft (for example, an f/1.5 fiber lens located approximately 3.5 mm from the hair opening should result in satisfactory coupling of light to the hair shaft). The depilatory beam is then turned on with a beam parameters' settings and dwell time that are sufficient for permanent hair destruction as discussed above. When the targeted hair has been destroyed, the beam (emerging out of the treatment/scanning head 216) is scanned across the targeted surface 365 so it covers the entire 2-dimensional extent of the targeted area. Subsequently, when the incident beam 605 is moved away from a cut hair shaft opening 514 and is aimed at a region covered by the high reflectance coating 360, i.e., any portion of the targeted surface 365 except for the cut hair shaft opening 514, it will be substantially harmlessly reflected 609. However, when the beam 605 is intercepted by an exposed, cut, hair shaft opening 514, it will be effectively coupled 607 and absorbed by the non-coated hair surface (although some reflection can always be expected from a surface of at least some degree of mismatching in refractive index). The light thus coupled 607 to the exposed opening in the hair shaft will be both transmitted and gradually absorbed by the hair shaft 104 and its surrounding tissue components as it propagates down the hair follicle towards the hair bulb and papilla 112. This propagation and absorption in the hair shaft 104 is indicated by the diminishing thickness of the line 607 representing the hair-coupled light.

Significantly, it is also possible to use this single beam scan configuration in a two-intensity-level mode which eliminates the unnecessary irradiation of the hair-free region of the skin. In this embodiment, the incident beam 605 is idling at a low intensity level (for example at a low average power level of about 1.0 mW) when it is not aimed at a hair shaft but rather at a hair-free surface 810 of FIG. 8A. A large area detector collects the reflected light in a manner similar to the method described below in embodiment 2B and illustrated in FIG. 8 and FIG. 9. When the reflected light intensity level drops (indicating a relatively higher absorption/reduced reflection due to the presence of a cut hair shaft), it implies that the beam 605 has intercepted an exposed, cut hair shaft. A feedback loop rapidly and automatically increases the power of the incident beam 605 to a higher depilatory level as described above for a given time duration and allows destruction of the hair follicle. Depending on the required kill-time (i.e., the exposure time required to bring about an irreversible damage and destruction to the hair) the scanning/treatment head motion can be interrupted to allow enough dwell time over the hair follicle to allow complete destruction of the hair. Indeed, any of the scanning detection methods described in embodiment 2B below can also be used with this single beam/two-power levels method just described.

2B. APPLICATION OF HIGH REFLECTANCE COATING AND HAIR SHAFTS CUTTING, SMALL BEAM DIAMETER/DUAL-BEAMS, SINGLE OR DUAL SCAN METHOD

This embodiment is essentially the same as the one described by embodiment 2A above, except that instead of a single small spot size, interrogating/depilatory beam which is constantly on during treatment and scanning, two beams are used (FIG. 8B): The first (interrogating) beam is generated by a low power laser 244 (e.g., 1 mW continuous wave diode laser) which generate a low power beam 860 (delivered, for example, through an optical fiber). This beam 860 is used to scan the surface and identify the targeted hair shaft openings 514. The second, a much more powerful depilatory beam 870 (which may also be delivered through an optical fiber of other optical delivery means), is of sufficient power density to bring about the death of the hair as specified above. The depilatory beam 870 is generated by a substantially more powerful laser 872, and is not activated except for specified times once the targeted hair follicles have been identified by the interrogating and the depilatory beam is aimed at a targeted hair shaft opening 514. When such identification and alignment have been achieved, the depilatory beam 870 is turned on to bring about irreversible damage and destruction of the hair.

Figure 8B:
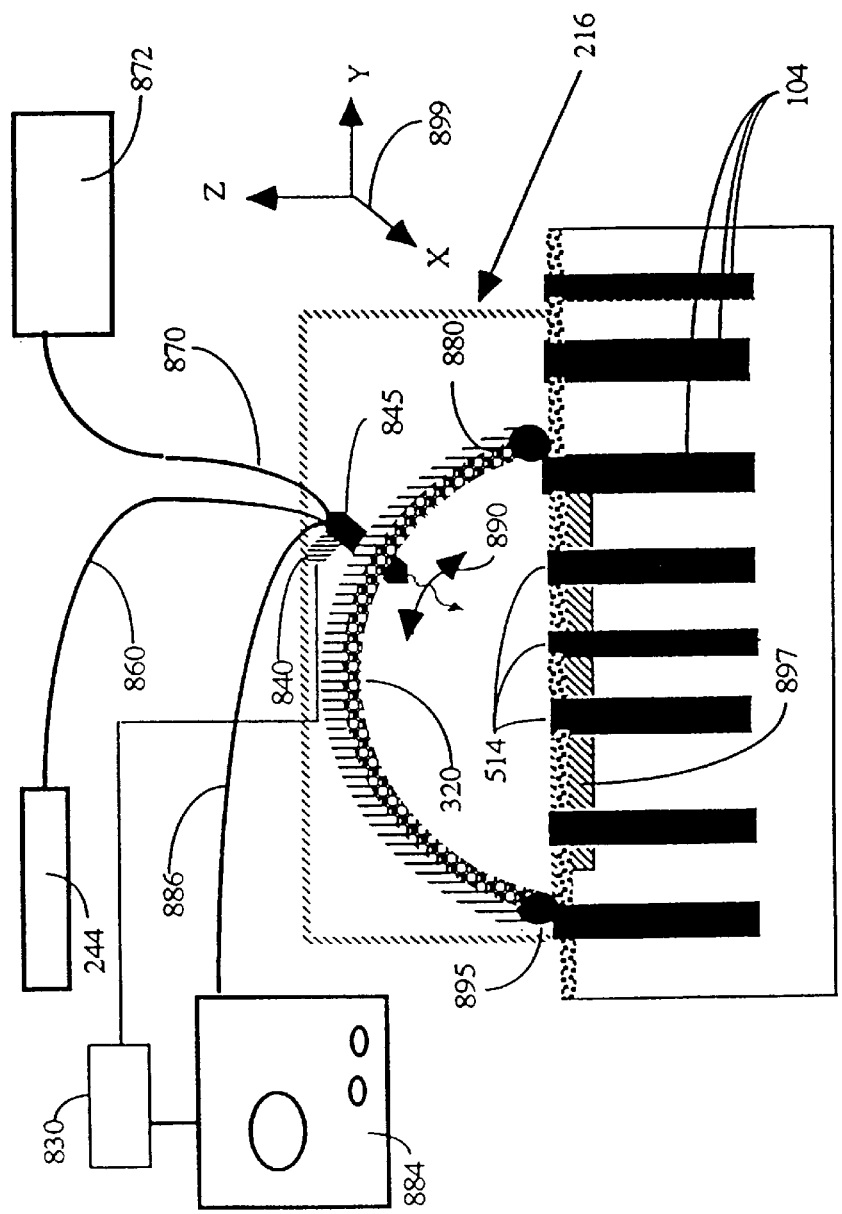
FIG. 8B is a graphical representation of an exemplary, scanning/treatment (S/T) head and related components for a hair modification and removal apparatus according to the practice of the invention.

Referring now to FIG. 8B, this embodiment comprises the following steps:

a. Interrogating Beam: A weak (for example a 1 mW, 670 nm, CW beam 860 from an exemplary laser diode, or Helium-Neon (He—Ne) 244 laser beam at 633 nm, is focused to a spot size substantially smaller than the hair shaft diameter and is rapidly scanned over the targeted treatment area. The beam reflected intensity profile is monitored by a large optical collection/detection area 880 optical detector whose output is connected to a computer 884. The computer records the reflected output intensity profile. A simple software in the system control-unit/computer 884 can identify and record the location of minimum reflected intensity which correspond to the exposed cut hair locations (which are now the only uncoated locations on the skin). The computer software also controls a driver 830 and means 840 for controlling the motion of the weak scanning beam as well as the treatment/depilating beam (for example a stepping motor or piezoelectric translator may be used). The two beams may be made collinear inside the output assembly 845.

b. When the scanning of the targeted area is completed (for example an area of 1 $cm^2$ may be scanned), the computer may direct the output assembly 845 towards the identified hair shaft locations.

c. The depilatory beam: This beam is focused to a small spot size substantially in the range from about 5 $\mu$m to about 60 $\mu$m with the optical parameters required to generate irreversible damage to the hair-sustaining tissue as described above. The depilatory beam is not activated when the scanning-treatment head is interrogating the surface. Only upon receiving a signal from the computer indicating that the location of a cut hair shaft has been reached is the depilatory beam activated. At this point the energy of the activated depilatory beam is coupled to the hair shaft and the interaction of the depilatory beam with the hair follicle and its surrounding tissue bring about death of that particular hair follicle. The scanning/treatment head is then moved to a next hair shaft location where the process is repeated.

d. The entire scanning/treatment head apparatus rests on supports 895 and covers the targeted skin subsection 897. The scanning/treatment head is stationary during the treatment of any given subsection 897 of the targeted skin area. The scanning motion is accomplished by either scanning the output beams or moving the output beam assembly 845 in any desired direction (including in and out of the plane of the figure and in the direction indicated by the arrows 890), so that the beams are moved along the skin two-dimensional surface. (The plane of the skin surface is the x-y plane shown by coordinate arrows 899.) Once treatment of the area 897 is completed, the entire scanning/treatment head apparatus 216 is moved to a new location for continuation of the treatment. The treatment continues until the entire area of unwanted hair has been treated.

Advantages of the present embodiment include the fact that the hair-free skin is not even exposed to the high power epilating beam thus increasing the safety and efficiency of the method. In addition, the epilating beam can now utilize more of the source energy since energy is not wasted on useless reflection from off-target HRC-covered skin, and finally, higher fluence can be utilized since substantially no irradiation of non-hair shaft region occurs. The light being turned off during non-shaft location of irradiation thus eliminates excess energy usage, unnecessary irradiation of the non-target surface area, and possible undesired effects and chances for mistakes.

It is also possible to use the interrogating/ablating phases simultaneously rather then in sequence as described above. In this embodiment, an interrogating beam is still used to identify the non-coated, cut hair shafts as described above, however, instead of completing the entire surface scan, the scanning/treatment head is stopped once a hair shaft has been identified and epilating beam is activated and deployed to accomplish destruction of the hair follicle as described above.

Figure 9A:
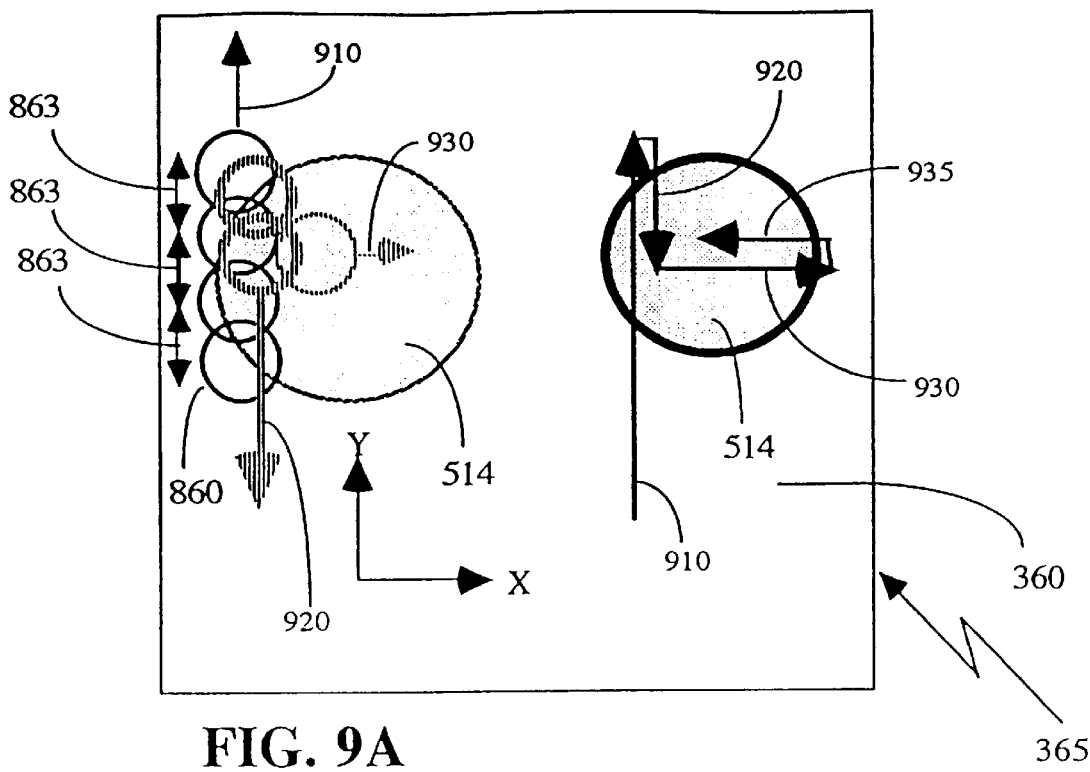
FIG. 9A is graphical representation of an exemplary scanning method for locating hair shaft positions.

Finally, to improve the precision and accuracy of the hair-shaft locating procedure, the apparatus described below and further illustrated in FIG. 8B, FIG. 9A, and FIG. 9B can be used. This apparatus can be used in several of the embodiments of the present invention including embodiment 2A above.

The apparatus make use of the hair shaft-locating step described above, which, again, proceeds by monitoring the total reflection of the interrogating beam from the coated surface skin with the detector as shown in FIG. 8B. An enlarged view of a section of the skin area 365 is shown in FIG. 9A and 9B with an exemplary cut hair shaft opening 514, and the exemplary interrogating beam 860. An exemplary detector 880 as shown in FIG. 8B collects the total reflected light and transfers the signal for analysis. A proper selection of (a) ratio of interrogating beam spot size to that of the hair shaft diameter, and (b) the sequential interval step 863 with which the center of the beam 860 is moved, will yield a reasonably fast scanning rate for a practical system and a practical treatment time. An exemplary interrogating path may look similar to the illustration of FIG. 9 and is described below.

Consider an interrogating beam 860 heading in the original scan direction 910. The total reflected interrogating beam intensity should remain substantially constant while the beam scan the HRC surface. However, a drop in the total reflected intensity (TRI) due to absorption by and coupling to an encountered cut hair-shaft 514, should be easily detected. The computer/control unit 884 directs the scan to continue only until the TRI begins to rise again. At that point the computer/control unit reverses the interrogating beam direction 920 and returns the beam back to the location of minimum TRI. At that point the computer directs a smaller scale scan (for example, approximately less than 100 μm long) along the direction perpendicular to its original direction of propagation 930 until the TRI begins to rise again. A stripped-down graphical representation of the above scanning pattern is also shown in FIG. 9A and the scan pattern corresponding to the interrogating beam 860 motion is shown by the arrows 910, 920, 930 and 935.

Figure 9B:
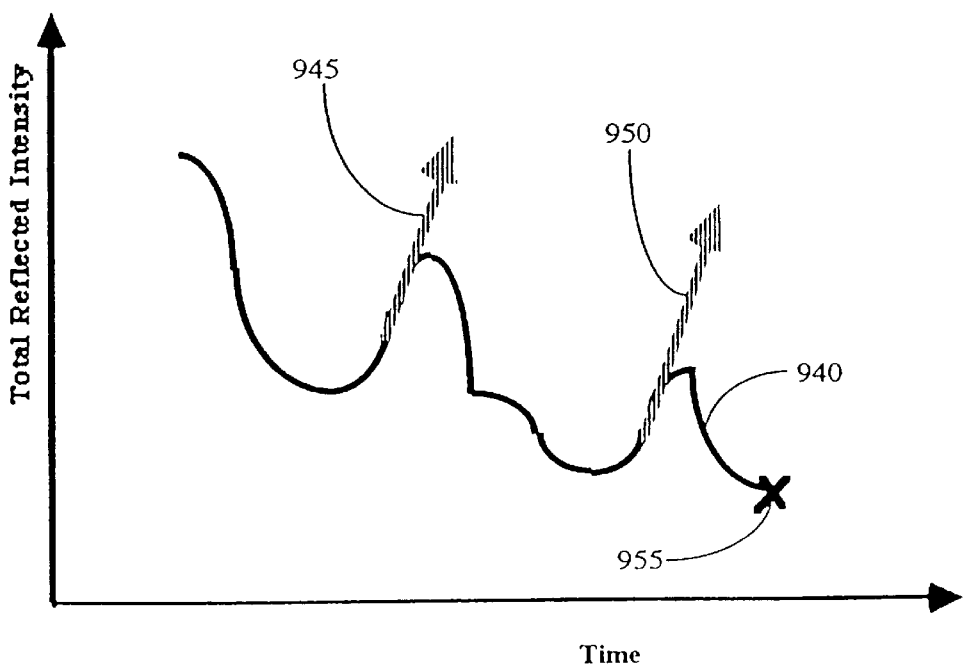
FIG. 9B is a graph showing total reflected intensity versus time for light reflected from skin and hair.

In FIG. 9B the time-dependent total reflected intensity as measured by the large area optical detector 880 is shown. The curve 940 of FIG. 9B corresponds to the path of the interrogating beam 860. The arrow 945 corresponds to a continuing increase in total reflected intensity (TRI) had the path 910 not been reversed (in search of the TRI minimum). Instead, the original direction of the beam 860 (FIG. 9A) is reversed and the direction 920 is taken. The TRI thus drops while the beam is returned to the position of minimum TRI along this Y-direction of scanning (see X-Y arrows in FIG. 9A). At this point the beam direction is changed again and it follows the arrow 930 (along the perpendicular X-direction) until a minimum is passed and TRI begins to rise again as indicated by the arrow 950 in FIG. 9B. Here, again, the interrogating beam 860 scan direction is reversed once more and follows the -X-direction 935, to substantially to the absolute minimum in total reflected intensity, position 955 indicated by the cross in FIG. 9B. This position substantially corresponds to the center of the cut hair shaft opening 514.

At this point either the location of the cut hair shaft 514 is recorded for later treatment by the depilatory beam, or the depilatory beam is immediately activated and the hair and hair follicle are destroyed as described previously.

Note that even if inaccuracies in position accidentally occur, the depilatory beam light is substantially reflected by most of the skin covered by HRC, and is absorbed substantially only by the cut opening of the hair shaft in the beam path.

Depilatory beam is activated according to the parameters specified above and the beam is coupled to the hair shafts and propagates longitudinally along the hair shafts until it reaches the hair bulb and papilla region. The incident energy is absorbed by the hair and follicle components thus leading to the destruction of the tissue and blood vessels sustaining the hair, thereby killing the hair.

3A. REMOVAL OF PIGMENTATION FROM HAIR SHAFTS, APPLICATION OF HIGH REFLECTANCE COATING AND HAIR SHAFTS CUTTING, LARGER-DIAMETER/SINGLE BEAM METHOD.

Figure 10:
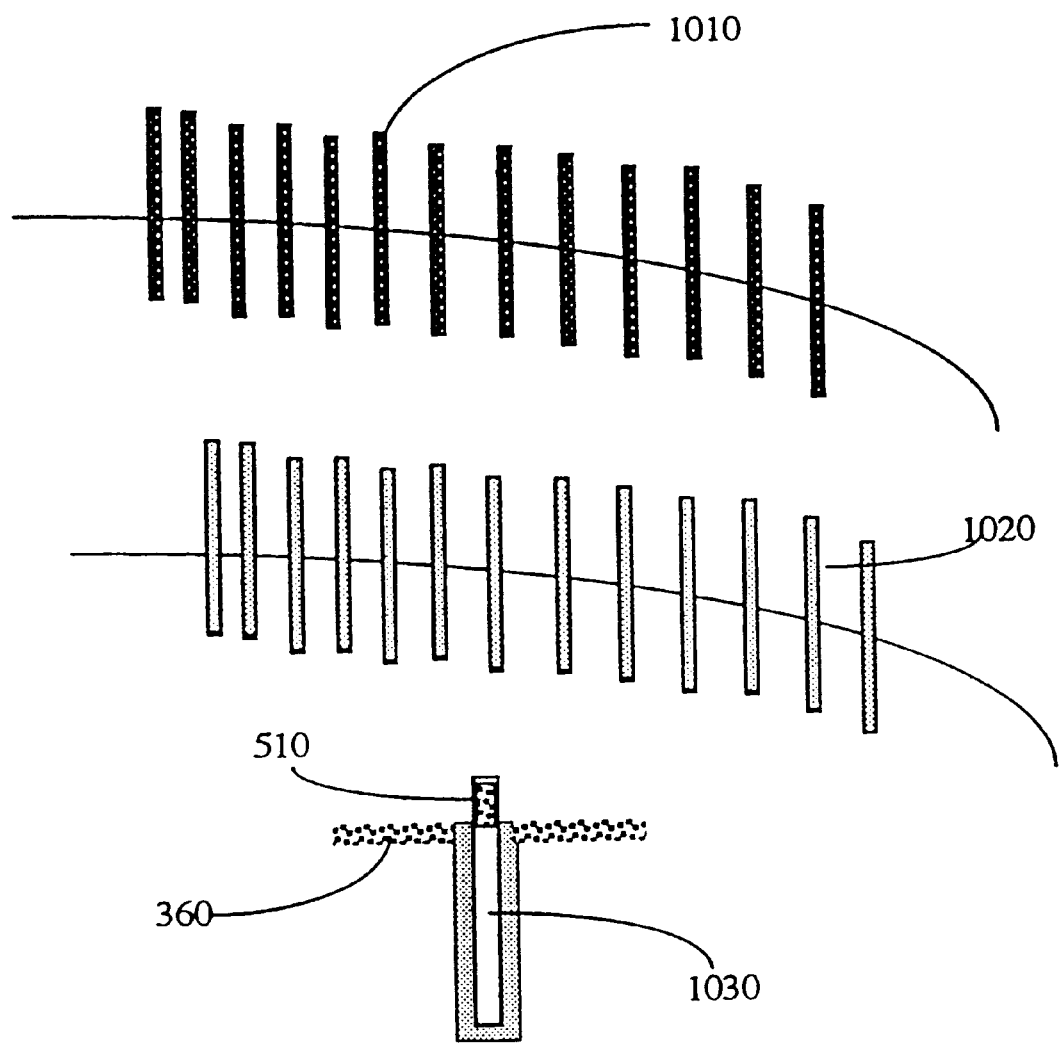
FIG. 10 is a graphical representation of the process of hair shafts bleaching for reduction of hair shaft pigmentation, followed by shaving of the hair shafts.

Referring now to FIG. 10, this embodiment is essentially the same as the one described by embodiment 1A and 1B, above except that the skin Preparation step is expanded to include the a step towards removal of pigmentation from the hair shafts to eliminate as much of the hair melanin pigmentation as possible and to mitigate absorption of the incident electromagnetic radiation as it propagates down the hair shafts. This embodiment is illustrated in FIG. 10.

According to some aspects of the present invention the hair shaft may serve as a waveguide to electromagnetic energy. In particular, the hair shaft serves as a lossy optical-fiber where much of the loss in the propagating beam 607 may occur due to absorption by melanin in the cortex portion of the hair shaft, or due to leakage of propagating energy out of the cortex. Indeed, blond hair shafts and red hair shafts absorb less of the propagating light than black or brown color hair shafts.

To mitigate these losses and enhance transmission of electromagnetic energy down the hair shaft and into tissue components that feed and sustain the hair, the present invention offer several remedies. The insertion of fluid with optical index of refraction lower than that of the hair shaft (i.e., lower than about 1.55 to about 1.6) into the hair ducts, should mitigate leakage out of the hair shaft and will be discussed below. In the present embodiment, at least some removal of hair pigmentation during the skin preparation step is desired. Such melanin pigmentation removal can be accomplished by conventional hair-discoloration techniques familiar to those skilled in the art. For example the use of hydrogen peroxide can accomplish the elimination of pigmentation.

FIG. 10 shows a natural-colored hair 1010 which is then subjected to chemical or physical (laser or light bleaching may be possible too) means so that substantially much of the hair's natural pigmentation is removed 1020. After bleaching, a high reflectance coating 360 is applied over the skin and the discolored hair shaft 1020. The next step is to cut the bleached hair shafts 1030 which are then ready for exposure to the depilatory beam in accordance with the methods of embodiments 1A and 1B. Only the upper portion of the bleached and cut hair shaft 510 (near to or above the skin surface) is covered with HRC.

3B. REMOVAL OF PIGMENTATION FROM HAIR SHAFTS, APPLICATION OF HIGH REFLECTANCE COATING FOLLOWED BY HAIR SHAFTS CUTTING, SMALL BEAM DIAMETER METHOD.

This embodiment is essentially the same as the one described by embodiments 2A and 2B above (i.e., utilizing the small-area beams focused for destruction of a single hair at a time in combination with the rapid, large-area scanning) except that the skin preparation step includes bleaching the hairs to eliminate as much of the hair melanin pigmentation as possible and to mitigate absorption of electromagnetic radiation propagating in the hair shafts. The preparation and advantages of the pigmentation removal step were described above in embodiment 3 and illustrated in FIG. 10.

4. REMOVAL OF PIGMENTATION FROM HAIR SHAFTS, APPLICATION OF A SUBSTANCE OF HIGH REFLECTANCE PROPERTIES TO BOTH THE SKIN SURFACE AND HAIR DUCTS, HAIR SHAFTS CUTTING, LARGER BEAM DIAMETER/SINGLE BEAM METHOD OR SMALLER BEAM DIAMETER METHOD.

This embodiment is essentially the same as that described by embodiments 3A and 3B except that the step of applying high reflectance coating to the skin surface must also include forcing a substance of high reflectance properties into the hair ducts. The combination of beaching of the hair is intended to mitigate light absorption and enhance beam propagation down the hair shaft. Forcing HRC down the hair duct creates a high reflectance layer around the hair shaft and also enhances the waveguide capabilities of the hair shafts.

The steps taken in the practice of this embodiment are essentially identical to those of Embodiments 3A and 3B except that the step of applying high reflectance coating to the skin surface, also include forcing this substance into the hair ducts (for example through the use of massaging, application of an ultrasound field, or any other means) to achieve the forcing of HRC into the hair ducts.

5. APPLICATION OF A SUBSTANCE OF HIGH REFLECTANCE PROPERTIES TO THE SKIN SURFACE FOLLOWED BY PULLING OF THE HAIR SHAFTS OUT OF THE SKIN, LARGER-AREA/SINGLE BEAM METHOD.

This embodiment is essentially the same as the one described by embodiments 1A and 1B, except that the hair cutting step is replaced by pulling the hair shafts out of the follicles (for example through wax-depilation). In this present embodiment, after the application of HRC to the targeted skin, the hair is wax-stripped substantially without removing or damaging HRC.

Figure 11A:
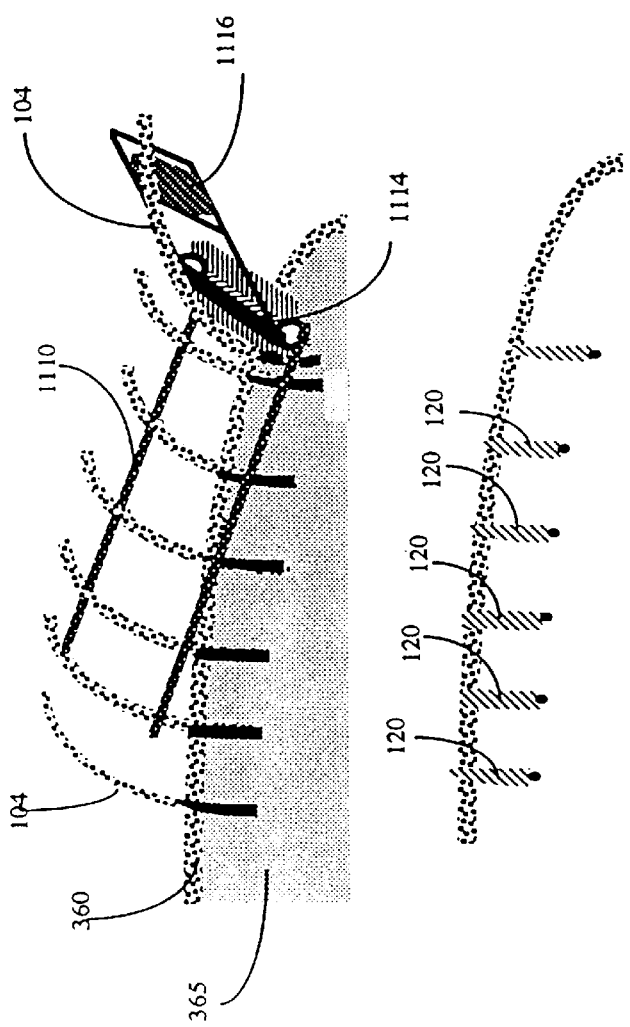
FIG. 11A is a graphical representation of an exemplary apparatus and a method for pulling out hair shafts from a skin surface coated with a substance of a high reflectance substantially without damaging or removing the high reflectance coating from the hair-free skin surface.

This can be accomplished, for example, by the exemplary apparatus illustrated in FIG. 11A, although many other systems to accomplish the same task can be envisioned.

The targeted skin area 365 and hair shafts 103 are coated with HRC 360. A fine comb-like instrument 1110 is used to lift the HRC-covered hair off the skin surface where a dispenser 1114, located on the comb dispenses wax-covered tape 1116 to which the hair shafts 104 are attached. The wax-tape is then cut from the dispenser and pulled away from the skin surface removing the hair shafts 104 with it, and leaving behind the emptied hair ducts 120 (as shown in the lower part of the FIG. 11A).

Because the hair shafts are pulled only after the high reflectance coating was applied (and no attempt to force the HRC into the hair duct is made), the hair ducts 120 are not filled or covered with high reflectance coating or any other substance.

Figure 11B:
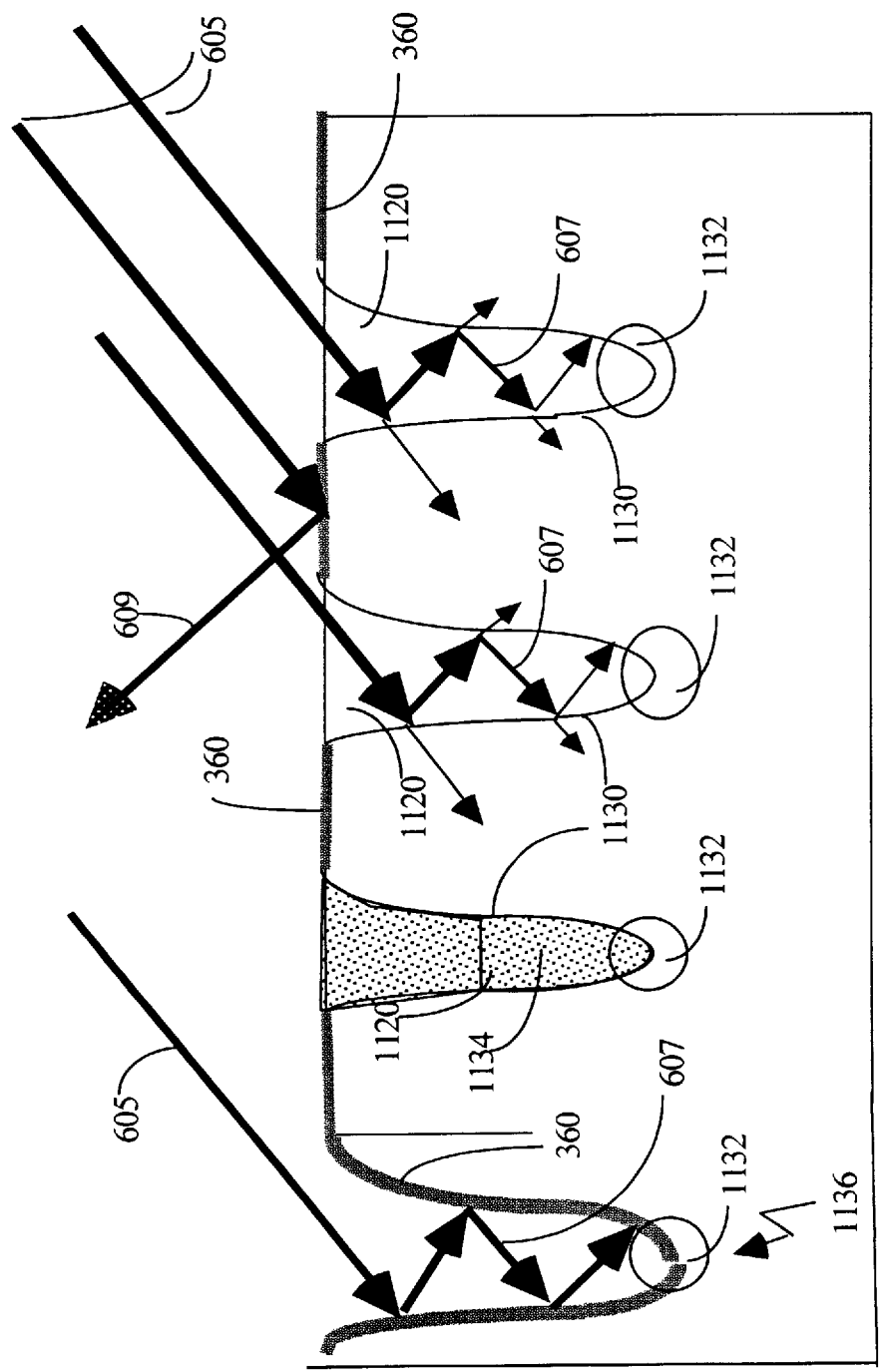
FIG. 11B is a graphical representation of the emptied hair ducts following the process of pulling out the hair shafts and also depicts light coupling to the hair ducts, light leakage through the duct walls and near total light reflection at the skin surface covered with a layer of a substance of high reflectance.

Once the hair shafts have been pulled out of the targeted skin area, as FIG. 11B shows, the incoming beam 605 is then aimed at the targeted area of the high reflectance coating covered skin 365 containing multiple emptied hair shafts 1120. These emptied hair shafts 1120 are now the only segments of the skin surface that are not covered with high reflectance coating.

The incident beam 605 is reflected 609 by most of the skin surface and coupled 607 substantially only to the now exposed and emptied hair follicle. The light rays 607 that are coupled to the emptied hair shafts then propagate down along the emptied follicle until they can be absorbed by either the emptied hair duct walls 1130 or by the hair bulb and papilla region 1132, thereby destroying the tissue and blood vessels sustaining the hair. As it propagates down the emptied hair duct, the coupled beam 607 is partly absorbed and partly reflected by the hair duct walls 1130. The portion of the beam energy absorbed by the hair ducts walls 1130 heats up and irreversibly damage the follicular tissue thereby also aiding in the destruction of the tissue sustaining the hair.

Also, in the practice of this embodiment, (and unlike Embodiments 1A and 1B and Embodiments 2A and 2B) the application of a substance with an index of refraction which is lower than the index of refraction of the hair shaft itself or that of the skin (i.e., lower than 1.55.–1.6), is generally not necessary. In fact, the application of a substance with refractive index higher than that of the skin may be useful to enhance the optical fiber-like conduction of the follicle after the hair is pulled.

Thus, either after (preferably) or prior to the application of HRC and wax-depilation, the application of a substance with an index of refraction higher than that of the hair and the skin, and transparent to the beam wavelength of radiation, may be useful. A higher refractive index substance 1134 to the emptied follicle is shown in the left side of FIG. 11B. The substance 1134, shown filling the emptied hair ducts 1120 from which the hair shafts have been pulled, can serve as a fiber-core of liquid filling in the emptied hair ducts and thus enhances light propagation in an fiber-optic-like manner. While this step enhances photon propagation down the emptied hair ducts, it is not required for the practice of the present embodiment, and is therefore optional.

Finally, in a variation on the present embodiment, the covering (to the extent possible) of the hair duct walls 1130 themselves with high reflectance coating may be a desired objective.

The principle of operation here is that coating of at least the upper portion of the duct walls with HRC 360 will allow the incoming light rays to propagate down the emptied hair ducts towards the hair bulb and papilla 1132 in a similar manner to the way electromagnetic energy propagates down a metal-coated hollow-wave-guide (HWG) 1136 with relatively little loss of energy.

This is illustrated by the left-most follicle in FIG. 11B and the constant thickness of the coupled light arrows 607, indicates that very little attenuation or leakage is expected if the high reflectance coating layer can penetrate the hair ducts and create a hollow wave guide like effect in the duct.

To achieve this goal, HRC may be applied to the targeted skin area and massaged or ultrasound-forced into the hair ducts either prior to wax-epilation, or after wax epilation. The advantage of HRC application prior to wax-epilating is that the presence hair in the duct ensures that the hair ducts will not be clogged up by the HRC layer which will then act to block (reflect) energy propagating toward the hair bulb and papilla.

Using ultrasound field or other methods to force the HRC suspension into at least part of the ducts will allow enhanced waveguide-like penetration of light deeper into the follicle for an enhanced interaction with the hair bulb and papilla. Of course, the HRC particles in the HRC suspension must be smaller than the hair duct openings (i.e., smaller than about 60 $\mu$m) yet safe to the skin and the body.

In cases where penetration of the high reflectance coating into deeper hair ducts regions and all the way to the hair bulbs is not possible and general forcing of the HRC fluid into the ducts is difficult, it will be advantageous to first pull out the hair shafts thus exposing a larger area of the ducts and only then to apply the high reflectance coating to the skin and emptied ducts. In these cases, an enhanced penetration of HRC to deeper duct regions will be accomplished and enhanced light propagation will be achieved. In cases where the HRC still blocks the emptied follicle the application of massaging, an ultrasound field or other means of perturbing the hair ducts (or vibrating and stretching them) can help remove such blockage, as illustrated in FIG. 12B and discussed below.

6. APPLICATION OF A SUBSTANCE OF HIGH REFLECTANCE PROPERTIES TO THE SKIN SURFACE FOLLOWED BY PULLING OF THE HAIR SHAFTS OUT OF THE SKIN, SMALL-BEAM DIAMETER METHODS

This embodiment is essentially the same as that of Embodiment 5 above except that instead of the large area single beam illuminating an area large enough to cover a multiple-hair ducts, either one of the methods employing a small size beam as described by Embodiments 2a and 2b are used. Indeed this embodiment is essentially the same as those of Embodiments 2a and 2b except that hair shafts cutting step is replaced by wax-epilating step.

Thus, after the application of high reflectance coating layer to the targeted skin surface, the hair is wax-stripped substantially without removing or damaging the high reflectance coating. The beam is focused on an area of the high reflectance coating covered skin containing multiple cut hair shafts. Light is reflected by most of the skin and coupled substantially only to the exposed and emptied hair follicle (with its shaft removed and which are now the only uncoated locations on the skin and in the beam path. The light is coupled to the shafts and propagates longitudinally along the emptied follicle until it is coupled to the hair bulb and papilla, destroying the tissue and blood vessels sustaining the hair thereby killing the hair. The light is also absorbed along its propagation path down the emptied follicle by the follicle walls thereby heating and destroying the tissue sustaining the hair.

7. PULLING THE HAIR SHAFTS OUT OF THE SKIN, FOLLOWED BY THE APPLICATION OF A COATING LAYER OF A SUBSTANCE OF HIGH REFLECTANCE PROPERTIES, LARGE-BEAM DIAMETER METHOD

This embodiment is essentially the same as the one described by Embodiments 1A and 1B except that the hair cutting step is replaced by wax-epilating step and the high reflectance coating application step is postponed until after the hair is pulled out of the follicles. In addition, no application of a substance with special index of refraction properties is required. It should also be noted that unlike the method practiced in embodiment 5 and embodiment 6, here, significantly, the high reflectance coating layer is applied only after the hair shafts are removed from the follicles and skin.

Figure 12A:
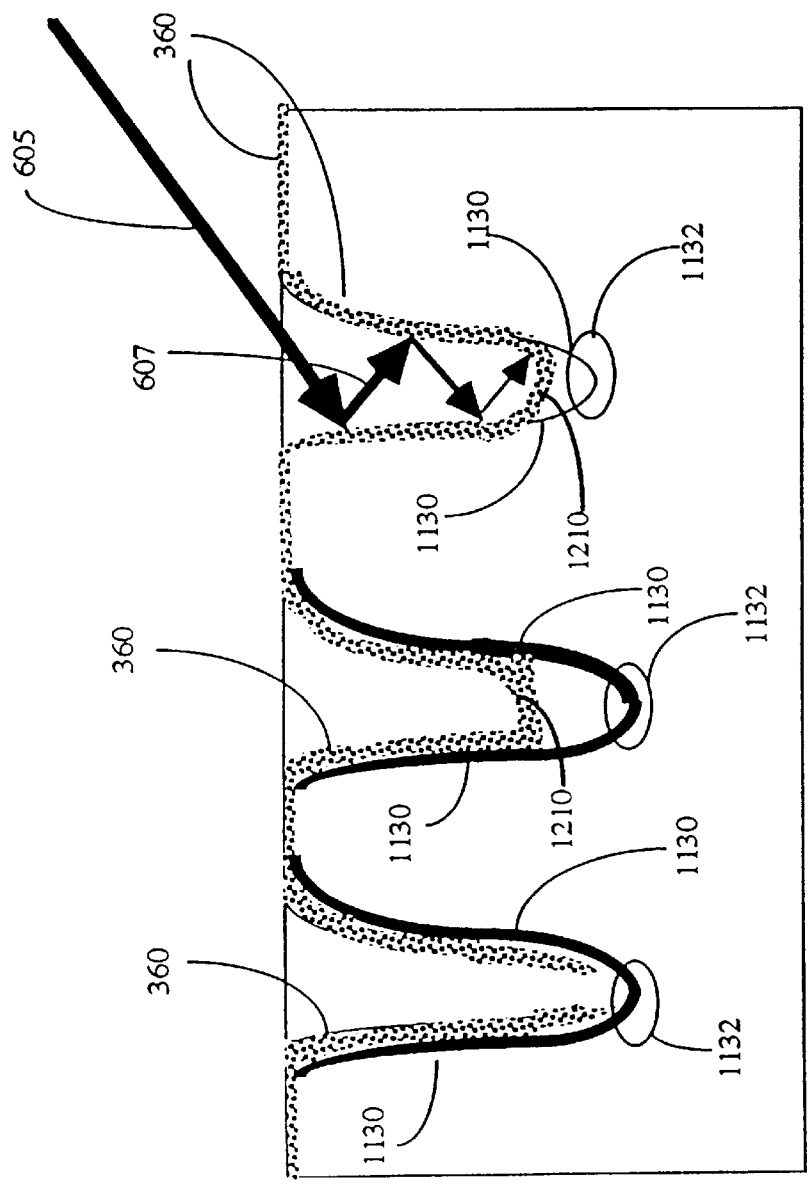
FIG. 12A is a graphical representation of the emptied hair follicle following the process of pulling out the hair shafts and after coating of the skin surface with a substance of high reflectance which has also been forced into the hair duct wherein the desired effect yields hair duct walls substantially covered with the substance of high reflectance but with the bottom of ducts left open so that light may be able to propagate further down the follicle to the bulb and papilla regions such that in practice it is expected that some blocking of the ducts by the substance of high reflectance may occur, as illustrated by the hair ducts drawn in the middle and right hand side of the figure.
Figure 12B:
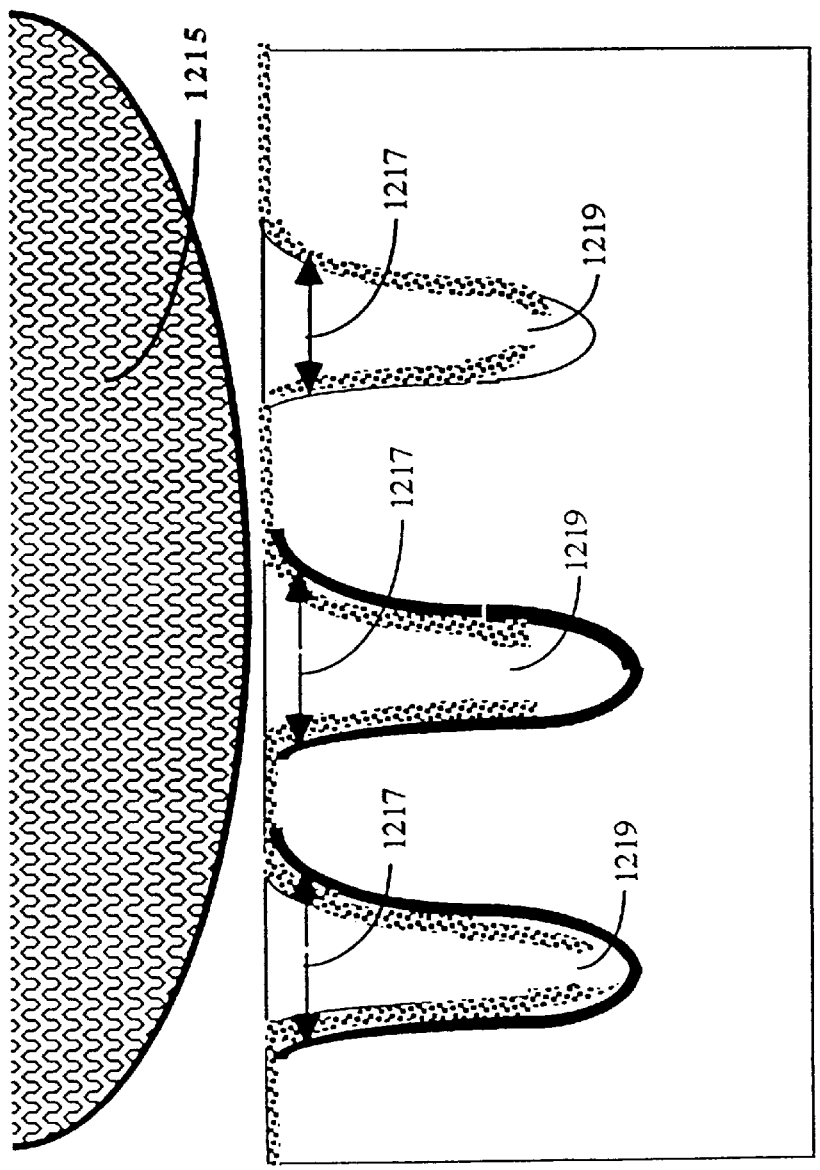
FIG. 12B is a graphical representation of the process of forcing an opening through a potential blockage created by the substance of high reflectance coating in the emptied hair ducts (for example, through the application of mechanical vibration to the skin surface)

This embodiment can be better understood by referring to FIGS. 12A and 12B: In this embodiment, removal of hair shafts from the follicles (for example wax-depilation) is the first step after cleaning and preparing the targeted skin surface. Significantly, no HRC is applied to the skin surface until the hair shafts have been pulled out. Applying the high reflectance coating layer after the step of pulling out the hair shafts allows much better penetration of the HRC into the hair duct. To enhance such penetration massaging or application of ultrasound field may be used. The enhanced access to the ducts leads to better HRC 360 covering of the hair-ducts walls 1130.

Forcing any substance down the hair ducts is not easy given the relatively small size of the follicle. Thus high reflectance coating substance penetration into the hair ducts and covering of the hair ducts walls with HRC can be expected to be only partial. Removal of the hair shafts leave the ducts 120 better exposed for high reflectance coating substance penetration. In this case, partial or even deep penetration (if additional methods—such as application of ultrasound—to force the HRC substance into the emptied hair follicles are used) of the hair ducts and follicles is possible.

Depending on the high reflectance coating fluid viscosity, however, blocking 1210 or partial filling of the hair ducts by the high reflectance coating substance 360 can be expected. Such blocking will, naturally, prevent penetration of the depilatory beam all the way to the lower follicle region 1132. To overcome this difficulty vibration of the skin may be induced by means of an ultrasound field or through other means. Such vibrations will stretch the hair duct walls 1130 and force the separation of the blocking portion of the HRC fluid inside the hair ducts from the hair duct walls thus opening the hair ducts and confining the HRC substantially only to the hair duct walls. FIG. 12B illustrates an exemplary probe 1215 generating vibrations in the skin which induce hair duct walls motion in the directions indicated by the arrows 1217. This vibrator motion induced by the probe (for example an ultrasound probe) will results in enhanced HRC penetration, opening of blockage in the ducts 1219 and enhanced, deeper penetration of the depilatory beam. To ensure that the emptied hair ducts remain open (to the extent that the light can propagate down the duct towards the hair bulb and papilla), in addition to the exemplary ultrasound field described above, a high pressure air or gas flow, a suction or other mild perturbation of the skin may also be used.

The depilatory beam is subsequently applied to the skin in a manner similar to the one described in Embodiment 1. Light will be reflected from most of the skin but will be admitted and propagated by the emptied hair pores that with the enhanced wall reflection of the HRC that adheres to the ducts walls, will act as a hollow waveguide. Incident, epilating light will thus propagate downward along the hair ducts towards the bottom of the follicle and the papilla with relatively little absorption losses along the way. The light will then be absorbed mainly at the lower portions of the follicle and by the papilla destroying the components feeding and nourishing the hair.

8. PULLING THE HAIR SHAFTS OUT OF THE SKIN FOLLOWED BY THE APPLICATION OF A COATING LAYER OF A SUBSTANCE OF HIGH REFLECTANCE, SMALL-BEAM DIAMETER METHODS

This embodiment is essentially the same as the one described by Embodiment 7 except that the small-beam-diameter beam methods of Embodiment 2a and Embodiment 2b are used instead of the Large-diameter beam of Embodiments 1A and 1B.

9. APPLICATION OF HIGH REFLECTIVE COATING FOLLOWED BY PULLING THE HAIR SHAFTS OUT OF THE SKIN AND THE APPLICATION OF A SUBSTANCE WITH A HIGH REFRACTIVE INDEX—LARGER AREA/SINGLE BEAM METHOD

This embodiment is essentially the same as the one described by Embodiments 1A and 1B except for the changes indicated below:

No substance with index of refraction lower than that of the hair need be applied.

High reflectance coating is applied to both the skin and the hair shafts.

The hair cutting step is replaced by pulling the hair shafts out of the skin. Any method for pulling multiple-hair out of the targeted skin surface is acceptable as long as such method does not damage the high reflectance coating layer.

A transparent substance of high refractive index (i.e., higher than that of the skin, for example n>1.6) is applied to the skin and massaged (or forced with ultrasound field) into the skin so that light can propagate into the lower/deeper regions of the follicle (in a manner similar to that of optical fibers), and be absorbed in the lower follicle, papilla and tissue feeding the hair.

10. APPLICATION OF HIGH REFLECTIVE COATING FOLLOWED BY PULLING THE HAIR SHAFTS OUT OF THE SKIN AND THE APPLICATION OF A SUBSTANCE WITH A HIGH REFRACTIVE INDEX, SMALL-DIAMETER BEAM METHOD

This embodiment is essentially the same as the one described by Embodiment 11 except that the small-area beams and scanning methods of Embodiments 2a and 2b are used.

ALTERNATIVE METHODOLOGY

A substantially different concept is provided by embodiments 11–13, described in detail below. Here instead of maximizing light propagation and photon penetration towards the follicle roots and papilla, the basic idea is to deposit the epilating energy substantially at the surface, thus converting this energy into heat, and then to allow rapid, selective penetration of this thermal energy into the deeper follicle regions and the papilla.

THREE OBJECTIVES MUST BE ACHIEVED

1. Energy in the skin must be concentrated substantially only in the follicle area;
2. The deposited energy, now in the form of thermal energy, must be efficiently conducted down the hair follicle to the targeted tissue nourishing and sustaining the hair; and
3. Heat must not be conducted away to larger volume or surface regions of the skin where it can cause collateral damage and/or uselessly be transferred to the outer environment.

Also, it must be emphasized that in the practice of some of the following embodiments (Embodiments 11A and 11B) the requirements on the energy source can be broadened from a source of electromagnetic radiation to that of any source generating energy which can be superficially deposited in the designated layer of energy-absorbing substance applied to the skin's outer surface. Since some of the embodiments 11A and 11B only require that energy will be deposited and subsequently converted to heat in a specific surface layer, any energy source that accomplishes this task may be used in the practice of these embodiments invention. This broadens the requirements on the invention's energy source from electromagnetic radiation source to any source capable of generating and depositing thermal energy in the designated surface layer, and while laser sources can be utilized for very precise energy deposition and careful control of the amount of energy deposited, other heat source including simple contact with a hot source (i.e., a source of high thermal energy, even, for example, a heating iron) for a controlled duration of time, can serve the practice of the embodiments 11A and 11B as well.

FIGS. 13A through 13G illustrate exemplary techniques for achieving these objectives and are described in conjunction with the following specific embodiments.

11A. APPLICATION OF A THERMALLY CONDUCTIVE SUBSTANCE TO THE HAIR DUCTS, APPLICATION OF AN INSULATING LAYER, APPLICATION OF A LAYER OF HIGH REFLECTANCE COATING, HAIR CUTTING.

Figure 13A:
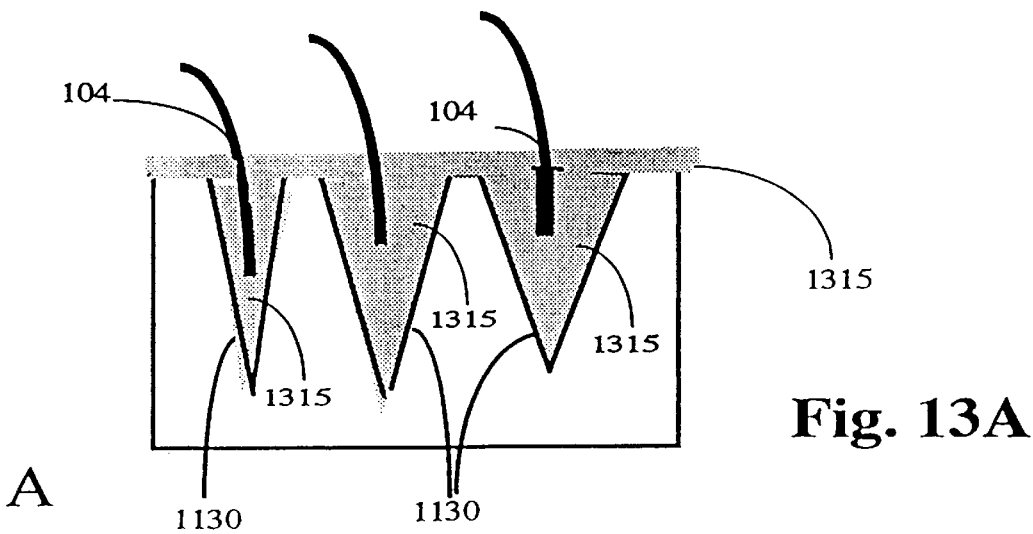
FIG. 13A is a graphical representation of the process of application of a substance of high thermal conductivity to the targeted skin surface and hair ducts.
Figure 13B:
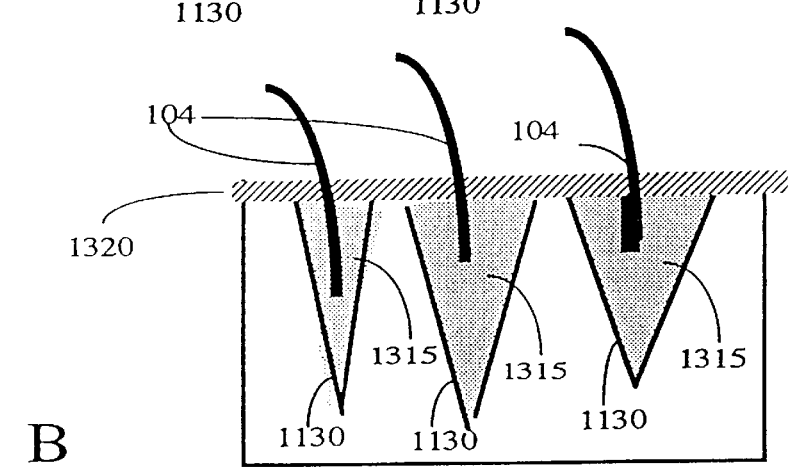
FIG. 13B is a graphical representation of the process of removing the substance of high thermal conductivity from the targeted skin surface substantially without removing the substance of high thermal conductivity from the hair ducts followed by application of a substance of low thermal conductivity (a thermal insulator) to the skin surface.
Figure 13C:
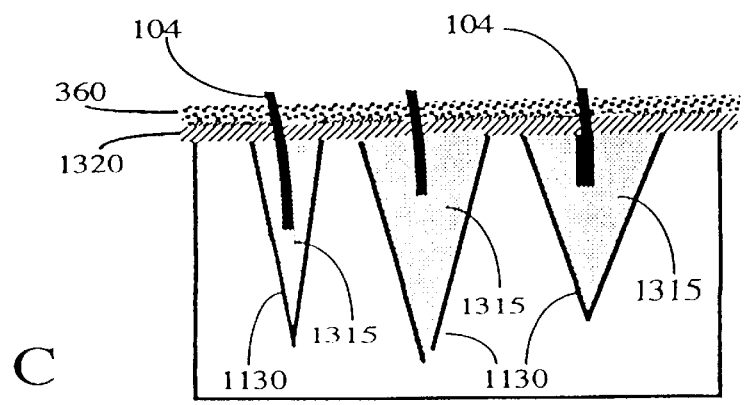
FIG. 13C is a graphical representation of the process of application of a layer of a substance of high reflectance to the targeted skin surface subsequent to the treatments described by FIG. 13A and FIG. 13B.

In this embodiment the following steps must be followed.
1. As FIG. 13A shows, a substance with substantially high thermal conductivity (HTC) 1315 is first applied to the surface of the skin and is forced into the follicular ducts (for example through massaging of the treated area or through the application of ultrasound).
2. As FIG. 13B shows, the excess high thermal conductivity substance is wiped off from the skin surface and a substance with substantially low thermal conductivity 1320 (LTC) may be applied as an external layer on the skin surface (but it is not forced into the hair ducts).
3. As FIG. 13C shows, a high reflectance coating 360 is applied to the skin surface as described above and the hair is cut as close to the skin as possible but without damaging the high reflectance coating layer.
4. Irradiation now follows in accordance with either one of the four methods described in Embodiments 1a or 1b, 2a or 2b, with the parameters required to generate irreversible damage to the hair as described above.

Figure 13D:
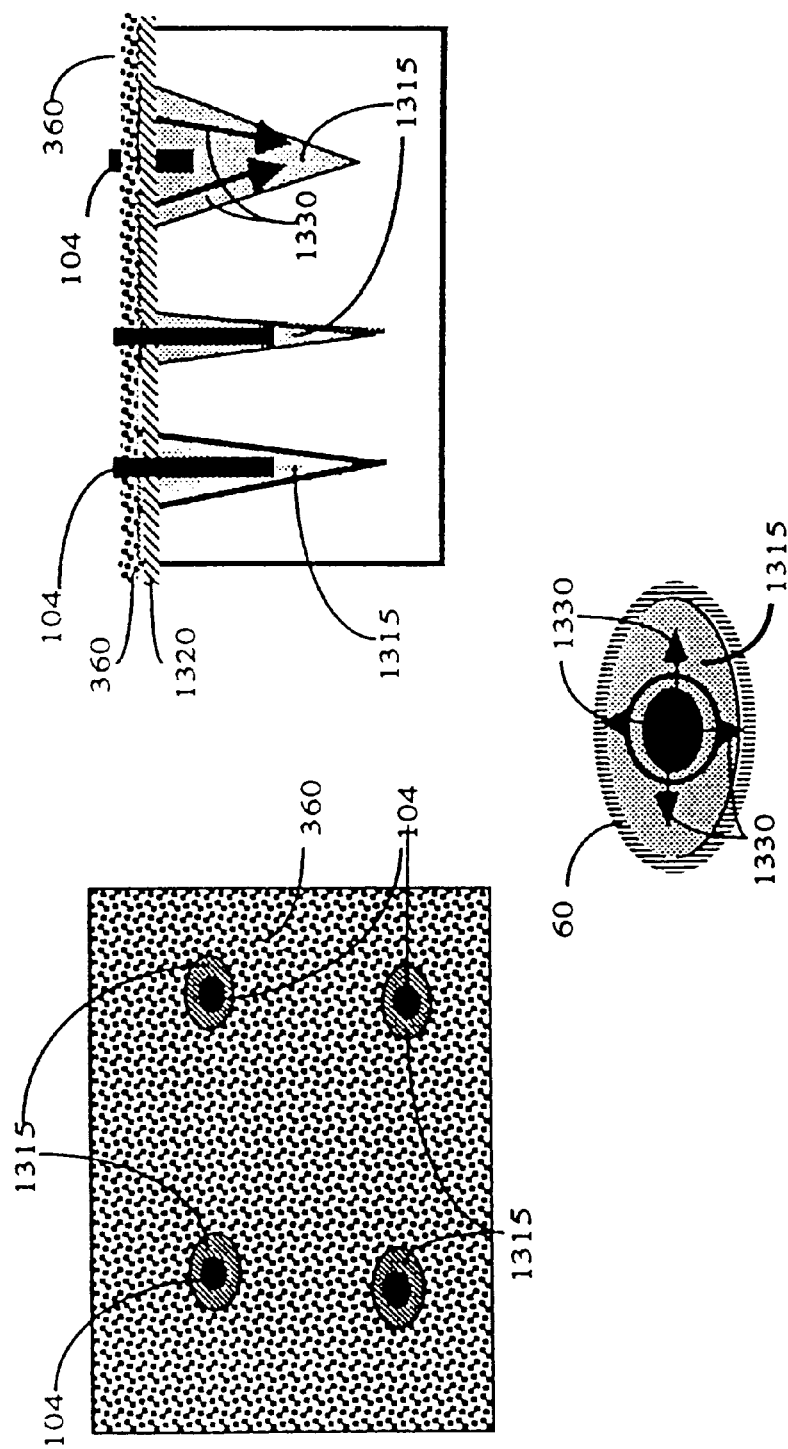
FIG. 13D is a top view (on the left) and side view (on the right) of the treated skin surface and hair follicles following the treatment steps illustrated in FIG. 13A through FIG. 13C and also illustrating the directions of heat flow.
Figure 13E:
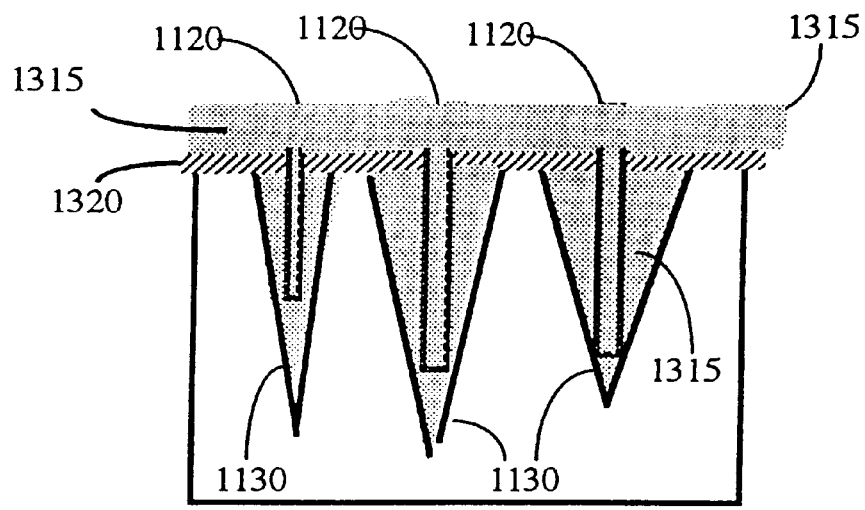
FIG. 13E is a graphical representation of the process of application of a substance of high thermal conductivity to the hair ducts followed by application of a substance of low thermal conductivity, pulling the hair shafts out and the application of an additional layer of a substance of a high thermal conductivity.

This embodiment is designed to augment poor light coupling and/or poor propagation of incoming beam energy down the hair shafts (for example due to particularly heavy pigmentation or hair shafts characteristics that make it difficult to propagate light through them) and hair ducts. FIG. 13D illustrates beam coupling to the hair shaft, conversion of the beam energy to heat, and the direction of heat flow. Here, instead of attempting to enhance the optical energy propagation, the present embodiment considers the practical range of absorption of electromagnetic radiation within the cut hair shaft opening, then relies on the thermal contact of this heated portion of the hair shafts 104 with the HTC 360 to transfer the thermal energy down along the hair duct to the lower follicle region and towards the papilla 112. The arrows 1330 indicate the direction of heat flow.

Since deep light penetration is not essential for this method, radiation wavelength may include all wavelengths that are absorbed well by the exposed, cut hair as long as the selected wavelength is also within the range of high reflectivity exhibited by the HRC substance and is reflected well from the rest of the skin surface.

Also, hair coloring (addition of light absorbing pigmentation) may be useful within the practice of this embodiment. This is particularly true for light colored hair that may not absorb the light as well as dark hair. However, it is important to note that the objective is to distribute the incoming light energy as thermal energy, substantially evenly throughout the hair follicle. Thus, it is not imperative that the light energy be absorbed only in the upper follicle area and light penetration into deeper region should serve equally well.

11B. APPLICATION OF A THERMALLY CONDUCTIVE MATERIAL TO THE HAIR DUCTS, PULLING THE HAIR SHAFTS OUT OF THE SKIN, APPLICATION OF A GOOD ABSORBER, NO APPLICATION OF HIGH REFLECTANCE COATING

This embodiment is essentially equivalent to that of Embodiment 11A except that the step of applying to the targeted skin a substance of high reflectance is replaced by the application of a substance of high absorbance (SHA) and possibly the application of an insulating layer between said SHA and the skin.

Figure 13F:
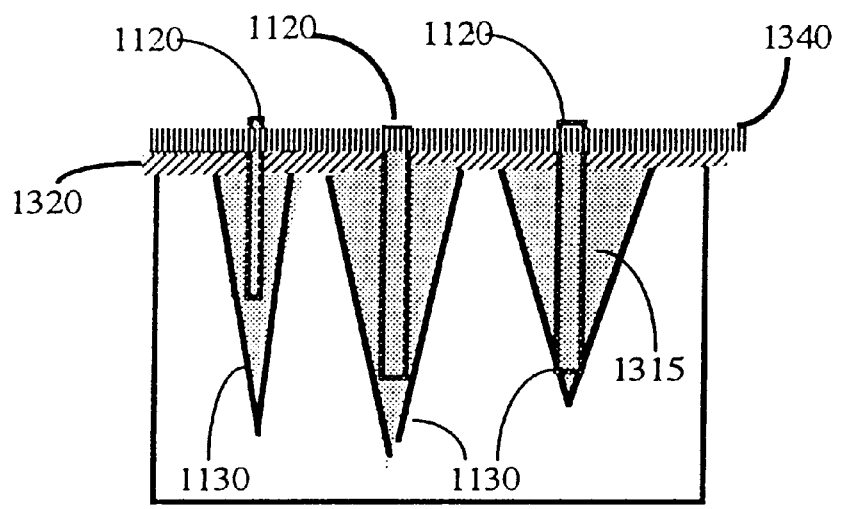
FIG. 13F is a graphical representation of the process of application of a substance of high thermal conductivity to the hair ducts followed by application of a substance of low thermal conductivity, pulling the hair shafts out and the application of a layer of a substance of a high optical absorption.

Since the practice of this embodiment for the present invention relies on the use of a substance of a high thermal conductivity forced into the hair ducts to transfer the depilatory energy to the hair-sustaining tissue, it is possible in this case to not use a substance of high reflectance coating. Instead, this embodiment relies on the deposition of optical energy at the surface of the skin, substantially without damaging the skin, and the efficient transfer of this energy through thermal conductance down the hair-follicle and to the targeted hair-sustaining tissue. The present embodiment also relies on the thermal insulating properties of the skin and, possibly, the application of an additional low thermal conductance layer between the skin and the substance of high optical absorber—the top layer applied to the skin, designed to intercept and absorb the incoming beam. As indicated by FIGS. 13A–B and FIGS. 13E–F, the following steps should be performed:

1. The skin is coated with a substance of high thermal conductivity (i.e., a good thermal conductor) 1315 which is also forced (for example through massaging or the application of an ultrasound field) into the hair ducts (see FIG. 13A)
2. Only the skin surface is then thoroughly cleaned of the substance of high thermal conductivity substantially without removing the substance of high thermal conductivity 1315 from the hair ducts.
3. The skin is then covered with a layer of a substance of low thermal conductivity 1320 (i.e., a thermal insulator, see FIG. 13B).
4. The hair shafts are pulled out of the hair follicles (e.g. by using wax-depilation or by pulling them out using other means) substantially without damaging the layers of previously applied coating.
5. The skin is further covered with a new layer of a substance of high thermal conductivity 1315 (see FIG. 13E) which is rubbed, massaged, or forced (e.g. by applying an ultrasound field as described above) into the emptied hair ducts. With the hair shafts removed the substance of high thermal conductivity should be able to easily penetrate into the emptied hair duct 1120 and substantially create a continuum (establish a thermal contact and at least partial thermal continuity) with the hair duct walls which should be at least partially covered with the substance of high thermal conductivity applied during step 1 as described above.
6. This step consist of two alternatives:

Alternative (a) of FIG. 13F. The layer of a substance of high thermal conductivity 1315 is substantially removed from the skin surface and a layer of a good absorber 1340 is applied to the targeted skin surface.

Alternative (b) which is not shown in the figures. The layer of a substance of high thermal conductivity 1315 (See FIG. 13E) is not removed from the skin surface and a layer of a good absorber 1340 is simply applied on top of the layer of the substance of high thermal conductivity 1315.

The difference between step 6.*a*. and 6.*b*. is that in the former the beam absorbing layer is mostly in thermal contact with an insulating layer (thus substantially avoiding collateral damage to other skin components), and also in thermal contact with the substance of high thermal conductivity inserted into the hair ducts. The layer of beam absorbing substance 1340 heats up and transfers its thermal energy most efficiently via the substance of high thermal conductivity down the hair ducts and to the targeted hair-sustaining tissue. In this case, however, much of beam energy deposited in the good absorber layer 1340 is not used for destroying the hair since much of the beam absorbing layer is thermally insulated from the hair and skin and does not have good thermal contact to transfer its thermal energy to the hair follicles. This deposited beam energy will simply be transferred out to the environment.

If the variant of step 6.*b*. is taken, the layer of a substance of high thermal conductivity is not removed. Energy deposited in the layer of beam absorbing substance 1340 is transferred to the layer of a substance of high thermal conductivity 1315. This thermal energy quickly diffuses along this layer but is essentially trapped (sandwiched) between an insulating layer and the layer of good absorber 1340. The only easy energy transfer route for this thermal energy is down the hair ducts which are filled with the substance of high thermal conductivity 1315. In a real sense the present embodiment thus forces the absorbed beam energy to travel (as heat) along the thermal conductor layer 1315 along the surface of the skin and then follow the substance of high thermal conductivity filled hair ducts and flow down ducts to destroy the targeted papilla and hair-sustaining tissue. The advantages of this variant is that more incident beam energy is being utilized and more thermal energy will be transferred (more efficiently) to the tissue targeted for destruction.

7. Irradiation now follows in accordance with either one of the four methods described in embodiments 1a and 1b, 2a and 2b, with the parameters required to destroy the targeted papilla and hair-sustaining tissue as described above (although some modification in these parameters may be needed).

Yet another alternative variant to the present embodiment is described below.

Figure 13G:
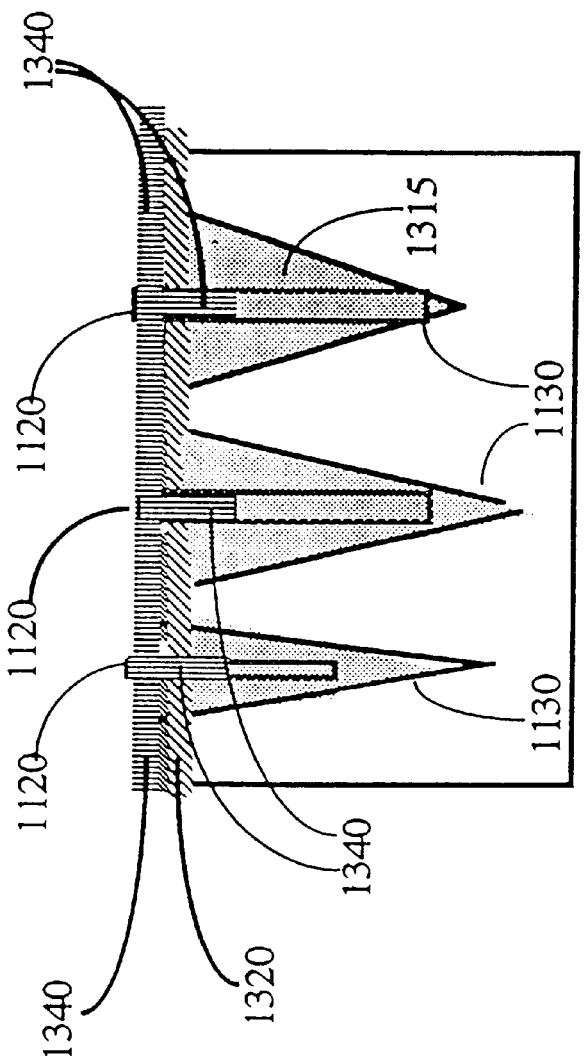
FIG. 13G is a graphical representation of the process of application of a substance of high thermal conductivity to the hair ducts followed by application of a substance of low thermal conductivity (an insulator), pulling the hair shafts out and the application of a layer of a substance of a high optical absorption which is then forced into the emptied spaces of the removed hair shafts.

5'. The second application of a substance of high thermal conductivity is eliminated. Instead, here, a layer of low thermal conductivity (a thermal insulator) 1320 is applied to skin surface after the layer of a substance of high thermal conductivity 1315 has been applied and forced into the hair shafts and then removed from the skin. The hair shafts are then removed, and a layer of a substance of high absorbance 1340 is applied on top of the layer of low thermal conductivity (the insulator) 1320 (see in FIG. 13G). The substance of high absorption 1340 is then also forced to penetrate the emptied hair duct (since hair shafts were removed in step 4), and to form a physical contact with the layer of substance of high thermal conductivity 1315 in the hair ducts as shown in FIG. 13G.

6'. Irradiation now follows in accordance with either one of the four methods described in embodiments 1A and 1B, 2A and 2B, with the parameters required to destroy the targeted papilla and hair-sustaining tissue as described above (although some modification in these parameters may be needed).

As seen from 5' and 6' above, this variant relies on the penetration and direct contact of the layer of substance of high beam absorbance 1340 (applied after hair shaft removal) with the substance of high thermal conductance forced into the hair ducts prior to hair shaft removal. This variant has the advantage of being somewhat simpler to practice (i.e., not requiring the additional thermally insulating layer).

In general, the practice of embodiment 11B ensures that the hair-free skin is substantially protected through the application of a layer of a substance of low thermal conductivity 1320 and the thermally insulating properties of the epidermis itself.

Also, if desired, to increase the effectiveness of use of the beam energy in all of the variants of embodiment 11B, an additional layer of optically transparent and thermally insulating substance may be applied on top of the absorbing layer 1340. This will mitigate heat loss to the outside environment and further enhance redirecting of the thermal energy flow substantially mostly into the hair ducts. Precise control of the distribution of deposited energy can be easily achieved through the knowledge of laser parameters, and the optical (principally the absorption coefficient of the high absorption layer) and thermal properties (e.g., heat capacity and thermal conductivity) of the various layers applied.

11C. HAIR BLEACHING, APPLICATION OF A THERMALLY CONDUCTIVE MATERIAL TO THE HAIR DUCTS

This embodiment is essentially the same as that of Embodiment 11A, and Embodiment 11B except that the hair shafts are not removed but, instead are bleached (as an added first step) in order to enhance beam propagation. The basic principle in this case is to enhance beam energy deposition in deeper regions of the hair.

The subsequent steps of Embodiments 11A and 11B are then followed except that the hair is not pulled out as in step 4 of Embodiments 11A and 11B. Instead, prior to the irradiation step of 11A-4 and 11B-7 the hair is cut substantially without damaging any of the layers applied to the skin.

Irradiation then follows in accordance with either one of the four methods described in Embodiments 1A and 1B, 2A and 2B, with the parameters required to generate irreversible damage to the hair as described in above, although some modification in these parameters may be needed.

The idea here is simply to use the same techniques as in Embodiments 11A and 11B but to enhance the optical penetration of and propagation in the hair shaft as much as possible so that light is also allowed to propagate optically into the deepest regions of the hair follicle as possible.

12. APPLICATION OF A THERMALLY CONDUCTIVE MATERIAL TO THE HAIR DUCTS, APPLICATION OF HIGH REFLECTANCE COATING, FOLLOWED BY HAIR SHAFTS REMOVAL

This embodiment is essentially the same as the one described by Embodiment 11A above, except that the hair-shaving step is replaced by the complete removal of the hair through wax-depilation or similar means for removing the hair shafts.

Figure 14A:
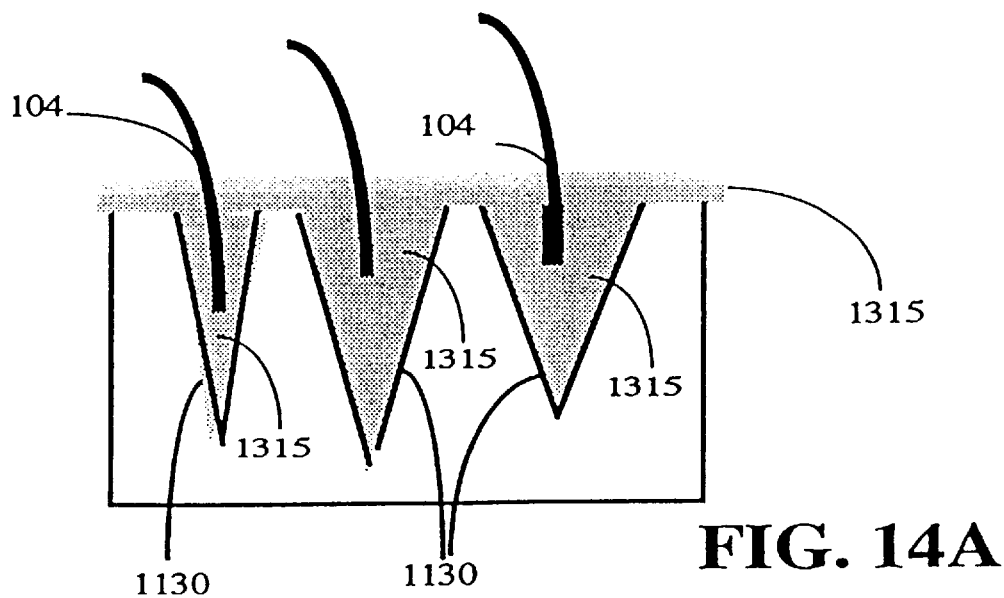
FIG. 14A is a graphical representation of the process of application of a substance of high thermal conductivity to the hair ducts.
Figure 14B:
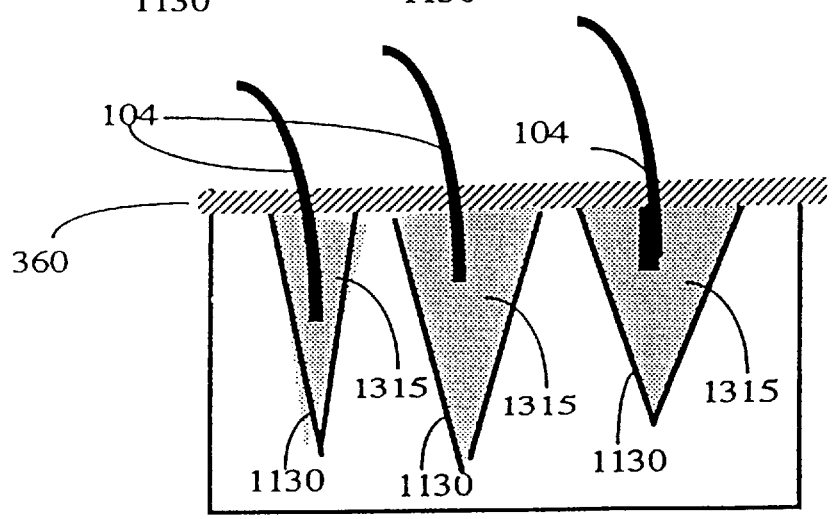
FIG. 14B is a graphical representation of the process of removing the layer of high thermal conductivity only from the skin surface and then applying a layer of a substance of high reflectance over the targeted skin surface.

As FIG. 14A shows, a substance of high thermal conductivity 1315 is applied to the skin and forced into the hair ducts. The skin surface is then cleaned FIG. 14B substantially without removing the substance of high thermal conductivity 1315 from the hair ducts. Next, a substance of high reflectance properties 360 is applied to the skin surface. Finally, the hair shafts are removed through wax-depilation or other means thus creating an evacuated spaces in the regions which they used to occupy.

With the skin protected by the substance of high reflectance coating layer the light is coupled optically to the exposed, emptied spaces left by the removed hair shafts. The incident light is reflected off the layer of substance of high reflectance on the surface. The incident light is coupled only to the openings created by the removed hair shafts. As the light propagates down the emptied hair ducts it is also being absorbed by the follicle and by the substance of high thermal conductivity in the ducts. Absorbed light energy is converted into thermal energy and this heat is quickly conducted and distributed throughout the hair ducts thereby heating and killing follicles.

Figure 14C:
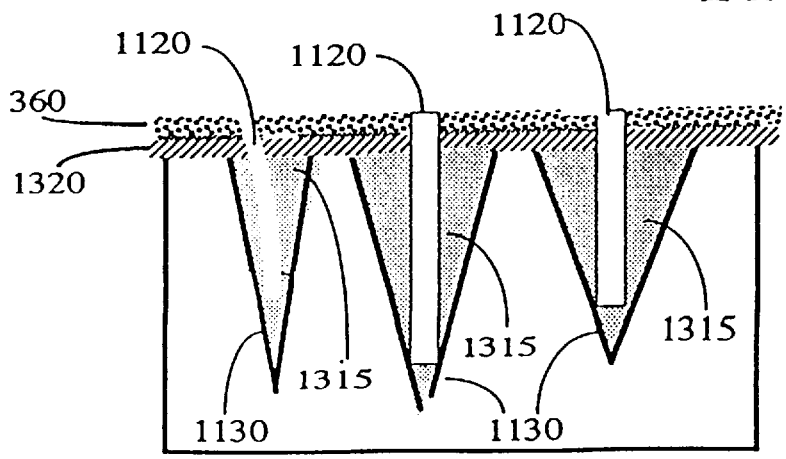
FIG. 14C is a graphical representation of the sequence of application of a substance of high thermal conductivity to the hair ducts, removing the layer of high thermal conductivity only from the skin surface and applying a layer of a substance of low thermal conductivity (an insulator), followed by the application of a layer of high reflectance over the targeted skin surface, and finally, removing the hair shafts from the targeted skin area.

FIG. 14C illustrates another variant of the present embodiment. Just prior to the steps of the application of a substance of high reflectance 360 and hair shaft removal, one may apply a layer of a good thermal insulator 1320 (i.e., a substance of low thermal conductivity) to enhance protection of the skin under the layer of high reflectance coating. Alternatively, if the substance of high reflectance can also be chosen so it possess properties of low thermal conductivity, it will be able to perform the combined function of reflecting incident beam and providing additional thermal insulation.

13. APPLICATION OF HIGH REFLECTANCE COATING, APPLICATION OF A GOOD THERMAL CONDUCTOR, CUTTING OF THE HAIR SHAFTS, CONDUCTOR-TRIMMING METHOD

Figure 15A:
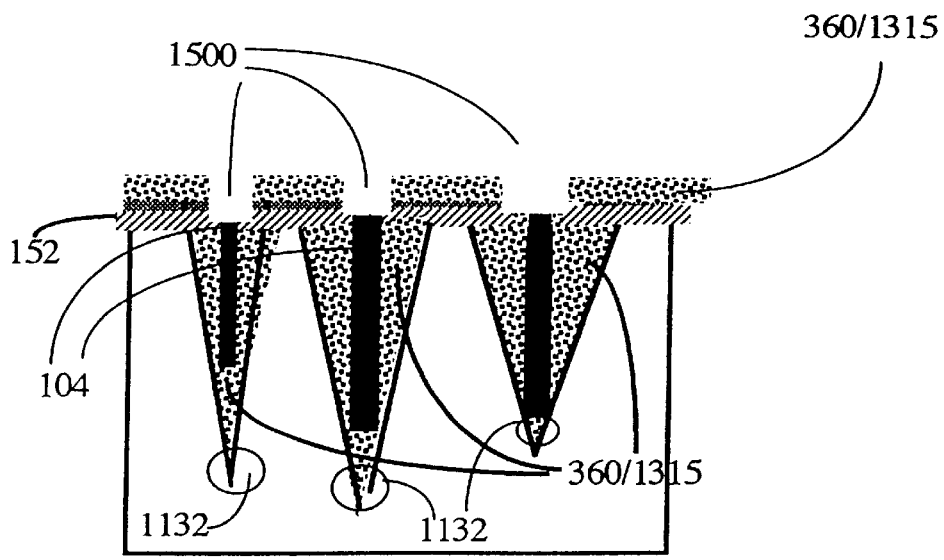
FIGS. 15A and 15B are graphical representations (side and top view) of the method of trimming for the generation of an insulating circle around the hair follicle at the targeted skin surface.
Figure 15B:
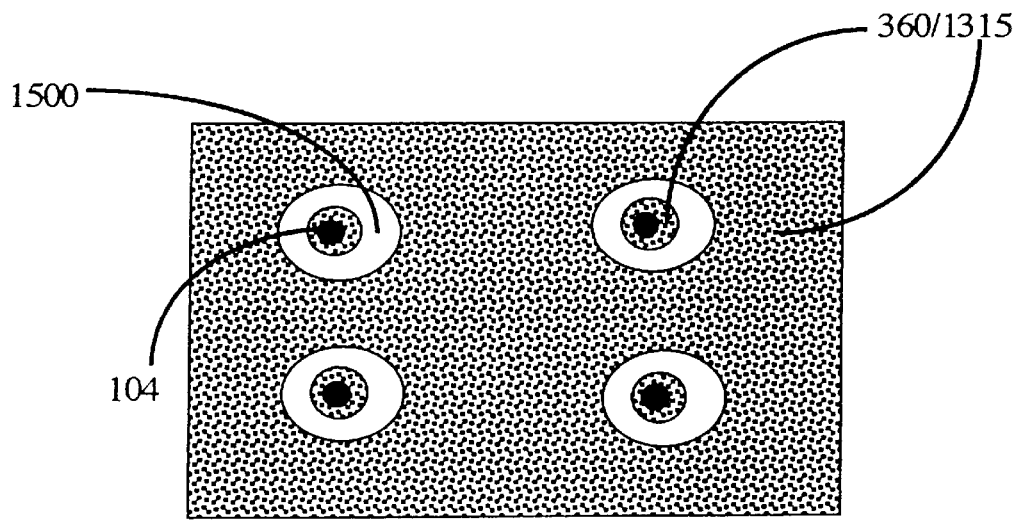

This embodiment is essentially the same as the one described by Embodiment 11A except that the high reflectance coating substance is so chosen so it is also a good thermal conductor. Thus, the surface is coated with the high reflectance coating/high thermal conductivity substance which is also forced into the hair ducts (through ultrasound or massaging), the hair is cut in a manner that substantially does not damage the high reflectance coating/high thermal conductivity layer. Trimming of HRC/HTC in the hair duct severs the contact with the surface HRC/HTC as shown in FIG. 15. This disruption is achieved by removing a small ring of HRC around the hair shaft and hair duct. Such trimming can be accomplished for example through a combination of the hair scanning method of Embodiments 2 and application of high peak power around the vicinity of the hair to achieve local ablation deep enough to remove any thermally conducting material and expose the highly insulating epidermis in a ring a few tens of a micrometer wide around the hair shaft. Irradiation can then follow either the methods of embodiments 1A, 1B, 2A, and 2B. The beam is coupled substantially only to the cut hair shafts, and is reflected by the rest of the surface coated by the high reflectance coating/high thermal conductivity layer. Beam energy deposited in the hair shafts is converted to heat which is then, due to the efficient heat transfer by the high reflectance coating/high thermal conductivity substance in the hair ducts, is rapidly conducted throughout the hair ducts and into the hair root thereby destroying the targeted hair-sustaining tissue and papilla.

FIG. 15 is a graphical representation of the use of a substance that combines the properties of high reflectance AND high thermal conductivity 1315/360 with the use of hair shaft cutting, followed by the identification of the hair shaft positions, and then, followed by the ablation of an insulating ring around the shaft down through the high reflectance coating/high thermal conductivity layer and down to the epidermis 152. Such an ablation step creates an insulating ring around the hair shafts so that heat is conducted substantially only down the hair ducts and towards the papilla and hair bulb 1132, and is substantially not allowed to diffuse along the skin outer coating.

14. APPLICATION OF A THERMALLY CONDUCTIVE SUBSTANCE TO THE HAIR DUCTS, SHAVING OF HAIR SHAFTS, NO APPLICATION OF A LAYER OF HIGH REFLECTANCE COATING

This embodiment is similar Embodiment 11A, except that here no high reflectance coating is used, instead the embodiment relies on the natural reflectivity and low absorption properties of the skin and the natural absorption characteristics of the hair shafts, augmented by the insertion of a substance of high thermal conductivity to the hair ducts.

In this and all the embodiments that do not make use of HRC (for example, embodiment 14 through 18), it is still possible (although not as easy) to use the scanning-interrogating means of the previous embodiments and small-beam techniques. The reason is that the skin surface reflectivity is different than that of the hair and, in addition, the melanin in the skin, will absorbed scattered light that would thus tend to be less backscattered towards a detector over the target than light backscattered and escaping the skin. Thus, the amount of light scattered back will be different, and differentiation between the skin surface and the cut hair shaft opening is still possible (though not as easy as with HRC).

In the practice of this embodiment the following steps must be taken:

1. Apply a good thermal conductor substance (high thermal conductivity) to the skin and force it into the hair duct through massaging, application of ultrasound or other methods.
2. Wipe off the excess of the high thermal conductivity substance from the surface of the skin (this step must be rigorously followed or heat may be lost due to conduction on the surface.
3. Cut hair as close to the skin as possible.
4. Apply an optical field by either one of methods discussed in Embodiments 1A, 1B, 2A and 2B (i.e., large-area beam, scanning beam, two beams, etc.) with the parameters required to generate irreversible damage to the hair as described above.

The light thus deposited in the absorbing hair shaft will heat the shaft and the thermally conducting fluid in the ducts. Heat will be conducted to the lower portions of the follicle thus irreversibly damaging the tissue sustaining the hair. The electromagnetic radiation wavelength should be selected so it is absorbed most efficiently in melanin while minimizing the absorption in hemoglobin and water. Light in the wavelength of 500 nm to 1.1 $\mu$m substantially accomplishes this goal.

Light that is not absorbed by the hair follicle and not reflected off the skin surface will continue to propagate throughout the skin. Proper wavelength selection as described above will mitigate absorption by other components of the skin.

15. APPLICATION OF A THERMALLY CONDUCTIVE/ TRANSPARENT SUBSTANCE TO THE HAIR DUCTS FOLLOWED BY HAIR CUTTING WITH NO APPLICATION OF A HIGH REFLECTANCE COATING LAYER

This embodiment is essentially the same as the one described by Embodiment 14 except that the high thermal conductivity substance that is inserted into the hair ducts, is chosen to also enhance optical light propagation through it and along the hair duct. Thus the high thermal conductivity substance should also be transparent and, if possible, with lower index of refraction than that of the hair shaft. Bleaching of the hair and removal of pigmentation from the hair shafts (to the highest extent possible) may also be utilized (as a first step in this embodiment) in order to enhance light propagation in the hair shafts themselves and to allow beam energy deposition further down the hair shaft and as deep in the follicle as possible.

16. APPLICATION OF A THERMALLY CONDUCTIVE/ TRANSPARENT SUBSTANCE TO THE HAIR DUCTS, HAIR DYEING AND HAIR SHAFT CUTTING WITH NO APPLICATION OF A HIGH REFLECTANCE COATING LAYER

This embodiment is essentially the same as the one described in Embodiments 14 except that here, instead of attempting to enhance optical penetration in the hair shaft, the principle mechanism of energy transfer thus relies on is thermal conduction from the cut hair shaft down the follicle to the targeted hair-sustaining tissue. Thus, in the practice of the present embodiment, the absorption of the hair shaft is enhanced through application of artificial dye to the hair shafts. The hair dye is chosen to be such that it exhibits strong absorption characteristics in the region of the wavelength of the electromagnetic source. The goal of this embodiment is to allow the beam energy to be efficiently deposited in the region of the upper hair follicle. The use of a substance of high thermal conductivity then ensures efficient transfer of the heat down to the lower hair follicle and papilla.

In this embodiment, prior to insertion of the substance of High Thermal Conductivity and irradiation steps, the hair is dyed with highly absorbing colors (for example china black) in order to enhance light absorption in the hair and conversion of light energy to heat. The hair is then cut as close as possible to the skin, and the irradiation steps follow as described in Embodiment 14. Light is converted to heat and then conducted down the hair follicle to destroy the tissue nourishing the hair.

17. APPLICATION OF A THERMALLY CONDUCTIVE SUBSTANCE TO THE HAIR DUCTS FOLLOWED BY THE DYEING AND CUTTING OF THE HAIR SHAFT WITH NO APPLICATION OF HIGH REFLECTANCE COATING AND SHORT DEPTH OF FOCUS AT SURFACE.

This embodiment is essentially the same as the one described in Embodiments 14, 15 or 16 except that in order to enhance safety, mitigate chances of damaging other skin components, and maximizing absorption of light energy by the surface hair shafts, a beam with short depth of focus is used. The beam is focused on the surface of the skin where the epidermal layer is substantially transparent to the sources electromagnetic energy with the exception of the cut hair shafts protruding through the ducts. The beam energy is strongly absorbed by the hair shafts. Absorption is strongly enhanced through dyeing the hair shafts with dyes which strongly absorb the beam energy at the selected source wavelength. The beam energy converted into heat energy is then conducted by the high thermal conductivity substance to the targeted lower portions of the follicle. The portion of the beam not absorbed by the hair at the surface continues to propagate throughout the skin, but rapidly diverges and scattered since the beam focus is at the skin surface. The beam's power density, thus, rapidly drops. As a consequence of this rapidly dropping power density profile, the total amount of incident electromagnetic energy which is directly absorbed by the lower skin components (the dermis and the hypodermis) is considerably smaller and the risk of collateral damage to skin components not in direct contact with the hair follicle is considerably reduced.

The system optics must be designed to deliver a substantially diverging beam below the skin surface. At the surface, the beam wavelength, total irradiation time, total energy, and fluence must be below ablative threshold but such that the total amount of energy delivered to the hair shafts and distributed throughout the follicle through the substance of high thermal conductivity, is sufficient to bring about irreversible damage to the hair-sustaining tissue. For example 10 J/cm$^2$ delivered over 1 ms time interval will result in coagulation of the entire follicle volume (assuming that the diameter of the follicle is about 200 $\mu$m and its depth about 4 mm). In this time interval heat will only diffuse about 20 $\mu$m out of the heated duct thus bringing about destruction of the follicle components immediately in contact with the substance of high thermal conductivity but substantially sparing most of the rest of the skin components from collateral damage.

18. APPLICATION OF A THERMALLY CONDUCTIVE SUBSTANCE TO THE HAIR DUCTS AND APPLICATION OF COOLANT TO THE SKIN SURFACE WITH NO APPLICATION OF A HIGH REFLECTANCE COATING.

This embodiment is essentially the same as the one described in Embodiments 14, 15, 16, and 17 except that in order to enhance safety and mitigate the potential for damage of other skin components a fluid coolant is applied to the surface. Such a coolant will remove heat deposited in the skin and, in particular, the upper outer portion of the skin. However, deeper regions of the hair shafts, absorbing the beam energy directly and subsequently heating up, are in direct contact with the high thermal conductivity substance in the ducts. Since the hair shafts are not good thermal conductors, heat will not escape rapidly through the tip of the hair shafts in contact with the cooling fluid at the surface. Instead, deeper portions of the hair shafts, will be able to transfer some of their thermal energy to the substance of High Thermal Conductivity and which will aid in delivering this depilatory energy to the targeted hair-sustaining tissue and papilla.

Here, to increase the effectiveness of the present embodiment, improve safety, and prevent the escape of energy deposited in shafts through contact with the cooling liquid at the surface, an alternative embodiment may be used as described below.

This variant involves the application of a substance of high thermal conductivity, forcing this substance into the hair shaft, thoroughly cleaning the surface, applying to the surface a substance of low thermal conductivity (i.e., an insulating substance) and forcing this substance into the hair duct, again, cleaning the surface substantially without removing the substance of low thermal conductivity (which has penetrated the top portion of the hair ducts) from the hair ducts, and, finally, applying the depilatory beam to the surface along with the coolant in contact with the surface.

Thus, in this variant, the surface remains cool, the depilatory beam penetrates and couples radiation to the hair shafts. The beam energy is converted to thermal energy which is then conducted along the hair ducts through the action of the substance of high thermal conductivity. However, since the substance of high thermal conductivity and the thermal energy it is transferring are insulated from the coolant by the substance of low thermal conductivity in the upper portion of the duct. Heat is thus prevented from escaping to the coolant at the surface, while the coolant continue to protect the hair-free skin.

19. APPLICATION OF A FLUID TO THE TREATED SURFACE FOR MATCHING OF THE REFRACTIVE INDEX OF THE SKIN COMPONENTS AND FOR THE SIMULTANEOUS COOLING OF UPPER SKIN COMPONENTS.

Figure 16A:
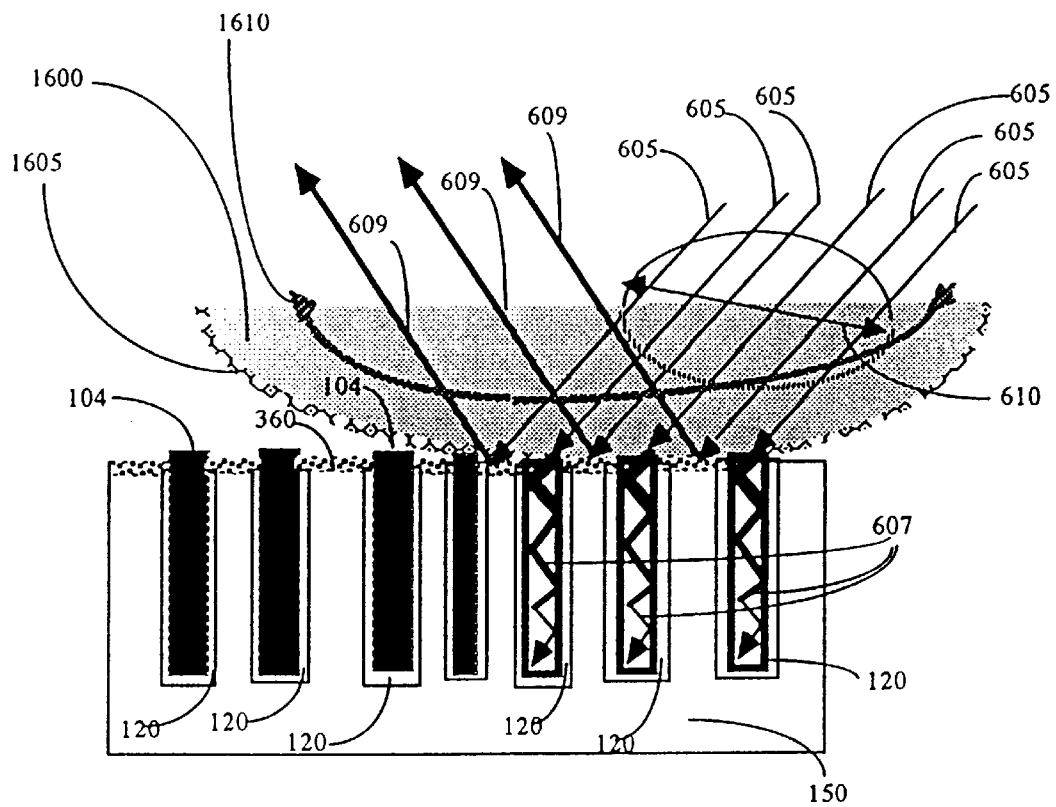
FIG. 16A is a graphical representation of the application of the incident depilatory beam through a transparent, flowing, liquid for enhancement of index matching and surface cooling wherein the container filled with the transparent liquid is in contact with the targeted skin surface.

This embodiment is the same as any one of the embodiments described above except that the surface and the scanning/treatment head are submerged in a fluid that enhances removal of heat (for example, gas, air, water, cryogen, etc.) and matches the refractive index of the targeted object. As FIG. 16A shows, in its last stage of propagation prior to reaching the targeted skin, the incident beam 605 is delivered through a cooling fluid media 1600 (Cooled to within the range of from about 3° C. to about 15° C.), within a delivery head 1605. The delivery head is filled with an index-matched fluid/coolant 1600 which is made to flow in the direction of the arrow 1610.

The fluid/coolant 1600 should have an index of refraction which matches that of the targeted skin components to enhance optical coupling. The targeted skin components can be, for example, cut hair opening, emptied follicular opening, follicular opening filled with optically transport material, etc.

The only embodiments that would not work with this embodiment are those involving a substance of a high thermal conductivity in the hair ducts. The hair ducts can be brought into contact with the cooling fluid or cooled delivery head. Such a contact will then drain the heat out of the hair duct and will defeat the goal of these embodiments which is to conduct the heat down the ducts and into the papilla region.

The cooling of the skin has the additional well-known advantages of reducing risk of thermal damage to the upper layers of the skin and upper components of the hair follicle, of forcing the lower hair follicles and bulb closer to the skin surface (thus shortening the depth to which incoming source energy has to penetrate in order to accomplish its goal of damaging the lower follicle and papilla region) and of erecting the hair shafts and follicles into a more-nearly vertical position. Cooling allows exposure of the skin to higher levels of depilatory beam energy. Cooling also allows the operator extend the time duration of each exposure.

Figure 16B:
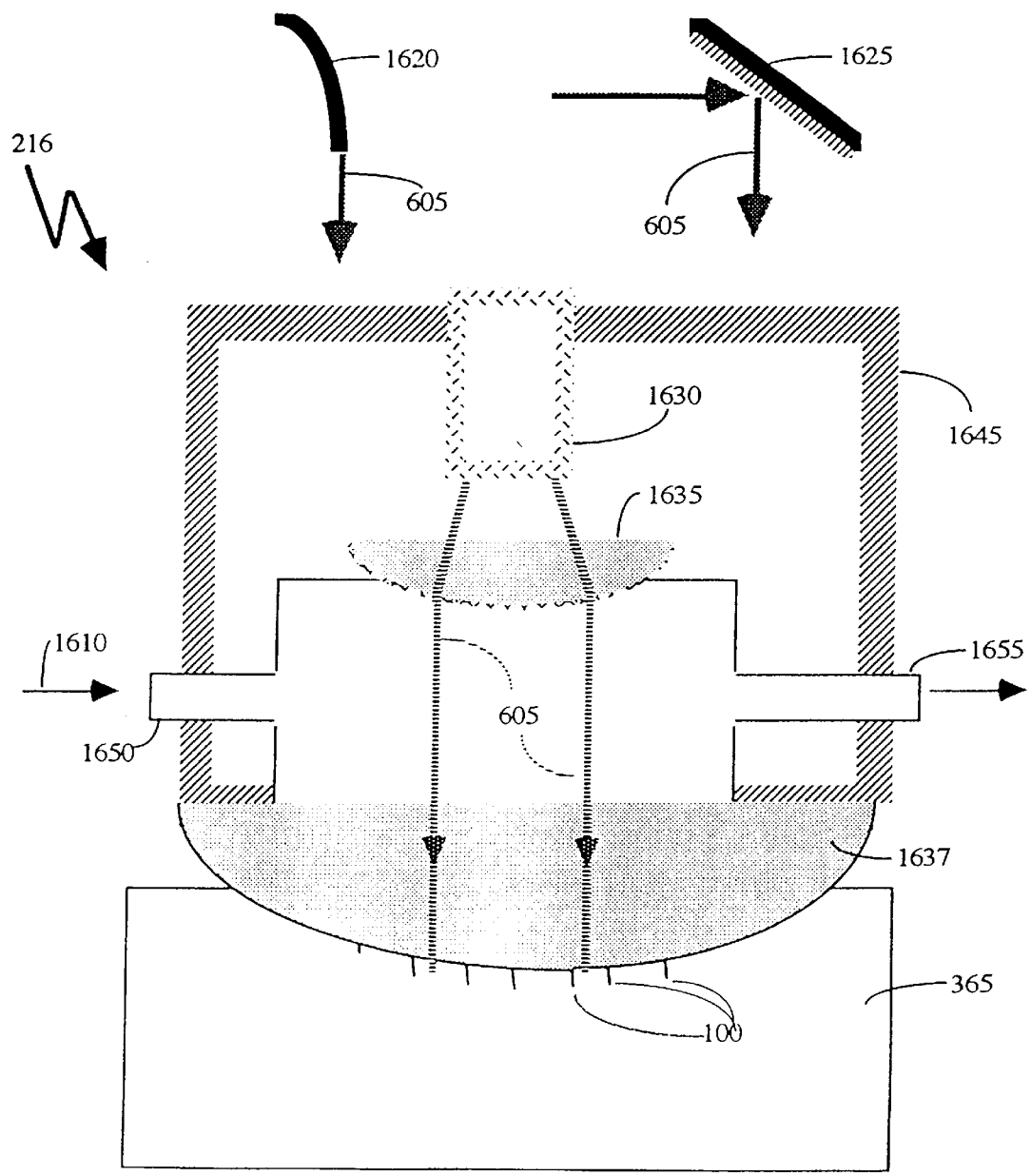
FIG. 16B is a graphical representation of an alternative depilatory beam delivery apparatus capable of cooling a transparent lens or slab in contact with the targeted skin.

An alternative embodiment is shown in FIG. 16B. The scanning/treatment head 216 of the hair-removal system allows delivery of the irradiating field 605 to hair shafts 104 and hair follicles 100 located in the targeted skin area 365. The field 605 may be delivered to the scanning/treatment head 216 using a fiber optic cable 1620 (or other fiber optic devices) containing one or more fibers or fiber optic bundles fitted, through mirrors 1625, or through other optical delivery apparatus, so that the delivered beam is coupled into the scanning/treatment head adapter 1630.

After exiting a waveguide 1620, the field 605 is typically spatially dispersed, and is preferably collected and roughly collimated using a lens. Alternatively, the field may be delivered to the irradiating unit using, for example, one or more reflecting mirrors 1625. This allows the field 605 to be roughly collimated prior to impinging the lens 1635.

After passing through this optic, the beam then impinges on a lens 1637 in contact with the treated surface. Although this lens may be replaced by any transparent material of, for example, flat geometrical shapes, if no additional modification of the treatment beam shape is desired. This lens is preferably placed in contact with the targeted skin region 365.

Both lenses 1635 and 1637 illustrated in FIG. 16B may be made of any geometrical shape of a transparent material if no additional modification of beam shape is desired. Alternatively, these two components may be made of any geometrical shape if a modification in the profile of the incident beam is desired.

The optical, mechanical, and thermal properties of the contact lens 1637 are chosen to allow efficient coupling of the optical radiation into the skin region (leading to the coupled beam 607). Once delivered, the field is used to irradiate, heat, and then remove the hair follicles 100. In addition, the lens 1637 is used to couple light and heat out of the superficial skin layer (i.e., epidermis) of the irradiated region. This allows the deeper part of the hair follicles to be irradiated and heated, permitting permanent destruction of the follicle, while potentially deleterious optical and thermal energy are simultaneously conducted out of the overlying skin layers. Thus, multiple hair follicles can be permanently removed from the skin region without causing pain or injury to the patient.

Both the lens 1635 and 1637 are preferably disposed in a housing 1645 containing both entrance 1650 and exit 1655 ports for fluids such as cooling water or purge gas to flow in the direction of the arrow 1610 into and out of, fluids may be used, for example, to cool the lens 1637 in contact with the skin allowing the skin surface to be cooled.

Alternatively, the housing 1645 may include an electrically controlled cooler in order to provide accurate control over the temperature of the lens 1637 in contact with the skin. Preferably, the temperature of the skin is reduced to between 3° C. and 15° C.

20. APPLICATION OF FLUID TO ACCOMPLISH ADDITIONAL COOLING OF THE SKIN WHEREIN NO MATCHING OF REFRACTIVE INDEX IS ATTEMPTED

This embodiment is essentially the same as that of Embodiment 19 except that no matching of the refractive index between the cooling fluid and the skin is attempted. Thus, this embodiment is also essentially the same as any one of the embodiments described above where the surface and scanning/treatment head is submerged in a fluid that enhances removal of heat (gas, air, water, cryogen, etc.). In this embodiment no consideration is given to matching the optical index of refraction of the targeted objects. The only embodiments that would not work with this embodiment are those involving the forcing of a good thermal conductor into the hair ducts. The cooling of the skin has the additional well-known advantages of reducing thermal damage risk to the upper layers of the skin and upper components of the hair follicle, of pulling the hair follicle and hair shaft upward towards the skin surface (thus shortening the depth to which incoming source energy has to penetrate in order to accomplish its goal of damaging the lower follicle and papilla area) and of erecting the hair shaft and follicle into a more-nearly vertical position.

21. APPLICATION OF A SUBSTANCE OF HIGH REFLECTANCE COATING, IDENTIFYING HAIR SHAFT LOCATION THROUGH HAIR SHAFT CUTTING, ABLATING OR MELTING OF DELIVERY WINDOWS AROUND THE HAIR SHAFTS, DELIVERY OF DEPILATORY ELECTROMAGNETIC ENERGY DOSE THROUGH THE DELIVERY WINDOWS FOR DESTRUCTION OF THE UNWANTED HAIR FOLLICLES.

This embodiment utilizes essentially similar steps to those of Embodiment 1A, 1B, 2A and 2B, except that instead of using the only the hair shafts and/or hair ducts for depilatory energy delivery, a substantially larger opening in the layer of high reflectance coating is created to form a delivery window (for example, 500 $\mu$m in diameter) around a single hair shaft (or around a group of hair shafts close together).

In the narrow beam/single hair interaction method, the reflectance contrast method utilizing the substance of high reflectance coating and hair cutting is used to first identify the hair follicle location using a low-power scanning beam and then a more powerful ablating beam or melting beam is applied to create a delivery window by removing the layer of high reflectance coating. Finally, the depilatory beam is activated and the coupled beam propagating into the skin is substantially confined to the region surrounding the hair follicle.

In the large beam/multiple hair interaction configuration, ablative, abrasive, poking, scratching, and/or melting interaction to open the delivery window around the hair shafts utilizes coating of the skin is coated with a layer of a substance of a high reflectance coating followed by hair shaving. The differential absorption of the pigmented (or even artificially dyed and cut hair shafts create absorbing centers in the hair shafts that will lead to enhanced heating and melting as well as enhanced ablation around the hair shafts.

Using either a large a or small beam, the depilatory beam parameters should utilize a wavelength that is least scattered by the skin (for example in the red to near infrared region of the electromagnetic region) and is absorbed well by the pigments in the hair shafts. For example, light in the range of 750–950 nm, or 1050 to 1150 nm, with pulse duration of 100 $\mu$s to 100 ms and pulse energy of 20 to 100 J/cm$^2$ could serve in the practice of the present embodiment.

Again, the steps taken in the practice of this embodiment are essentially the same as those of Embodiments 1A and 1B and Embodiments 2A and 2B except that an additional step of irradiating the identified hair shafts with a melting and/or ablating beam to remove the layer of high reflectance coating around the hair shafts, is taken prior to application of the depilatory beam.

Yet Another Substantially Different Concept is now Proposed in Embodiment 22 below.

22. IDENTIFICATION OF HAIR SHAFT LOCATIONS THROUGH THE APPLICATION OF A LAYER OF HIGH REFLECTANCE COATING. DESTRUCTION OF HAIR THROUGH SEQUENTIAL PULSE ABLATION OF THE HAIR FOLLICLE.

This embodiment utilizes a substance of high reflectance coating, cutting of hair shafts and the differential reflection characteristics created by these steps, to identify the location of the hair shafts as described in embodiment 2B. Once a hair shaft opening is identified (see, for example, the discussion in Embodiment 2B and FIG. 9), the incident interrogating beam is replaced by a depilatory beam of ablative fluence as described in section above. The depilatory-ablating beam should preferably, but not necessarily, be generated by an ultrashort pulse laser source which allow high-aspect ratio interaction drilling. Craters 50 $\mu$m in diameter but several millimeters deep can easily be achieved with some type of lasers. Ultrashort pulse lasers are also very sensitive to threshold fluence level and will cease ablating once the beam fluence drops below the threshold fluence level. It is thus particularly easy to design beams of spatial profiles that results in increasing spot sizes. This, in turn, will allow decreasing fluence levels which will drop below the ablation threshold once the craters have reached the bottom of the follicles.

The following steps should thus be taken:

a. Application of a substance of high reflectance coating.

b. Cutting of the hair shafts.

c. Identification of the locations of the hair shafts a as described in Embodiment 2B.

d. Activation of the depilatory beam with above-threshold fluences as described above.

e. Progressive ablation of the hair root structure until the bottom of the hair bulb and papilla are reached.

f. Turning the depilatory beam laser off.

Turning off the beam at the ablation end-point (i.e., the point when the ablating beam has reached the targeted hair bulb and papilla) can be pre-set in a number of different ways. For example, by estimating the expected depth at which the hair bulb and papilla are located, the ablating beam spatial profile can be determined so that its fluence falls below ablation threshold. Alternatively, by knowing the ablation depth per pulse (for example, ultrashort pulse lasers remove approximately one micrometer with each pulse), it is possible to predetermine the total number of pulses that would be needed to ablate the full length of the hair shafts. Also, with the high pulse repetition rate (for example, in the range of about several hundred pulses per second or even in excess of about 1000 Hz possible for ultrashort pulse ablation), it is possible to remove material from an exemplary depth of 4 mm in approximately 4 seconds.

Other techniques for ablation endpoint determination may utilize; i) optical tomography/low coherent reflectometry which determine the depth of the hair shafts, depth of the ablation craters, or location of the root bulbs. ii) During ablation, changes in the plume's laser-induced fluorescence or laser-induced luminescence can be detected thus indicating, for example, when the beam has ceased ablating hair shaft material and has began ablating the soft tissue below the hair shafts.

23. APPLICATION OF A SUBSTANCE OF HIGH REFLECTANCE/HIGH THERMAL CONDUCTIVITY TO THE SKIN SURFACE OVER AN AREA SUBSTANTIALLY LARGER THAN THE REGION TARGETED FOR REMOVAL IN ORDER TO ACT AS AN EFFICIENT HEAT EXCHANGER AND UTILIZING HAIR SHAFT SHAVING.

This embodiment can be employed with most other embodiments mentioned above except that care must be taken for the embodiments utilizing a substance of high thermal conductivity to conduct thermal energy down the follicle and into the targeted lower follicle and papilla region. In these cases no thermal contact can be allowed between the high reflectance coating/high thermal conductivity coating on the surface and that of substance of high thermal conductivity in the hair ducts and hair follicles.

The basic idea utilized in this embodiment is that the high reflectance substance should also be a good thermal conductor. In this case, such an applied layer of coating will serve to both reflect the incoming beam not intercepting the cut hair shafts, and also act as a heat exchanger to radiate and remove excess heat from the skin surface. Such a substance will rapidly transfer excess heat deposited near the skin surface to the entire coated area. The larger the extent of the surface area covered by the high reflectance/high conductivity substance, the faster the transfer of heat to the ambient atmosphere over the treated area will occur.

Figure 17:
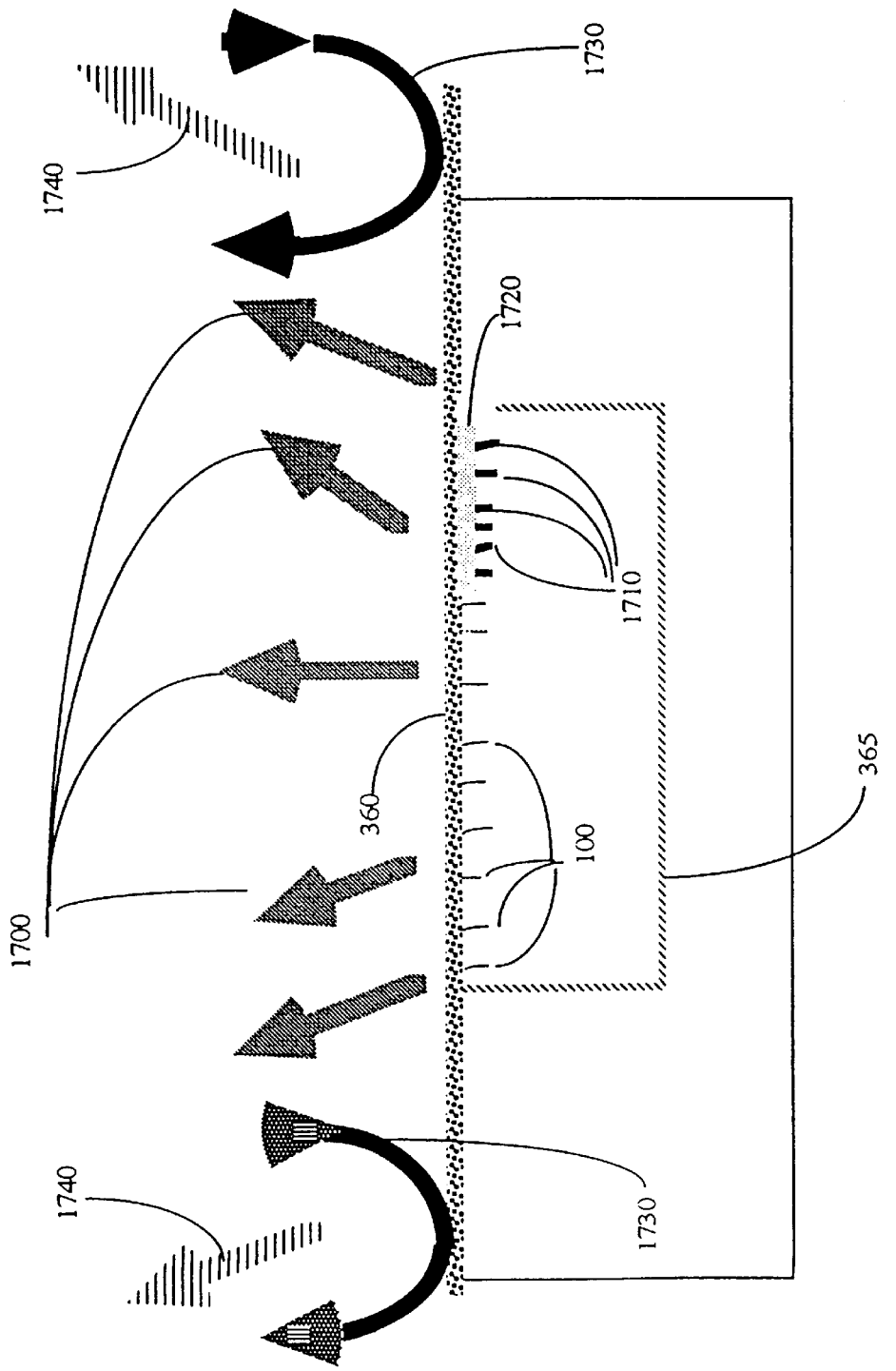
FIG. 17 is a graphical representation of utilizing a layer of a substance of both high reflectance and high thermal conductivity to enhance cooling of the treated skin surface.

This embodiment is further illustrated in FIG. 17. Here, the extensive cover of the skin surface with a high reflectance/high conductivity substance 360 beyond the targeted area 365 is utilized in order to facilitate and expedite surface cooling.

The hair shafts are then cut or removed in accordance with one of the embodiments discussed above and the depilatory beam is used to deposit energy in the hair shafts, hair ducts and follicles 100. Excess thermal energy in the surface of the skin is coupled to the substance of high reflectance/high conductivity 365 and thermal energy deposited at the surface is rapidly spread throughout the this layer and transported—as shown by the arrows 1700—to the cool ambient air or gas above the surface. An auxiliary/additional external cooling can be applied as indicted by the arrows 1730. Such an auxiliary/additional cooling may include fluid flow to allow enhanced heat transport as indicated by the arrows 1740 and surface cooling. Cooling of the directly irradiated/treated area 365 as described in the embodiments and figures above is also possible.

As was mentioned, in cases where high thermal conductivity is employed to transport heat within the hair follicles 1710 as part of the invention methods for destruction of the hair follicle, care must be taken not to allow contact between the HTC substance in the follicle and the high reflectance/high thermal conductivity substance coating the surface. Such a discontinuity may be created through, for example, ablation of the layer of the substance of high thermal conductivity/high reflective coating directly above the follicle or, for example, through the application of a layer of insulating substance. Both techniques were described above. Such a discontinuity or gap is indicated by the spacing 1720 between the follicles 1710 and the surface coating 360 in FIG. 17.

Finally, the present embodiment (utilizing said enhanced heat transfer) is expected to be particularly effective and useful in conjunction with the previously discussed embodiments employing hair shaft bleaching, hair shaft removal, and the creation of delivery windows (including all their related variants).

24. THE USE OF A STYLUS OR THE LIKE TO FORM AN ELECTROMAGNETIC ENERGY TRANSMISSIVE WINDOW IN THE REFLECTIVE COATING ABOVE THE HAIR.

Optionally, the reflective coating is selectively removed at each follicle, so as to allow light energy to enter the follicle. The removal may be effected by mechanical scrapping abrading, or poking by utilizing a needle, stylus or the like, or alternatively via laser ablation or the like.

When laser ablation is used to remove the reflective coating, a first laser pulse removes the reflective coating at and around the follicle and a second laser pulse effects hair removal.

When a stylus is used, the stylus preferably has a tip which has a diameter of between approximately 100 micrometers and approximately 1 mm, so as to facilitate removal of the desired amount of the reflective coating (typically an amount approximating either the cross-sectional area of the hair to be removed or the area of the opening of the follicle. The stylus may be either manual manipulated or may be automatically controlled and manipulated.

25. THE CONFIGURATION OF AN ELECTROMAGNETIC PULSE SUCH THAT THE PULSE IS COMPRESSED DURING PROPAGATION THEREOF TOWARD THE PAPILLA.

Optionally, the electromagnetic energy can be configured such that the pulse is compressed during propagation thereof toward the papilla so as to exceed an interaction threshold of the papilla in a manner which results in modification or destruction of the papilla or other hair sustaining tissue. Such compression of the electromagnetic pulse may be achieved by configuring an electromagnetic pulse which comprises a plurality of different frequencies. As those skilled in the art will appreciate, electromagnetic energy at different frequencies typically travels at different speeds through a given media. Thus, the electromagnetic pulse is configured such that the different frequency components arrive at the papilla at approximately the same time, such that the energy density at the papilla is greater than the energy density of the electromagnetic pulse prior to reaching the papilla.

In this manner, a greater amount of energy may be transmitted to the papilla without tending to damage or modify adjacent tissue.

Figure 18:
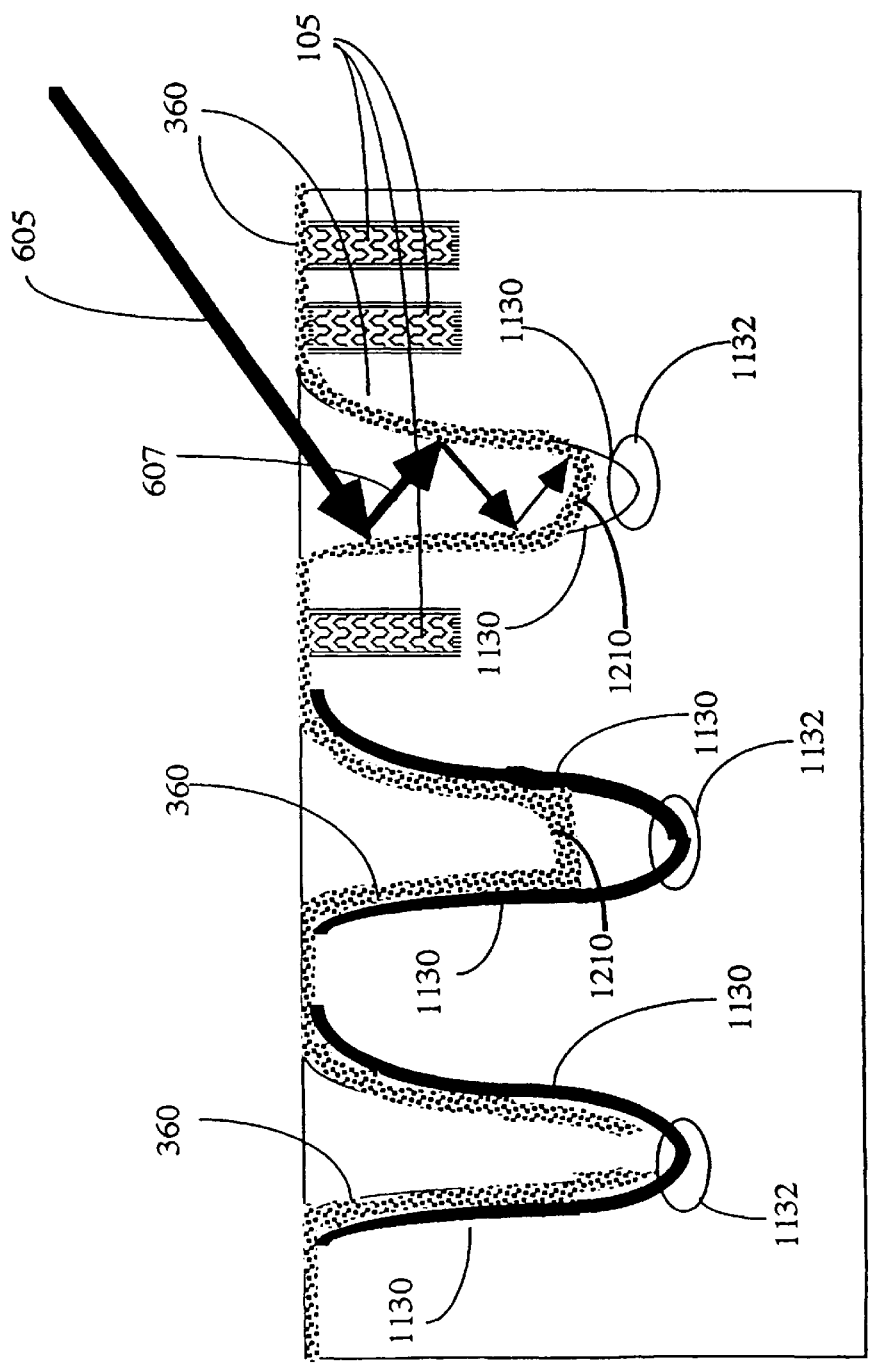
FIG. 18 is a graphical representation of the process of acne treatment using a reflective coating.
Figure 19:
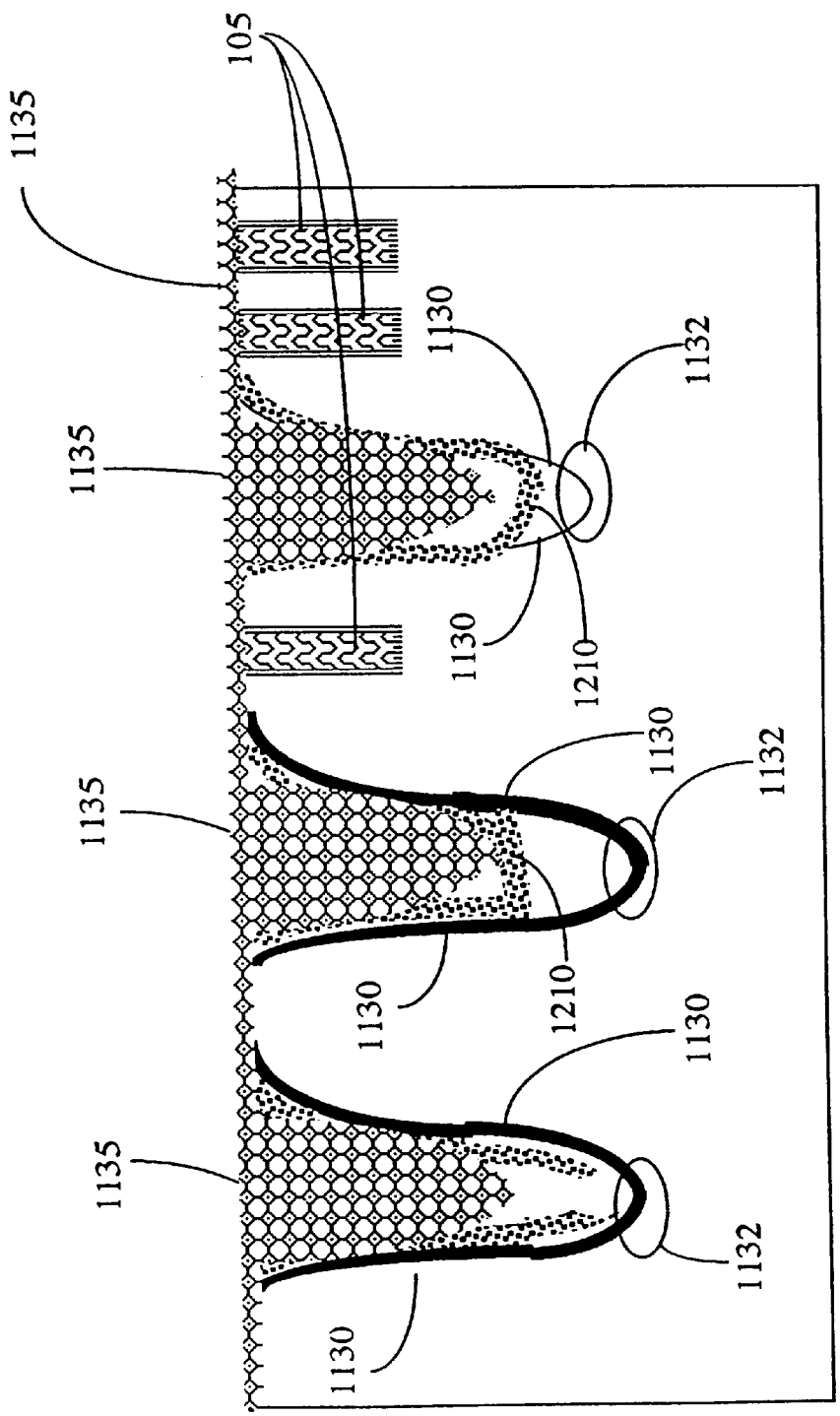
FIG. 19. is a graphical representation of the process of acne treatment using a thermally conductive substance.

Referring now to FIGS. 18 and 19, the present invention provides a method and apparatus for the treatment and prevention of acne. The treatment of acne according to the present invention relies upon the differential opening in the skin caused by acne. The differential opening in the skin of a human, in particular provides a method for facilitating the treatment of acne according to the present invention.

As those skilled in the art will appreciate, acne occurs substantially due to improper drainage of the hair follicle opening. The hair follicle opening of a human being is approximately on the order of 50 $\mu$m to about 150 $\mu$m. The openings of other pores in human skin are substantially smaller than 50 μm.

With particular reference to FIG. 18, according to the present invention, a method for treating acne comprises the steps of pulling a hair shaft out of the follicle 1130 when hair is growing out of the targeted skin area. The hair shaft may be pulled out of the follicle 1130 by wax epilation, or any other desired method.

Next, a substantially reflective coating 360 is applied to the skin and the target area. According to the preferred embodiment of the present invention, the reflective coating 360 comprises a suspension of reflective particles which are capable of reflecting a substantial portion of the light 605 incident upon them. Thus, very little of the incident light 605 is absorbed by the skin beneath the reflective coating. For example, the metallic particles preferably reflect over 90% of the incident light.

The reflective metal particles in the suspension should be sized such that they are larger than the sweat pores 105 of the skin, typically greater than approximately 30 μm. The reflective metal particles should also be smaller than the size of the hair follicle 1130 opening and the targeted skin of the patient, which is typically approximately 50–150 μm, generally approximately 80 μm. The reflective particle suspension is rubbed into the skin so that the reflective particles coat and cover the skin and sweat pores (as well as other openings in the skin), but the reflective particles are forced into the hair follicle openings so that they substantially do not completely block the hair follicle 1130 openings.

An electromagnetic or other energy source which is capable of being substantially reflected by the high reflective particles in the suspension is then applied to the skin. The applied energy is substantially reflected from most of the skin, but is trapped and propagated down the hair follicle 1130 so as to ablatiatively remove the substance which is blocking the opening thereof. In this manner, drainage of the hair follicle 1130 is enhanced. Thus, according to the present invention, the blockage 1210 is heated and destroyed or modified so as to at least partially open the blocked opening and the hair follicle, thereby facilitating such enhanced drainage.

Further, the application of such electromagnetic or other energy may cause partial or complete destruction of a hair sustaining component 1132 within the hair follicle and/or the hair follicle itself, thus facilitating enhanced drainage and/or the mitigation or elimination of secretions from the treated follicles 1130. Since hair growth is frequently not desired from such skin areas which are affected by acne, i.e., typically facial skin, the elimination of hair growth from such skin areas may provide an addition benefit. The destruction of fat/lipid secreting glands is not generally desired, but under some circumstances may be desired and may be accomplished via this process.

The use of a highly precise interaction, such as an interaction generated by very short pulses, may be particularly useful since such interactions are substantially limited in space and may thus minimize collateral damage in the area adjacent to the targeted opening of the hair follicle 1130. Additionally, the localization of such an interaction may be enhanced due to funneling of the incoming electromagnetic radiation, wherein the incoming electromagnetic radiation is at a level below the interaction threshold thereof initially, but is funneled down to a higher energy density by the coating upon the walls of the follicle openings, wherein the interaction threshold is exceeded as the opening in the follicle narrows.

With particular reference to FIG. 19, the present invention provides another method for treating acne. According to this alternative method, a material 1135 comprising a suspension of high thermal conductivity material 1135 is applied to the area to be treated. This thermally conductive material 1135 is forced into the hair ducts. Optionally, ultrasound is used to facilitate the forcing of the thermally conductive material 1135 into the hair ducts or follicles 1130, as discussed above. The thermally conductive material 1135 should comprise particles which are large enough not to enter sweat pores 105 or any other openings in the skin other than the hair duct openings, which are typically greater than approximately 40 μm, but smaller than approximately 80 μm in diameter. This may be accomplished by superficially wiping or cleaning the surface of the targeted skin area after the thermally conducted substance has been applied to the skin. Such wiping or cleaning is performed such that it removes a substantial portion of the thermally conductive substance from the skin, but does not remove it from the hair ducts or follicles. Optionally, the substance of high thermal conductivity also has enhanced absorption in the frequency range of the electromagnetic radiation used.

Next, a heat source such as a laser, or electromagnetic energy source, is applied to the surface. Since the skin is a substantial insulator of heat, a substantial portion of the heat or energy applied to the skin is transmitted through the thermally conductive substance, thereby causing the thermally conductive 1135 substance to heat up and thereby open the pores, thus cleaning the hair ducts or follicles 1130.

As a further alternative, a substance having high absorption of thermal or electromagnetic energy is applied to the surface to be treated. This high absorption substance is forced down into the hair ducts, as discussed above. Again, the particles comprising the high absorption substance are sized such that they are not capable of substantially penetrating other pores or openings in the skin surface.

The skin surface is wiped off or cleaned so as to substantially remove the substance from the skin surface, without removing the substance from the hair ducts or follicles.

Electromagnetic radiation or other energy is then applied to the surface of the skin so that the electromagnetic radiation or other energy is substantially absorbed, mostly by the substance of high absorption which is disposed within the hair ducts. Electromagnetic energy can be selectively applied so as to ablate or heat only the region of the opening of the hair ducts in a manner which facilitates drainage and cleaning of the hair ducts.

When an expandable material or a high absorption material is disposed within the follicles to provide acne treatment and a reflective coating is used to protect nearby tissue, the a stylus may optionally be used to selectively remove the reflective coating.

A substance having a sufficiently high thermal coefficient of expansion to cause expansion of the hair follicle may be inserted thereinto. Thus, heating of this material will tend to loosen, dislodge, destroy, or otherwise desirably modify the blockage within the follicle so as to allow drainage thereof. Examples of such materials include animal fats, organic molecules and metals.

The expanding substance is optionally impregnated with electromagnetic radiation absorbing material, so as to facilitate the heating thereof. Carbon is one example of such an electromagnetic radiation absorbing material.

Optionally, a reflective material may be disposed within the follicle, preferable upon walls thereof, so as to cause internal reflections which tend to maintain a substantial portion of electromagnetic radiations within the follicle.

The use of a high reflective coating, a thermally conductive substance and a high thermal coefficient of expansion substance, described above for the treatment of acne may be combined in any desired manner, so as to better facilitate the treatment process.

Indeed, various desired procedures described above for hair removal and/or the treatment of acne may be combined as desired, so as to facilitate effective treatment.

It is understood that the exemplary method and apparatus for permanent hair removal described herein and shown in the drawings represents only presently preferred embodiments of the invention. Indeed, various modifications and additions may be made to such embodiments without departing from the spirit and scope of the invention. For example, various sources of electromagnetic radiation, both coherent and incoherent, may be utilized for either interrogation or epilation. Also, various means may be used to sense the location and orientation of hairs. Thus, these and other modifications and additions may be obvious to those skilled in the art and may be implemented to adapt the present invention for use in a variety of different applications.

I claim:

1. A method for removing hair from a region of skin, the method comprising the steps of:
    coating the region of skin substantially with a reflective material;
    removing reflective material in an area of skin proximate each hair to be removed; and
    directing electromagnetic energy through the area of skin where the reflective coating has been removed and toward a papilla of each hair to be removed, the electromagnetic energy being configured to inhibit hair growth.

2. The method as recited in claim 1, further comprising the step of modifying the papilla and hair-sustaining tissue with the electromagnetic radiation.

3. The method as recited in claim 1, further comprising the step of destroying the papilla and hair sustaining tissue with the electromagnetic radiation.

4. The method as recited in claim 1, further comprising the step of allowing the hair to grow to a length of at least about 0.2 mm above the skin surface prior to the step of coating the region of skin substantially with a reflective material.

5. The method as recited in claim 1, further comprising the step of allowing the hair to grow to a length between approximately 0.2 mm and approximately 2 cm prior to the step of coating the region of skin substantially with a reflective material.

6. The method as recited in claim 1, further comprising the steps of cleaning and disinfecting the region of skin where hair is to be removed prior to the step of coating the region with a reflective material.

7. The method as recited in claim 1, wherein the step of coating the region of skin substantially with a reflective material comprises coating the region of skin substantially with a solid reflective material.

8. The method as recited in claim 1, wherein the step of coating the region of skin substantially with a reflective material comprises coating the region of skin substantially with a liquid reflective material.

9. The method as recited in claim 1, wherein the step of coating the region of skin substantially with a reflective material comprises coating the region of skin substantially with a gaseous reflective material.

10. The method as recited in claim 1, wherein the step of coating the region of skin substantially with a reflective material comprises coating the region of skin substantially with a solid reflective material suspended in a liquid.

11. The method as recited in claim 1, wherein the step of coating the region of skin substantially with a reflective material comprises coating the region of skin substantially with a reflective material having a reflectivity of at least 80 percent for the wavelength of the electromagnetic energy.

12. The method as recited in claim 1, wherein the step of coating the region of skin substantially with a reflective material comprises coating the region of skin substantially with a reflective material comprised of particles which are too large to be infiltrated by the skin.

13. The method as recited in claim 1, wherein the step of coating the region of skin substantially with a reflective material comprises coating the region of skin substantially with a reflective material comprised of particles having a diameter greater than approximately 30 micrometers.

14. The method as recited in claim 1, wherein the step of coating the region of skin substantially with a reflective material comprises coating the region of skin substantially with a reflective material selected from the group consisting of:
    metallic particles in suspension;
    metallic dye;
    an aluminum containing compound;
    body paint;
    a dielectric coating; and
    a plurality of dielectric coatings.

15. The method as recited in claim 1, wherein the step of coating the region of skin substantially with a reflective material comprises coating the region of skin substantially with a material comprising metallic particles, the metallic particles being sufficiently large so as to mitigate infiltration of the skin thereby.

16. The method as recited in claim 1, wherein the step of coating the region of skin substantially with a reflective material comprises coating the region of skin substantially with a reflective material which is not substantially damaged by an energy beam having an intensity of up to $10^9$ W/cm$^2$.

17. The method as recited in claim 1, wherein the step of coating the region of skin substantially with a reflective material comprises coating the region of skin substantially with a reflective material via a brush.

18. The method as recited in claim 1, further comprising the step of removing the reflective coating after the step of directing electromagnetic energy through the area of skin where the reflective coating has been removed.

19. The method as recited in claim 1, further comprising the step of removing the reflective coating with soap after the step of directing electromagnetic energy through the area of skin where the reflective coating has been removed.

20. The method as recited in claim 1, further comprising the step of removing the reflective coating with solvent after the step of directing electromagnetic energy through the area of skin where the reflective coating has been removed.

21. The method as recited in claim 1, further comprising the step of cooling the region of skin prior to the step of directing electromagnetic energy through the area of skin where the reflective coating has been removed.

22. The method as recited in claim 1, wherein the step of removing reflective coating in an area of skin proximate each hair to be removed comprises cutting the hair to be removed.

23. The method as recited in claim 1, wherein the step of removing reflective coating in an area of skin proximate each hair to be removed comprises shaving the hair to be removed.

24. The method as recited in claim 1, wherein the step of removing reflective coating in an area of skin proximate each hair to be removed comprises removing the reflective coating with a laser.

25. The method as recited in claim 1, wherein the step of removing reflective coating in an area of skin proximate each hair to be removed comprises removing the reflective coating with a stylus.

26. The method as recited in claim 1, wherein the step of removing reflective coating in an area of skin proximate each hair to be removed comprises removing the reflective coating with a stylus, the stylus comprising a tip having a diameter of between approximately 20 micrometers and approximately 2 mm.

27. The method as recited in claim 1, wherein the step of removing reflective coating in an area of skin proximate each hair to be removed comprises removing the reflective coating immediately above each follicle to be removed.

28. The method as recited in claim 1, wherein the step of removing reflective coating in an area of skin proximate each hair to be removed comprises removing reflective coating immediately above a follicle of each hair to be removed, the area of the reflective coating removed being approximately equal to between approximately 0.2 hair diameters and approximately 15 hair diameters.

29. The method as recited in claim 1, wherein the step of directing electromagnetic energy through the area of skin where reflective coating has been removed and toward a papilla of hair to be removed comprises directing light through the area of skin where reflective coating has been removed and toward a papilla of hair to be removed.

30. The method as recited in claim 1, wherein the step of directing electromagnetic energy through the area of skin where reflective coating has been removed and toward a papilla of hair to be removed comprises directing laser energy through the area of skin where reflective coating has been removed and toward a papilla of hair to be removed.

31. The method as recited in claim 1, wherein the step of directing electromagnetic energy through the area of skin where reflective coating has been removed and toward a papilla of hair to be removed comprises sequentially directing electromagnetic energy through the area of skin where reflective coating has been removed and toward the papilla of a plurality of hairs, substantially one hair at a time.

32. The method as recited in claim 1, wherein the step of directing electromagnetic energy through the area of skin where reflective coating has been removed and toward a papilla of hair to be removed comprises directing electromagnetic energy through the area of skin where reflective coating has been removed and onto the papilla of a plurality of hairs simultaneously.

33. The method as recited in claim 1, further comprising the step of disposing an energy transmission enhancing material within a follicle so as to enhance the transmission of energy through the follicle to the papilla.

34. The method as recited in claim 1, further comprising the step of disposing an electromagnetic energy transmission enhancing material within a follicle so as to enhance the transmission of electromagnetic energy through the follicle to the papilla.

35. The method as recited in claim 1, further comprising the step of disposing a heat transmission enhancing material within a follicle so as to enhance the transmission of heat through the follicle to the papilla.

36. The method as recited in claim 1, further comprising the step of disposing an energy transmission enhancing material within a follicle by rubbing the energy transmission enhancing material onto the region of skin where hair is to be removed.

37. The method as recited in claim 1, further comprising the step of disposing an energy transmission enhancing material within a follicle by rubbing the energy transmission enhancing material onto the region of skin where hair is to be removed and subsequently massaging the region of skin where hair is to be removed.

38. The method as recited in claim 1, further comprising the step of disposing an energy transmission enhancing material within a follicle by rubbing the energy transmission enhancing material onto the region of skin where hair is to be removed and subsequently applying ultrasound energy to the region of skin where hair is to be removed.

39. The method as recited in claim 1, further comprising the step of disposing an energy transmission enhancing material within a follicle by rubbing the energy transmission enhancing material onto the region of skin where hair is to be removed and subsequently applying ultrasound energy to the region of skin where hair is to be removed, the ultrasound energy having a frequency between approximately 3.0 MHz and approximately 10 MHz and a power level between approximately 0.1 watt and 0.2 watt and being applied for a duration of between approximately 2 minutes and approximately 20 minutes.

40. The method as recited in claim 1, further comprising the step of disposing an energy transmission enhancing material within a follicle so as to enhance the transmission of energy through the follicle to the papilla, the energy transmission enhancing material being selected from the group consisting of:

water;

oil;

argon;

helium;

nitrogen;

carbon dioxide; and air.

41. The method as recited in claim 1, further comprising the step of disposing an energy transmission enhancing material within a follicle so as to enhance the transmission of energy through the follicle to the papilla, the energy transmission enhancing material being comprised of a material having an index of refraction which is less than the index of refraction of the hair.

\* \* \* \* \*